US005855798A

United States Patent [19]

Phillips et al.

[11] Patent Number: 5,855,798

[45] Date of Patent: Jan. 5, 1999

[54] PROCESS FOR SPONTANEOULY TRANSPORTING A FLUID

[75] Inventors: Bobby M. Phillips, Jonesborough; Shriram Bagrodia, Kingsport; William A. Haile, Kingsport; Harry P. Hall, Kingsport; David A. Casey, Kingsport; J. Nelson Dalton, Kingsport; Ronnie J. Jones, Kingsport; Ronald S. Scalf, Bluff City; Richard D. Neal, Kingsport; Lewis C. Trent, Jonesborough; Jack L. Nelson, Johnson City, all of Tenn.

[73] Assignee: Eastman Chemical Company, Kingsport, Tenn.

[21] Appl. No.: 618,702

[22] Filed: Mar. 20, 1996

Related U.S. Application Data

[62] Division of Ser. No. 133,426, Oct. 8, 1993, Pat. No. 5,611,981, which is a division of Ser. No. 736,267, Jul. 23, 1991, which is a continuation-in-part of Ser. No. 333,651, Apr. 4, 1989, abandoned.

[51] Int. Cl.[6] .................... B01D 39/16

[52] U.S. Cl. .................... 210/767; 210/500.1

[58] Field of Search .................... 210/500.1, 600, 210/767

[56] References Cited

U.S. PATENT DOCUMENTS

| | | |
|---|---|---|
| 870,280 | 11/1907 | Gallagher et al. . |
| 2,637,893 | 5/1953 | Shaw . |
| 2,945,739 | 7/1960 | Lehmicke . |
| 3,050,821 | 8/1962 | Kilian . |
| 3,109,195 | 11/1963 | Combs et al. . |
| 3,109,768 | 11/1963 | Ellingsen . |
| 3,121,040 | 2/1964 | Shaw et al. . |
| 3,156,607 | 11/1964 | Strachan . |
| 3,226,795 | 1/1966 | Swerdloff et al. . |
| 3,249,669 | 5/1966 | Jamieson . |
| 3,425,893 | 2/1969 | Sims . |
| 3,508,390 | 4/1970 | Bagnall et al. . |
| 3,584,103 | 6/1971 | Harris et al. . |
| 3,623,939 | 11/1971 | Ono et al. . |
| 3,650,659 | 3/1972 | Stapp . |
| 3,681,188 | 8/1972 | Harris et al. . |
| 3,914,488 | 10/1975 | Gorrafa . |
| 3,938,522 | 2/1976 | Repke . |
| 4,044,768 | 8/1977 | Mesek et al. . |
| 4,054,709 | 10/1977 | Belitsin et al. . |
| 4,102,340 | 7/1978 | Mesek et al. . |
| 4,179,259 | 12/1979 | Belitsin et al. . |
| 4,245,001 | 1/1981 | Phillips et al. . |
| 4,282,874 | 8/1981 | Mesek . |
| 4,285,342 | 8/1981 | Mesek . |
| 4,286,005 | 8/1981 | Berger . |
| 4,324,247 | 4/1982 | Aziz . |
| 4,332,761 | 6/1982 | Phillips et al. . |
| 4,333,483 | 6/1982 | Holtman . |
| 4,378,414 | 3/1983 | Sawyer et al. . |
| 4,381,325 | 4/1983 | Masuda et al. . |
| 4,469,746 | 9/1984 | Weisman et al. . |
| 4,501,586 | 2/1985 | Holtman . |
| 4,536,420 | 8/1985 | Rickert, Jr. . |
| 4,623,329 | 11/1986 | Probish et al. . |
| 4,654,040 | 3/1987 | Luceri . |
| 4,668,566 | 5/1987 | Braun . |
| 4,678,464 | 7/1987 | Holtman . |
| 4,681,577 | 7/1987 | Stern . |
| 4,685,914 | 8/1987 | Holtman . |
| 4,707,409 | 11/1987 | Phillips . |
| 4,721,647 | 1/1988 | Nakamishi et al. . |
| 4,731,066 | 3/1988 | Korpman . |

FOREIGN PATENT DOCUMENTS

| | | |
|---|---|---|
| 0188091 | 7/1986 | European Pat. Off. . |
| 223908 | 6/1987 | European Pat. Off. . |
| 301874 | 2/1989 | European Pat. Off. . |
| 316771 | 5/1989 | European Pat. Off. . |
| 955625 | 1/1950 | France . |
| 2588285 | 4/1987 | France . |
| 430741 | 6/1926 | Germany . |
| 3634139 | 4/1987 | Germany . |
| 2-04975 | 2/1990 | Japan . |
| 1171027 | 11/1969 | United Kingdom . |
| 1171028 | 11/1969 | United Kingdom . |
| WO 89/01062 | 2/1989 | WIPO . |
| WO 90/12130 | 10/1990 | WIPO . |
| WO 91/12949 | 9/1991 | WIPO . |
| WO 92/00407 | 1/1992 | WIPO . |
| WO 92/09654 | 6/1992 | WIPO . |
| WO 93/07313 | 4/1993 | WIPO . |

OTHER PUBLICATIONS

F. Brochart–Wyart et al., *Annali di Chimica*, 77, pp. 275–283 (1987).

(List continued on next page.)

*Primary Examiner*—Leo B. Tentoni
*Attorney, Agent, or Firm*—Cheryl J. Tubach; Harry J. Gwinnell

[57] ABSTRACT

Synthetic fiber that are capable of spontaneously transporting water on their surface satisfy the equation $$(1-X\cos\theta_a)<0,$$

wherein $\theta_a$ is the advancing contact angle of water measured on a flat film made from the same material as the fiber and having the same surface treatment, if any, X is a shape factor of the fiber cross-section that satisfies the following equation $$X=\frac{P_w}{4r+(\pi-2)D}$$

wherein $P_w$ is the wetted perimeter of the fiber and r is the radius of the circumscribed circle circumscribing the fiber cross-section and D is the minor axis dimension across the fiber cross-section, and wherein the uphill flux value of said fiber is from 2 to 60 cc/g/hr when measured from a reservoir of synthetic urine test fluid along a 20 cm long ramp to an absorbant on an attached platform at 10 cm height.

8 Claims, 52 Drawing Sheets

OTHER PUBLICATIONS

B.J. Carroll, *Journal of Colloid and Interface Scienc*, 97 (1) pp. 195–200 (1984).

A.M. Schwartz et al., *J. Coll. Sci.*, 14 pp. 572–583 (1959).

B. Miller et al., *Textile Research Journal*, pp. 150–155 (1978).

D.K. Owens et al., *Journal of Applied Polymer Science*, 13, pp. 1741–1747 (1969).

A.H. Ellison et al., *J. Phys. Chem.*, 58, pp. 503–506 (1954).

H.W. Fox et al., *J. Coll. Sci.*, 7, pp. 428–442 (1952).

H. Schonhorn, *J. Adhesion*, 23, pp. 147–161 (1987).

K.L. Adams et al., *Textile Research Journal*, pp. 647–654 (1987).

N.R.S. Hollies et al., *Textile Research Journal*, pp. 829–835 (1956).

F.W. Minor et al., *Textile Research Journal*, pp. 931–939 (1959).

B.D. Summ et al., *Colloids and Surfaces*, 27, pp. 43–55 (1987).

Derwent Abstract WPI Acc. No. 80–02782c/02–13 JP A 151617–1979, Nov. 29, 1979.

*Encyclopedia of Polymer Science and Engineering*, vol. 6, pp. 802–839 (1986).

Abstract of Japan 56–37,309 (Published Apr. 11, 1981).

Netherland Abstract OCTROOI No. 8490, dated Nov. 28, 1922.

Patent Abstracts of Japan, vol. 5, No. 94 (C–59), Jun. 19, 1981.

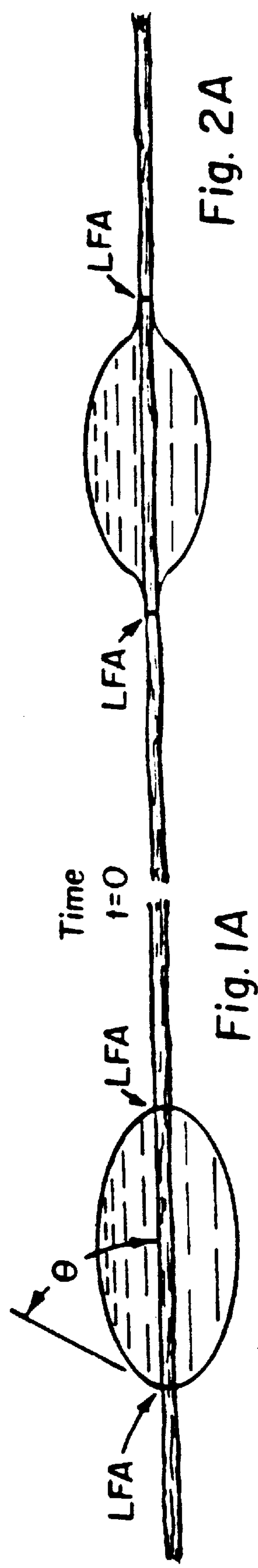
LFA
LFA
Fig. 2A
Time
t=0
LFA
LFA
θ
Fig. 1A
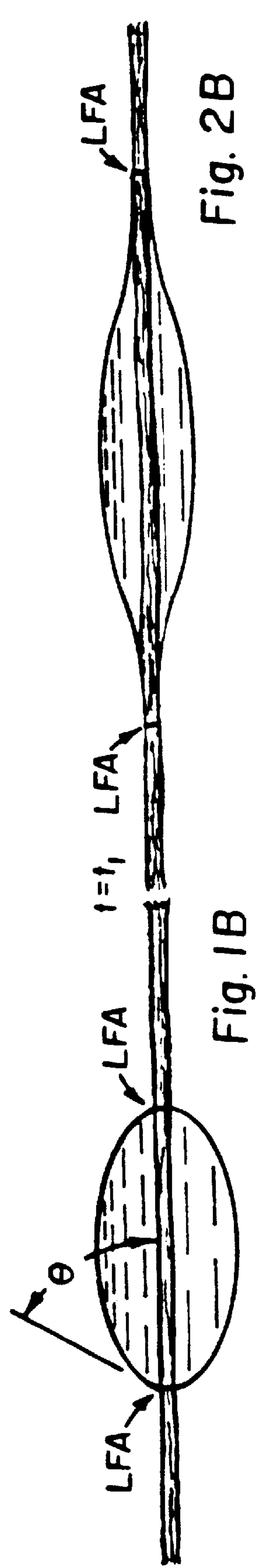
LFA
LFA
Fig. 2B
$t=t_1$
LFA
LFA
θ
Fig. 1B
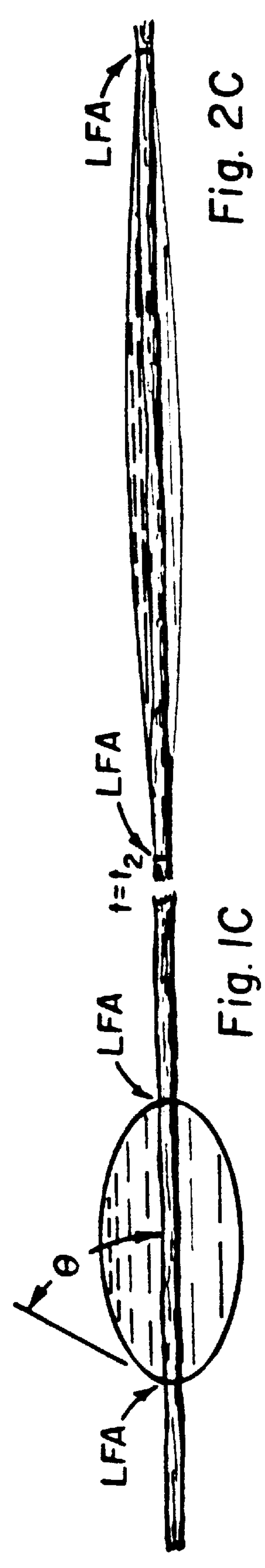
LFA
LFA
Fig. 2C
$t=t_2$
LFA
LFA
θ
Fig. 1C PEN CARTRIDGE COMPARISON
8 D/F POLYESTER FIBER - 4SW vs ROUND
4SW (3.4 % LUBE)
ROUND (1% LUBE)
USABLE INK (g)
3.0
2.8
2.6
2.4
2.2
2.0
1.8
1.6
1.4
1.2
1.0
0.8
0.6
0.4
0.2
0.0
0.00
0.10
0.20
0.30
0.40
CARTRIDGE DENSITY (g/cc)

4SW (3.4% LUBE)
ROUND (1% LUBE)
6.5
6.0
5.5
5.0
4.5
4.0
3.5
3.0
2.5
2.0
RATIO
USABLE INK (gms)
/FIBER
WEIGHT (gms)
0
0.1
0.2
0.3
0.4
CARTRIDGE DENSITY (g/cc)

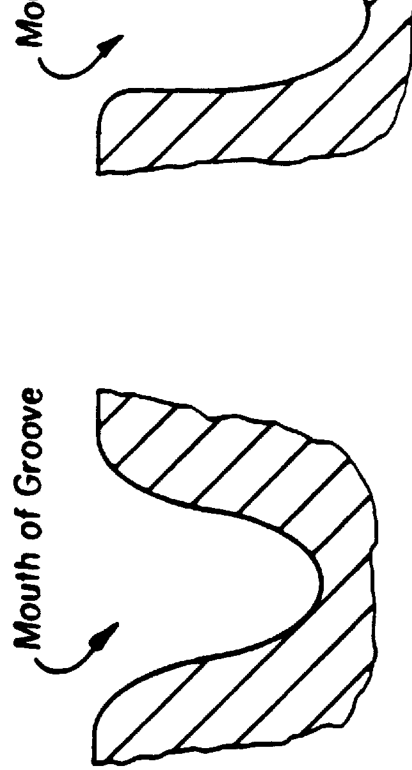
Fig. 31 A
Fig. 31 B
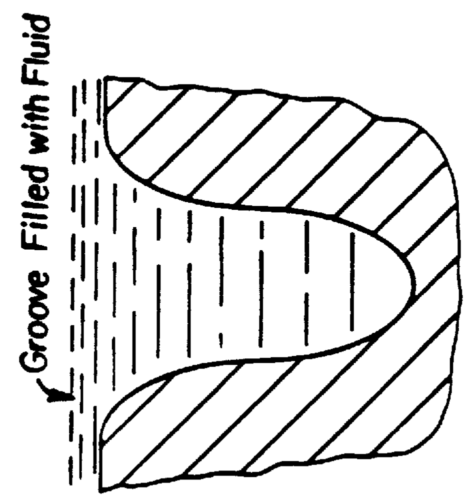
Fig. 31 C
Mouth of Groove
Fig. 32 A
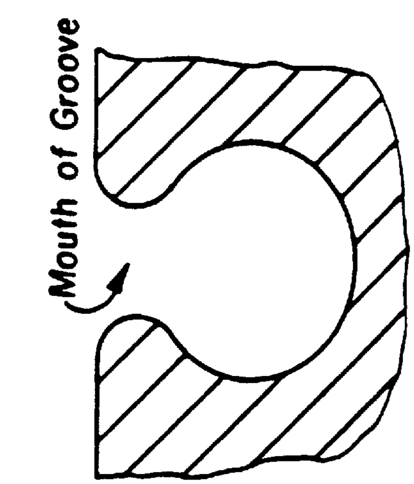
Fig. 32 B
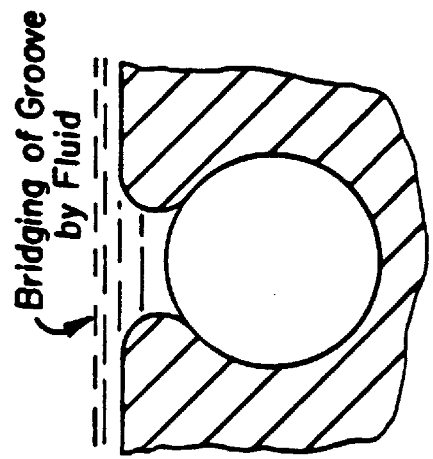
Fig. 32 C

100 W
50 W
5 W
10 W
10 W

.336
.168
.341
.690
.063R 1.3W
75W
150W
30W
5W
60W
50W
.5531
5.393
4.909
4.771
.870
.580
.290
.290
.580
.870
5.047
5.393
5.185
5.531
5.531
5.670
5.669
6.084
6.084

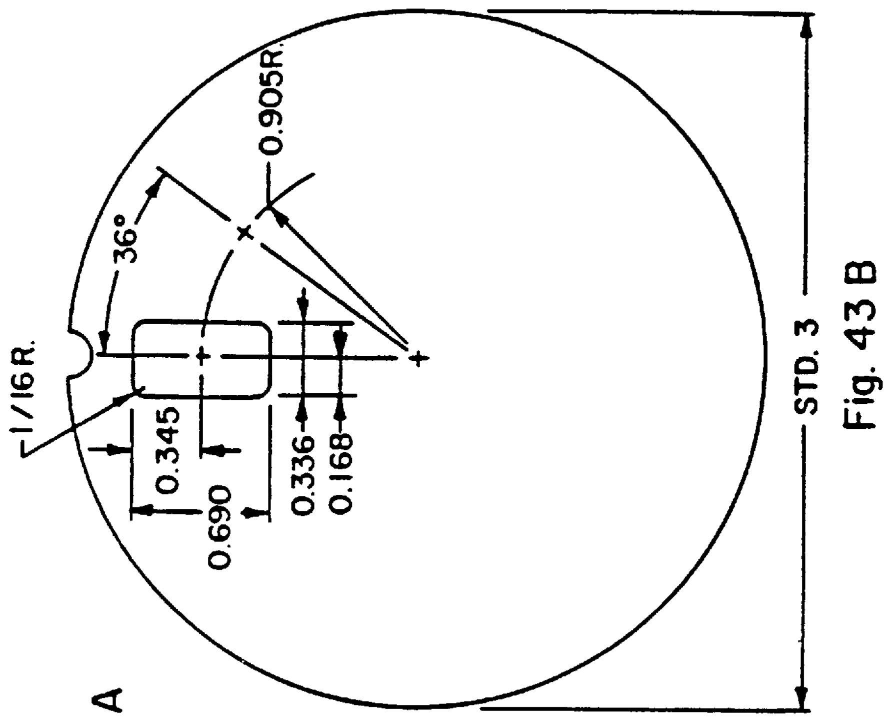
Fig. 43 B
Fig. 43 A
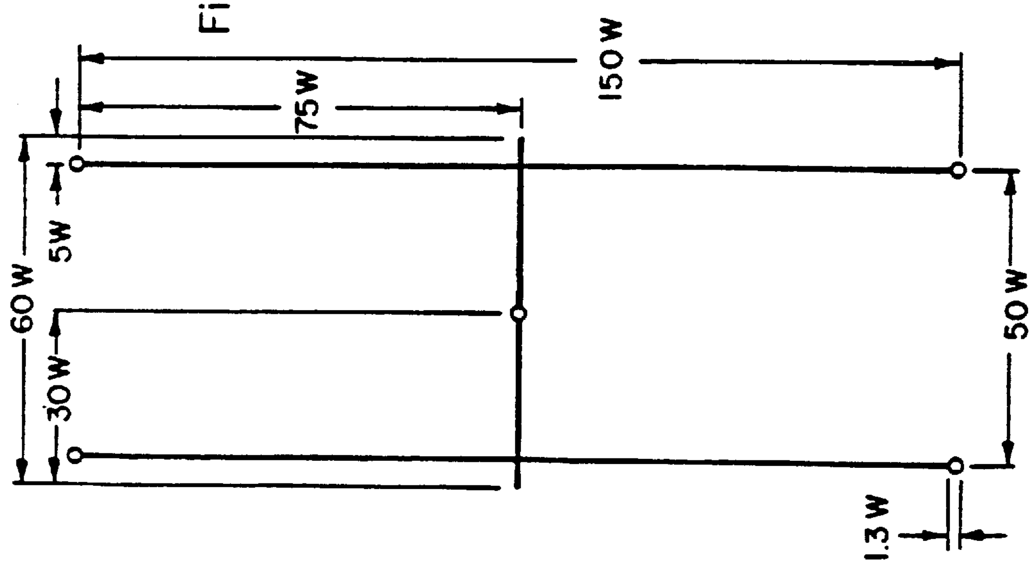

PROCESS FOR SPONTANEOULY TRANSPORTING A FLUID

This is a divisional application of application Ser. No. 08/133,426, filed Oct. 8, 1993, now U.S. Pat. No. 5,611,981, which is a divisional application of Ser. No. 07/736,267, filed Jul. 23, 1991, which is a continuation-in-part application of Ser. No. 07/333,651, filed Apr. 4, 1989, now abandoned.

FIELD OF THE INVENTION

This invention concerns fibers that are capable of spontaneously transporting water on their surfaces and useful structures made from such fibers.

BACKGROUND OF THE INVENTION

Presently available absorbant articles such as diapers, sanitary napkins, incontinence briefs, and the like are generally very good at absorbing aqueous fluids such as urine and blood. However, during typical use such articles become saturated at the impingement zone while other zones removed from the impingement zone will remain dry. As a result, a substantial portion of the total absorbant capabilities of such articles remains unused. Thus, it would be highly desirable to have a means for transporting the aqueous fluids from the impingement zone to other areas of the absorbent article to more fully utilize the article's total absorbant capability. We have discovered such a means by the use of certain fibers that are capable of transporting aqueous fluids on their surfaces.

Liquid transport behavior phenomena in single fibers has been studied to a limited extent in the prior art (see, for example, A. M. Schwartz & F. W. Minor, *J. Coll. Sci.*, 14, 572 (1959)).

There are several factors which influence the flow of liquids in fibrous structures. The geometry of the pore-structure in the fabrics (capillarity), the nature of the solid surface (surface free energy, contact angle), the geometry of the solid surface (surface roughness, grooves, etc.), the chemical/physical treatment of the solid surface (caustic hydrolysis, plasma treatment, grafting, application of hydrophobic/hydrophilic finishes), and the chemical nature of the fluid all can influence liquid transport phenomena in fibrous structures.

The ability to transport liquids (alternately referred to herein as "wickability") and to hold liquids are two important features of absorbant cores of sanitary consumer disposables such as diapers, adult incontinent products, and feminine hygiene products. Absorbant cores are designed to wick fluids as far as possible to prevent leakage and optimize the use of absorbant material. In a conventional diaper, fluid is wicked by capillary action through the porous fluff pulp core. Liquid holding capacity is largely within the pores of the fluff pulp but is also enhanced by the addition of superabsorbant polymers to the absorbant core. These superabsorbant polymers are especially beneficial for holding liquids under pressure compared to pulp alone. Absorbant cores of diapers and adult incontinent products do not sufficiently wick fluids from the crotch area to entirely prevent leaking. Typically 3–7% of diapers, approximately 30% of feminine napkins, and 33–40% of adult incontinent products leak. Leaking is the number one customer complaint about these products. Solving the leaking problem is high priority among the manufacturers of these products.

In the prior art thermally bonded webs composed of polyester, polypropylene, or polyethylene hydrophobic fibers are formed. These webs are subsequently coated with acrylic acid partially neutralized by alkali metallic salts and crosslinked simultaneously with polymerization to form webs coated in situ with superabsorbant polymer (European Patent Application 0 223 908). The webs have increased absorption of fluid when used in a sanitary product such as a diaper, but the individual fibers of the web do not possess the ability to wick fluid from the crotch area (which is most prone to leaking) to lesser utilized areas of the absorbant core.

French Patent 955,625, Paul Chevalier, "Improvements in Spinning Artificial Fiber", published Jan. 16, 1950, discloses fibers of synthetic origin with alleged improved capillarity. The fibers are said to have continuous or discontinuous grooves positioned in the longitudinal direction.

Japanese Patent Laid-Open No. 204,975/1984 describes the coating of cellulose fiber based material with a water soluble monomer which is converted into a water-absorptive polymer. According to U.S. Pat. No. 4,721,647 this type of material has poor absorption performance because the monomer is able to penetrate inside the fiber base material and fill the capillaries between filaments. The mode of wicking in this prior art is totally in the capillaries between the fibers. The diameter of the capillaries is reduced by the coating. As the coating swells in the wet state the capillaries are blocked off.

Also, the art discloses various H-shapes as follows:

U.S. Pat. No. 3,121,040 entitled "Unoriented Polyolefin Filaments" dated Feb. 11, 1964;

U.S. Pat. No. 3,650,659 entitled "Spinning Die" dated Mar. 21, 1972;

U.S. Pat. No. 870,280 entitled "High Bulk Filamentary Material" dated Jun. 14, 1961;

U.S. Pat. No. 4,179,259 entitled "Spinneret for the Production of Wool-like Man-Made Filament" dated Dec. 18, 1979;

U.S. Pat. No. 3,249,669 entitled "Process for Making Composite Polyester Filaments" dated Mar. 16, 1964;

U.S. Pat. No. 3,623,939 entitled "Crimped Synthetic Filament Having Special Cross-Sectional Profile" dated Jun. 28, 1968;

U.S. Pat. No. 3,156,607 entitled "Lobed Filament" dated Nov. 10, 1964;

U.S. Pat. No. 3,109,195 entitled "Spinneret Plate" dated Nov. 5, 1963;

U.S. Pat. No. 3,383,276 entitled "Extruded Synthetic Filament" dated Mar. 10, 1964;

Netherlands Abstract OCTROO1N°8490, Aunvrage No. 18049, dated Nov. 28, 1922.

U.S. Pat. No. 4,707,409 entitled "Spinneret Orifices and Four-Wing Filament Cross-Sections Therefrom" dated Nov. 17, 1987, assigned to Eastman Kodak Company, describes a spinneret having an orifice defined by two intersecting slots. Each intersection slot is turn defined by three quadrilateral sections connected in series.

Further, PCT International Publication No. WO90/12/30, published on Oct. 18, 1990, entitled "Fibers Capable of Spontaneously Transporting Fluids" by Phillips et al. discloses fibers that are capable of spontaneously transporting water on their surfaces and useful structures made from such fibers.

Also, conventional crimping of fibers is done mechanically with a stuffer box crimper. This method can damage or distort the cross-section of the fibers of this invention. This distortion of the cross-section reduces the ability of the fiber to move and hold fluids.

There are various methods of helically crimping a fiber in the art. For example, U.S. patent application Ser. No. 07/333,651 filed Apr. 4, 1989 describes crimped staple fibers and the process for making the fibers. U.S. Pat. No. 3,050,821 describes a high bulk textile material after a relaxing treatment. U.S. Pat. No. 3,681,188 describes a poly (trimethylene terephthalate) textile fiber in a helical crimp form. U.S. Pat. No. 3,584,103 describes a process for making a helically crimped poly(trimethylene terephthalate) fiber with asymmetric birefringical across the diameter of the filament. U.S. Pat. No. 3,623,939 discloses a crimped synthetic filament. The H-shaped cross-section of the fiber is shown.

We have discovered fibers that have a unique combination of properties that allows for spontaneous transport of aqueous fluids such as water on their surfaces. Heretofore, fibers capable of spontaneously transporting aqueous fluids such as water have been unknown. These fibers can be coated with superabsorbing polymers which are capable of absorbing liquid as well as transporting liquid. Even more preferably, fibers having both a major and minor symmetrical axis are quenched by air where the air stream is perpendicular to the major axis of the fiber.

SUMMARY OF THE INVENTION

The present invention is directed to a synthetic fiber which is capable of spontaneously transporting water on the surface thereof. The fiber satisfies the following equation $$(1-X\cos\theta_a)<0,$$

wherein $\theta_a$ is the advancing contact angle of water measured on a flat film made from the same material as the fiber and having the same surface treatment, if any, X is a shape factor of the fiber cross-section that satisfies the following equation $$X=\frac{P_w}{4r+(\pi-2)D}$$

wherein $P_w$ is the wetted perimeter of the fiber, r is the radius of the circumscribed circle circumscribing the fiber cross-section and D is the minor axis dimension across the fiber cross-section.

The present invention also provides a synthetic fiber which is capable of spontaneously transporting water on the surface thereof wherein said fiber satisfies the equation $$(1-X\cos\theta_a)<-0.7,$$

wherein $\theta_a$ is the advancing contact angle of water measured on a flat film made from the same material as the fiber and having the same surface treatment, if any, X is a shape factor of the fiber cross-section that satisfies the following equation $$X=\frac{P_w}{4r+(\pi-2)D}$$

wherein $P_w$ is the wetted perimeter of the fiber, r is the radius of the circumscribed circle circumscribing the fiber cross-section and D is the minor axis dimension across the fiber cross-section.

The present invention also further provides a synthetic fiber which is capable of spontaneously transporting water on the surface thereof wherein said fiber satisfies the equation $$(1-X\cos\theta_a)<0,$$

wherein $\theta_a$ is the advancing contact angle of water measured on a flat film made from the same material as the fiber and having the same surface treatment, if any, X is a shape factor of the fiber cross-section that satisfies the following equation $$X=\frac{P_w}{4r+(\pi-2)D}$$

wherein $P_w$ is the wetted perimeter of the fiber and r is the radius of the circumscribed circle circumscribing the fiber cross-section and D is the minor axis dimension across the fiber cross-section, and wherein the uphill flux value of said fiber is from about 2 to about 60 cc/g/hr when measured from a reservoir of synthetic urine test fluid along a 20 cm long ramp to an absorbant on an attached platform at 10 cm height.

The present invention even further provides a synthetic fiber which is capable of spontaneously transporting water on the surface thereof wherein said fiber satisfies the equation $$(1-X\cos\theta_a)<0,$$

wherein $\theta_a$ is the advancing contact angle of water measured on a flat film made from the same material as the fiber and having the same surface treatment, if any, X is a shape factor of the fiber cross-section that satisfies the following equation $$X=\frac{P_w}{4r+(\pi-2)D}$$

wherein $P_w$ is the wetted perimeter of the fiber, r is the radius of the circumscribed circle circumscribing the fiber cross-section and D is the minor axis dimension across the fiber cross-section, with the proviso that the fiber is not an X-shaped or an H-shaped fiber having a $\theta_a$ of about 22 degrees, cos $\theta_a$ of about 0.9, and an X factor of about 1.8.

It is preferred that $$\gamma_{LA}\cdot\frac{12\pi\cdot10^{-4}}{\sqrt{\rho}}\cdot\sqrt{dpf}\cdot(1-X\cos\theta_a)\leqq-0.3,$$

wherein $\gamma_{LA}$ is the surface tension of water in air in dynes/cm, ρ is the fiber density in grams/cc, and dpf is the denier of the single fiber.

It is preferred that X is greater than 1.2, preferably between about 1.2 and about 5, most preferably between about 1.5 and about 3. It is preferred that the fiber have an uphill flux value of about 2 to about 60 cc/g/hr.

It is also preferred that the fiber is helically crimped which is obtained by quenching in air which is flowing perpendicular to the major axis of the fiber.

Further, it is preferred that the fiber has a hydrophilic lubricant coated on the surface thereof.

BRIEF DESCRIPTION OF THE DRAWINGS

FIG. 1A—illustration of the behavior of a drop of an aqueous fluid on a conventional fiber that is not spontaneously transportable after the ellipsoidal shape forms (t=0). Angle θ illustrates a typical contact angle of a drop of liquid on a fiber. The arrows labelled "LFA" indicate the location of the liquid-fiber-air interface.

FIG. 1B—illustration of the behavior of a drop of an aqueous fluid on a conventional fiber that is not spontaneously transportable at time=$t_1$ ($t_1$>0). The angle θ remains the same as in FIG. 1A. The arrows labelled "LFA" indicate the location of the liquid-fiber-air interface.

FIG. 1C—illustration of the behavior of a drop of an aqueous fluid on a conventional fiber that is not spontaneously surface transportable at time=$t_2$ ($t_2$>$t_1$). The angle θ remains the same as in FIG. 1A. The arrows labelled "LFA" indicate the location of the liquid-fiber-air interface.

FIG. 2A—illustration of the behavior of a drop of an aqueous fluid which has just contacted a fiber that is spontaneously transportable at time=0. The arrows labelled "LFA" indicate the location of the liquid-fiber-air interface.

FIG. 2B—illustration of the behavior of a drop of an aqueous fluid on a fiber that is spontaneously transportable at time=$t_1$ ($t_1$>0). The arrows labelled "LFA" indicate the location of the liquid-fiber-air interface.

FIG. 2C—illustration of the behavior of a drop of an aqueous fluid on a fiber that is spontaneously transportable at time=$t_2$ ($t_2$>$t_1$). The arrows labelled "LFA" indicate the location of the liquid-fiber-air interface.

FIG. 6B—schematic representation of an orifice of a spinneret useful for producing a spontaneously transportable fiber.

FIG. 17B—schematic representation of a poly(ethylene terephthalate) fiber cross-section made using a spinneret having an orifice as illustrated in FIG. 6B (specific dimensions of spinneret orifice described in Example 13).

FIG. 18A—a schematic representation of the top view of a diaper.

FIG. 18B—a schematic representation of an exploded side view of a diaper along section 1B of the major axis of the diaper.

FIG. 23A—a schematic representation of the top view of a diaper. The lines in the cut-away view represent tow made from fibers of the present invention which are substantially parallel and running essentially the entire length of the diaper.

FIG. 23B—a schematic representation of the top view of a diaper. The lines in the cut-away view represent tow made from fibers of the present invention which are substantially parallel and extending more than half the length of the diaper.

FIG. 31A—a schematic representation of a desirable groove in a fiber cross-section.

FIG. 31B—a schematic representation of a desirable groove in a fiber cross-section.

FIG. 31C—a schematic representation of a desirable groove in a fiber cross-section illustrating the groove completely filled with fluid.

FIG. 32A—a schematic representation of a groove where bridging is possible in the fiber cross-section.

FIG. 32B—a schematic representation of a groove where bridging is possible in the fiber cross-section.

FIG. 32C—a schematic representation of a groove illustrating bridging of the groove by a fluid.

FIGS. 43A and 43B—schematic representations of Spinneret I1039 wherein the spinneret holes are oriented in a radial pattern on the face of the spinneret. All dimensions are in units of inches except those containing the letter "W".

FIGS. 48A, 48B and 48C—schematic representations of Spinneret 1047 wherein spinneret holes are oriented such that the cross-flow quench air was directed toward one side of the H.

FIG. 50—a photomicrograph of stuffer box crimped fiber having a distorted cross-section.

FIG. 53—a photomicrograph of a helically crimped fiber prepared by the process of the invention.

DETAILED DESCRIPTION OF THE INVENTION

Figure 3:
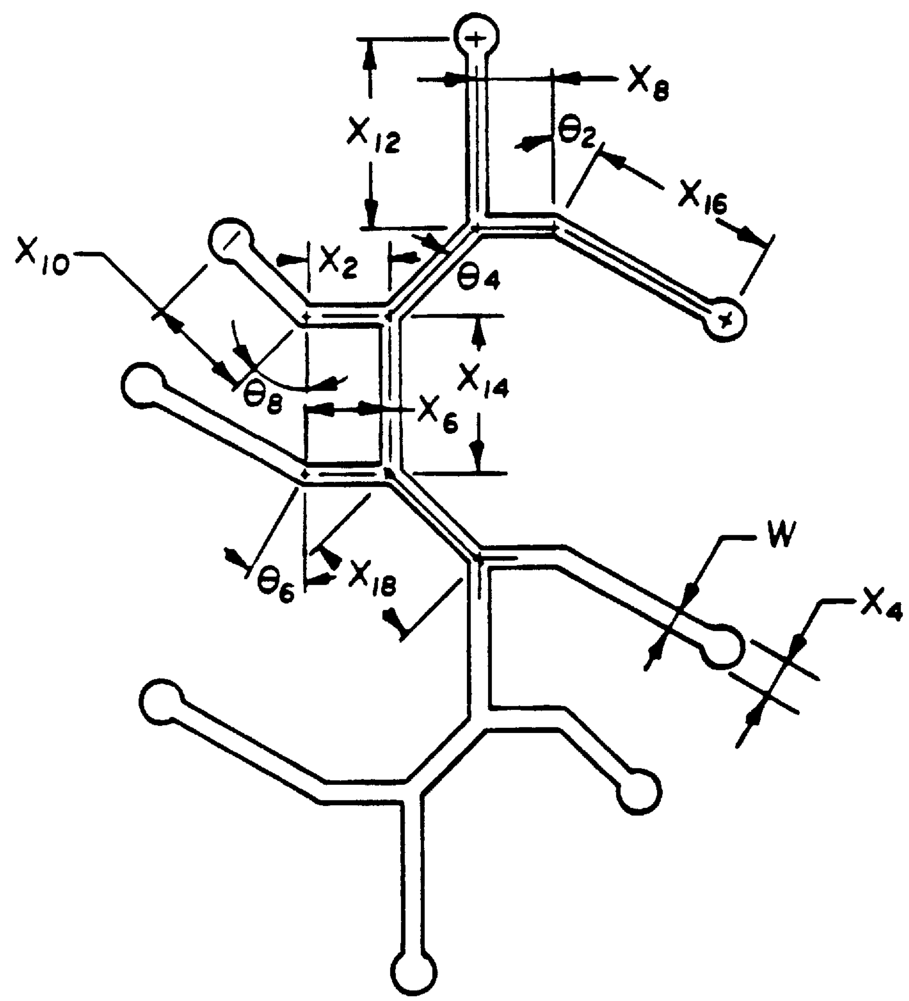
FIG. 3—schematic representation of an orifice of a spinneret useful for producing a spontaneously transportable fiber.

As used herein, the term "base fibers" means the fibers disclosed in Ser. No. 333,651 not having a superabsorbant polymer coating (but optionally having a different surface treatment, e.g., a coating of a hydrophilic lubricant), and the terms "coated fiber", "absorbent fiber", or "coated, absorbant fiber" mean a fiber of the present invention, i.e., a base fiber having coated thereon at least one superabsorbant polymer.

The three important variables fundamental to the liquid transport behavior are (a) surface tension of the liquid, (b) wettability or the contact angle of the liquid with the solid, and (c) the geometry of the solid surface. Typically, the wettability of a solid surface by a liquid can be characterized by the contact angle that the liquid surface (gas-liquid interface) makes with the solid surface (gas-solid surface). Typically, a drop of liquid placed on a solid surface makes a contact angle, θ, with the solid surface, as seen in FIG. 1A.

If this contact angle is less than 90°, then the solid is considered to be wet by the liquid. However, if the contact angle is greater than 90°, such as with water on Teflon® surface, the solid is not wet by the liquid. Thus, it is desired to have a minimum contact angle for enhanced wetting, but definitely, it must be less than 90°. However, the contact angle also depends on surface inhomogeneities (chemical and physical, such as roughness), contamination, chemical/physical treatment of the solid surface, as well as the nature of the liquid surface and its contamination. Surface free energy of the solid also influences the wetting behavior. The lower the surface energy of the solid, the more difficult it is to wet the solid by liquids having high surface tension. Thus, for example, Teflon, which has low surface energy does not wet with water. (Contact angle for Teflon-water system is 112°.) However, it is possible to treat the surface of Teflon with a monomolecular film of protein, which significantly enhances the wetting behavior. Thus, it is possible to modify the surface energy of fiber surfaces by appropriate lubricants/finishes to enhance liquid transport. The contact angle of polyethylene terephthalate (PET), Nylon 66, and polypropylene with water is 80°, 71°, and 108°, respectively. Thus, Nylon 66 is more wettable than PET. However, for polypropylene, the contact angle is >90°, and thus polypropylene is nonwettable with water.

The second property of fundamental importance to the phenomena of liquid transport is surface tension of the liquid.

The third property of fundamental importance to the phenomena of liquid transport is the geometry of the solid surface. Although it is known that grooves enhance fluid transport in general, we have discovered particular geometries and arrangements of deep and narrow grooves on fibers and treatments thereof which allow for the spontaneous surface transport of aqueous fluids in single fibers. Thus we have discovered fibers with a combination of properties wherein an individual fiber is capable of spontaneously transporting water on its surface.

Geometry of the fiber surface and application of a hydrophilic lubricant are very important. Also, the particular geometry of the deep and narrow grooves is very important. For example, as shown in FIGS. 31A, 31B and 31C, grooves which have the feature that the width of the groove at any depth is equal to or less than the width of the groove at the mouth of the groove are preferred over those grooves which do not meet this criterion (e.g., grooves as shown in FIGS. 32A, 32B and 32C). If the preferred groove is not achieved, "bridging" of the liquid across the restriction is possible and thereby the effective wetted perimeter (Pw) is reduced. Accordingly, it is preferred that Pw is substantially equal to the geometric perimeter.

The number of continuous grooves present in the fiber of the present invention is not critical as long as the required geometry is present (i.e., the fiber satisfies the equation $(1-X \cos \theta_a)<-0.7$); or $(1-X \cos \theta_a)<0$) with the proviso that the fiber is not an X-shaped or an H-shaped fiber having a $\theta_a$ of about 22 degrees, $\cos \theta_a$ of about 0.9, and an X factor of about 1.8; or $(1-X \cos \theta_a)<0$ wherein the uphill flux value of said fiber is from about 2 to about 60 cc/g/hr when measured from a reservoir of synthetic urine test fluid along a 20 cm long ramp to an absorbant on an attached platform at 10 cm height. The term "about" is defined for the purposes of this equation as being within plus or minus 5% experimental error. Typically there are at least 2 grooves present, and preferably less than 10.

"Spontaneously transportable" and derivative terms thereof refer to the behavior of a fluid in general and in particular of a drop of fluid, typically water, when it is brought into contact with a single fiber such that the drop spreads along the fiber. Such behavior is contrasted with the normal behavior of the drop which forms a static ellipsoidal shape with a unique contact angle at the intersection of the liquid and the solid fiber. It is obvious that the formation of the ellipsoidal drop takes a very short time but remains stationary thereafter. FIGS. 1A–1C and 2A–2C illustrate the fundamental difference in these two behaviors. Particularly, FIGS. 2A, 2B, and 2C illustrate spontaneous fluid transport on a fiber surface. The key factor is the movement of the location of the air, liquid, solid interface with time. If such interface moves just after contact of the liquid with the fiber, then the fiber is spontaneously transportable; if such interface is stationary, the fiber is not spontaneously transportable. The spontaneously transportable phenomenon is easily visible to the naked eye for large filaments (>20 denier per filament (dpf)) but a microscope may be necessary to view the fibers if they are less than 20 dpf. Colored fluids are more easily seen but the spontaneously transportable phenomenon is not dependent on the color. It is possible to have sections of the circumference of the fiber on which the fluid moves faster than other sections. In such case the air, liquid, solid interface actually extends over a length of the fiber. Thus, such fibers are also spontaneously transportable in that the air, liquid, solid interface is moving as opposed to stationary.

Spontaneous transportability is basically a surface phenomenon; that is the movement of the fluid occurs on the surface of the fiber. However, it is possible and may in some cases be desirable to have the spontaneously transportable phenomenon occur in conjunction with absorption of the fluid into the fiber. The behavior visible to the naked eye will depend on the relative rate of absorption vs. spontaneous transportability. For example, if the relative rate of absorption is large such that most of the fluid is absorbed into the fiber, the liquid drop will disappear with very little movement of the air, liquid, solid interface along the fiber surface whereas if the rate of absorption is small compared to the rate of spontaneous transportability the observed behavior will be like that depicted in FIGS. 2A through 2C. In FIG. 2A, a drop of aqueous fluid is just placed on the fiber (time=0). In FIG. 2B, a time interval has elapsed (time=$t_1$) and the fluid starts to be spontaneously transported. In FIG. 2C, a second time interval has passed (time=$t_2$) and the fluid has been spontaneously transported along the fiber surface further than at time=$t_1$.

The fibers of the invention preferably have excellent uphill flux. Uphill flux is an index of the rate of transport of a fluid and is determined by the methodology described in Example 21 hereof. Uphill flux is related to adhesion tension. Adhesion tension is the product of the surface tension $\gamma$ and $\cos \theta_a$. We have surprisingly found that the type of fiber surface treatment can have a substantial impact on the effective adhesion tension (and therefore on the uphill flux). That is, we have found that certain surface treatments have the undesirable feature of reducing the effective surface tension of aqueous fluids (e.g., urine) such that it is substantially reduced from its theoretical potential. Thus, preferred surface treatments are those which result in the effective adhesion tension of the fluid to be transported being as close to the theoretical adhesion tension as possible. The effective adhesion tension is measured by the method described in Example 22 hereof using the appropriate fluid. Preferred fibers of the invention have an effective adhesion tension in water of greater than 38 dynes/cm. More preferred is greater than 45 dynes/cm. Plasma treatment is a preferred surface treatment since the effective adhesion tension is close to the theoretical adhesion tension.

It is not desired to be bound by any particular theory or mechanism. However, it is believed that for some surface treatments, such as use of potassium lauryl phosphate and/or PEG 600 monolaurate, a portion of the deposited surface treatment material partially solubilizes in the fluid, at least at the fluid/surface interface, substantially reducing the surface tension of the liquid, thereby reducing the effective adhesion tension but not substantially affecting the contact angle ($\theta_a$).

It has also been discovered that for a given vertical distance and linear distance to move the fluid, a given channel depth and a given adhesion tension, there is an optimum channel width which maximizes the uphill flux of the liquid being transported.

Figure 40:
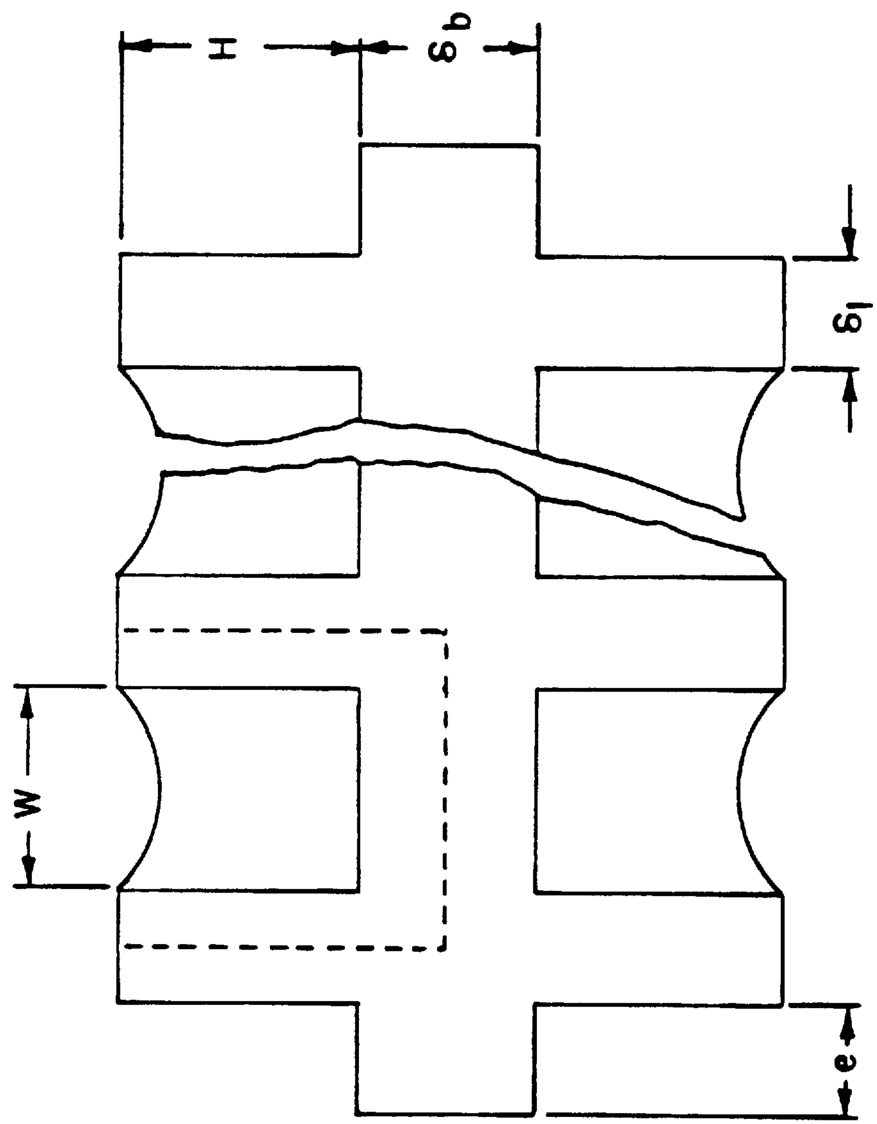
FIG. 40—a schematic representation depicting a unit cell.

A fiber of the invention can be characterized as having one or more "channels" or "unit cells". For example, the fiber cross-section shown in FIG. 40 depicts a unit cell. A unit cell is the smallest effective transporting unit contained within a fiber. For fibers with all grooves identical, the total fiber is the sum of all unit cells. In FIG. 40 each unit cell has a height, H, and a width, W. $S_l$ is the leg thickness and $S_b$ is the backbone thickness. In addition to the specific dimensions of W and H, the other dimensional parameters of the cross-section are important for obtaining the desired type of spontaneous transportability. For example, it has been found that the number of channels and the thickness of the areas between unit cells, among other things, are important for optimizing the uphill flux value of the fiber. For obtaining a fiber cross-section of desirable or optimal fluid movement properties the following equations are useful:

$$q = \frac{W^2}{K\mu M_f} \cdot \frac{1}{l}\left(\alpha\gamma p\cos\theta - \beta\gamma\omega - \frac{\rho g h}{g_c} A\right) \times 3600$$

$$M_f = \rho_f A_f L_f;\ K = 12$$

$$A_f = \frac{1}{n}\left\{\left[(2H+S_b)\frac{S_l}{2} + W\frac{S_b}{2}\right]n + 2\left[(2H+S_b)\frac{S_l}{2} + e\cdot S_b\right]\right\}$$

$$p = 2H + W$$

$$\omega = \frac{\pi(90-\theta)}{180\sin(90-\theta)} \cdot W$$

$$h = l\sin\phi$$

$$A = H\cdot W - \frac{W^2}{4\sin(90-\theta)}\left[\frac{\pi(90-\theta)}{180\sin(90-\theta)} - \cos(90-\theta)\right]$$

$$dpf = \rho_f A_f \cdot n \cdot (9000)(100)$$

wherein:

q=flux ($cm^3$/hr-gm)
W=channel width (cm)
$\mu$=fluid viscosity (gm/cm-sec)
$M_f$=fiber mass per channel (gm)
$\rho_f$=fiber density (gm/$cm^3$)
$A_f$=fiber cross-sectional area per channel ($cm^2$)
$L_f$=total fiber length (cm)
l=distance front has advanced along fiber (cm)
$\alpha$=adhesion tension correction factor (surface) (d'less)
$\gamma$=fluid surface tension (dynes/cm-gm/$sec^2$)
p=wetted channel perimeter (cm)
H=channel depth (cm)
$\theta$=contact angle (degrees)
$\beta$=adhesion tension correction factor (bulk) (d'less)
K=constant (d'less)
$\omega$=arc length along meniscus (cm)
$\rho$=fluid density (gm/$cm^3$)
g=acceleration of gravity (cm/$sec^2$)
h=vertical distance (cm)
$g_c$=gravitational constant (d' less)
A=fluid cross-sectional area per channel ($cm^2$)
n=number of channels (d'less)
$S_b$=fiber body or backbone thickness (cm)
$S_l$=fiber leg thickness (cm)
e=backbone extension (cm)
$\phi$=fiber horizontal inclination angle (degrees)
dpf=denier per filament (gm/9000 m)

The equation for q is useful for predicting flux for a channeled fiber horizontally inclined at an angle $\phi$. This equation contains all the important variables related to fiber geometry, fiber physical properties, physical properties of the fluid being transported, the effects of gravity, and surface properties related to the three-way interaction of the surfactant, the material from which the fiber is made, and the transported fluid. The equations for $M_f$, $A_f$, p, $\omega$, h, and A can be substituted into the equation for q to obtain a single functional equation containing all the important system variables, or, for mathematical calculations, the equations can be used individually to calculate the necessary quantities for flux prediction.

The equation for q (including the additional equations mentioned above) is particularly useful for determining the optimum channel width to maximize uphill flux (fluid movement against the adverse effects of gravity; sin $\phi$>0 in the equation for h). The equation for q is also useful for calculating values for downhill flux (fluid movement enhanced by gravity; sin $\phi$<0 in the equation for h) for which there is no optimum channel width. Obviously, horizontal flux can also be calculated (no gravity effects; sin $\phi$=0). The equation for q and the equations for p, A, and $A_f$ were derived for a fiber containing one or more rectangularly-shaped channels, but the basic principles used to derive these equations could be applied to channels having a wide variety of geometries.

A fiber of the present invention is capable of spontaneously transporting water on the surface thereof. Distilled water can be employed to test the spontaneous transportability phenomenon. However, it is often desirable to incorporate a minor amount of a colorant into the water to better visualize the spontaneous transport of the water, so long as the water with colorant behaves substantially the same as pure water under test conditions. We have found aqueous Syltint Poly Red® from Milliken Chemicals to be a useful solution to test the spontaneous transportability phenomenon. The Syltint Poly Red® solution can be used undiluted or diluted significantly, e.g., up to about 50× with water.

In addition to being capable of transporting water, a fiber of the present invention is also capable of spontaneously transporting a multitude of other aqueous fluids. Aqueous fluids are those fluids comprising about 50% or more water by weight, preferred is about 75% or more water by weight, most preferred is about 90% or more water by weight. Preferred aqueous fluids are body fluids, especially human body fluids. Such preferred fluids include, but are not limited to, blood, urine, perspiration, and the like. Other preferred aqueous fluids include, for example, aqueous inks.

In addition to being able to transport aqueous fluids, a fiber of the present invention is also capable of transporting an alcoholic fluid on its surface. Alcoholic fluids are those fluids comprising greater than about 50% by weight of an alcoholic compound of the formula

R—OH wherein R is an aliphatic or aromatic group containing up to 12 carbon atoms. It is preferred that R is an alkyl group of 1 to 6 carbon atoms, more preferred is 1 to 4 carbon atoms. Examples of alcohols include methanol, ethanol, n-propanol and isopropanol. Preferred alcoholic fluids comprise about 70% or more by weight of a suitable alcohol. Preferred alcoholic fluids include antimicrobial agents, such as disinfectants, and alcohol-based inks.

The superabsorbant coating of the coated fiber of the present invention acts as a "sink" and absorbs whatever fluid is being transported.

The absorbant fibers of the present invention are coated with at least one superabsorbant material. By the word "coated" and derivative terms thereof is meant that the superabsorbant material is in a continuous phase and completely surrounds the circumference of a fiber cross-section for at least a portion of the fiber length. Different embodiments of the coating include wherein the entire fiber is substantially coated and wherein the fiber is only intermittently coated. This intermittent coating provides segments which will transport fluid without absorbing it to areas which are coated with superabsorbant polymer and which will absorb the fluid in a preferred area. Which specific embodiment is preferred will depend upon the particular desired application. A particular preferred embodiment is wherein the fiber of the present invention is substantially the length of an absorbant article (e.g., a diaper, an incontinent pad, or the like) and is coated on the ends of the fiber, but not in the center portion.

Also, in the coated fibers of the invention, the coating is in intimate contact with at least a portion of the fiber surface. Preferably, substantially the entire coating which is positioned adjacent to the fiber surface is in intimate contact with that portion of the fiber surface. That is, preferably all the groove surfaces are "filled" and no visible gaps appear between the coating and the fiber surface upon routine examination by microscopy at a magnification of about 20×.

Water soluble polymerizable monomers such as acrylic acid, methacrylic acid, and vinylsulfonic acid of which 20% or more of the carboxyl groups have been neutralized into an alkali metal salt can be used to form the superabsorbant coating on the base fibers. Preferred superabsorbant polymers are those formed which have a crosslinked structure. Water soluble crosslinking agents having two or more functional groups capable of reacting with a functional group of the aforementioned acids can be used. They are well known in the art. N,N'-methylene bisacrylamide, ethylene glycol bisacrylate, and polyglycidyl ethers are typical examples. The polymerization is carried out in situ, i.e., in the presence of the base fibers. The polymerization can be accomplished through thermal, light, accelerated electron beams, radiation, ultraviolet rays. It is necessary to add a water soluble radical polymerization initiator, in thermal polymerization, or a water-soluble initiator capable of generating radicals with the aid of light or ultraviolet rays in photopolymerization or ultraviolet polymerization to the aqueous monomer solution. Initiators are well known in the art (see U.S. Pat. No. 4,721,647). The degree of crosslinking can be varied to control the amount and rate of absorption to the extent that the superabsorbant polymer remains water insoluble. The amount of superabsorbant polymer coating can be varied. It is preferred that the amount be limited so that individual filaments are not bonded together or that the swollen gel is prevented from leaving the grooves of the filaments.

Generally, the methodology taught in U.S. Pat. No. 4,721,647 (incorporated herein by reference in its entirety) and European Patent Application 0 188 091 can be used to prepare the coated absorbant fibers of the present invention except that one would substitute the spontaneously transportable fibers of Serial No. 333,651, (i.e., the base fibers) for the fiber used in the prior art methods.

A prior art example (European Patent Application 0 188 091) discloses non-woven webs having a thin superabsorbant polymeric coating on the individual fibers of the web. The fibers of this web are round cross-section fibers such as Kodel® 431 polyester (available from Eastman Chemical Products, Inc., Kingsport, Tenn., U.S.A.). The aforementioned disclosure attempts to solve the problem of gel blocking which occurs in some absorbent products where the superabsorbant polymer in granule form is layered within absorbant core. As the superabsorbant polymer granules absorb fluid they swell. Liquid transport through the swollen gel is limited primarily to the slow rates of diffusion. The European Patent Application 0 188 091 attempts to solve this barrier problem of swollen gels by uniformly dispersing the superabsorbant polymer throughout the web as a uniformly thin coated film on the fibers. The claim is that they will not block fluid transport throughout the remainder of the open network structure of the web. The thinly coated fibers of 0 188 091 only absorb fluid in the coating. They do not wick fluid. These webs are dependent on the capillary action of the pores between the fibers for wicking action. The coated fibers, filaments, or webs coated with superabsorbant polymer of this invention unexpectedly both wick and absorb fluid.

The problem of blocking capillary wicking action between superabsorbant coated hydrophilic fiber base materials discussed in U.S. Pat. No. 4,721,647 is not a problem in the present invention since the wicking action does not depend solely on capillary action between filaments. Furthermore, substantial uniform coating of monomer solution is accomplished within the grooves of the base fibers as opposed to outer perimeter and between filaments of the prior art hydrophilic fibers.

Figure 55:
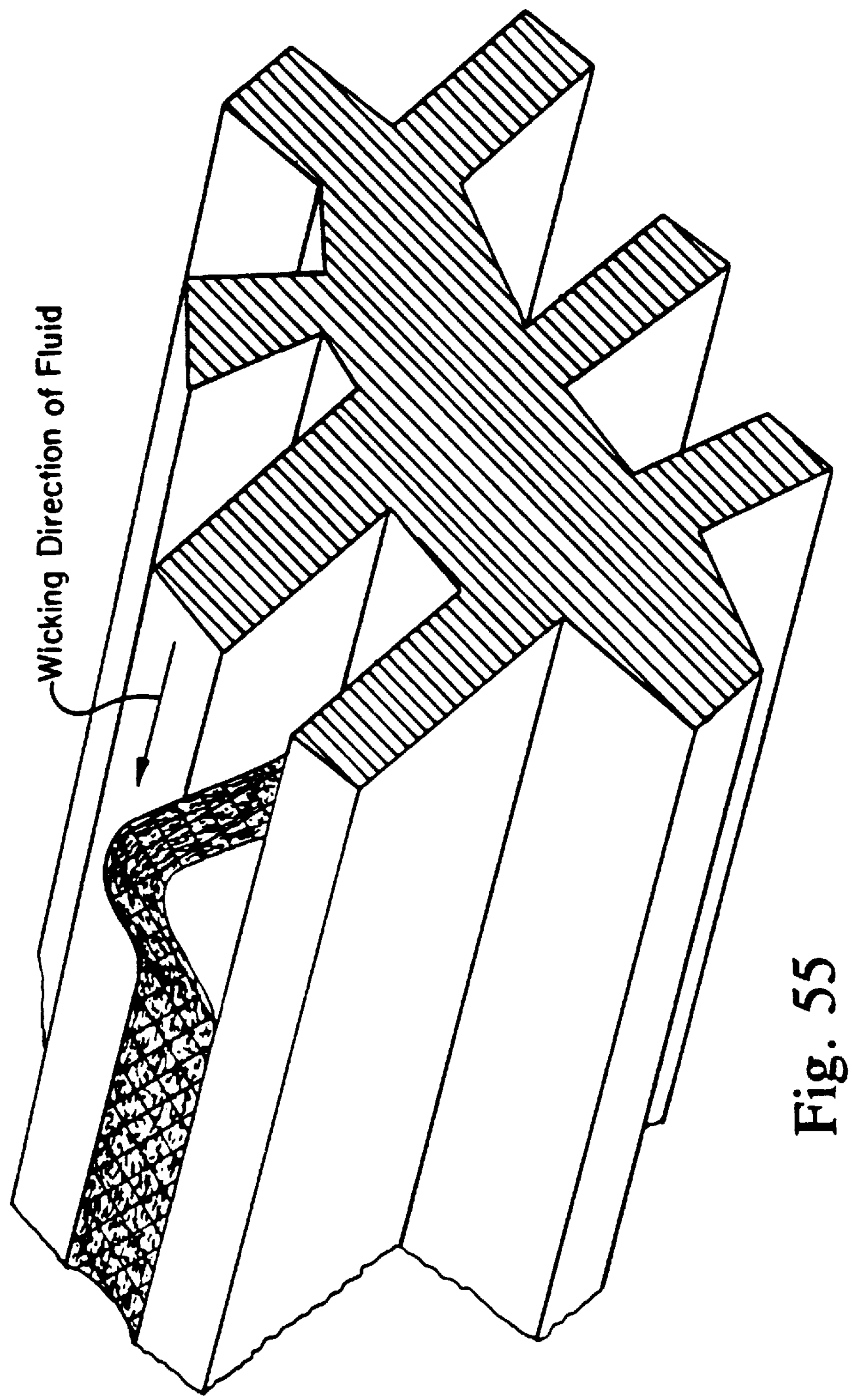
FIG. 55—a schematic representation of a single fiber with one groove filled with superabsorbant polymer.

The liquid transport of the fibers is attributed to having a desired combination of hydrophilic coating and surface geometry. One would expect that coating these fibers with superabsorbant polymer (especially using amounts of polymer which completely fill the grooves of the base fibers) would destroy the preferred geometry of the filament necessary for liquid transport. Unexpectedly when these base fibers which have been coated with superabsorbant polymer are subjected to a fluid such as water or synthetic urine, the super-absorbant polymer filling the grooves is observed to swell as it absorbs fluid. The swollen gel pops out of the grooves sufficient to allow the fluid to wick down the open groove until it contacts additional super-absorbant. The process is repeated continuously until the superabsorbant is consumed or the end of the filament is reached. Although it is not desired to be bound by any particular mechanism, it is believed that the hydrophilic coating initially placed on the base fibers is not destroyed by the superabsorbant polymer coating and the desired geometry of the grooves is restored as the superabsorbant polymer swells and moves out of the grooves. Also it is believed that no bonding occurs between the superabsorbant polymer coating and the fiber surface to hold the gel. A cross-sectional schematic of a single base fiber having a groove filled with superabsorbant polymer is shown in FIG. 55. The superabsorbant polymer is shown as it swells and pops out of the groove. This action allows room for more fluid to enter and wick in the groove.

We have discovered an improved process for helically crimping a fiber having both a major and a minor axis of symmetry, wherein quenching by air occurs perpendicular to the major axis of the fiber. In particular, the process involves the following steps: extruding a conventional PET fiber forming polymer; passing the polymer through spinneret hole shapes; orienting said spinneret hole shapes to the cross-flow quench air so that quenching occurs perpendicular to the major axis of the fiber; controlling the quench air; applying hydrophilic lubricants; taking up the fibers at conventional speeds; drafting the fibers using conventional drafting (single steam stage in steam or two stage in water and steam); adding an additional amount of hydrophilic lubricant; and relaxing the drawn fibers in a heated chamber to develop the helical crimp.

The full development of the helical crimp in the fibers of the present invention is realized by relaxing the fibers in heat. The temperature of the heating step is above the $T_g$ of the fibers. Also, it appears that the helical crimp is formed due to differences in the orientation of the fiber across the diameter of the cross section. This difference in orientation is built into the fiber by following the steps listed in the process previously described. The higher the difference in orientation, the more likely that the filament will form a helical crimp.

It is also preferred that the number of crimps/inch in the fiber is greater than 4 and the crimp amplitude is less than 2 mm.

Particularly preferred hydrophilic lubricants which can be used to lubricate the fibers of this invention include the following:

(1) Lubricant (PM 13430) comprising 49% polyethylene glycol (PEG) 600 monolaurate, polyoxyethylene (13.64) monolaurate, 49% polyethylene glycol (PEG) 400 monolaurate, polyoxyethylene (9.09) monolaurate, and 2% 4-cetyl-4-ethylmorpholinium ethosulfate (antistat);
(2) Hypermer A109 sold by ICI Americas, Inc., which is a modified polyester surfactant;
(3) Milease T sold by ICI Americas, Inc. which is a soil release agent comprising polyester, water, and other ingredients;
(4) Brij 35 sold by ICI Americas, Inc. which is a polyoxyethylene (23) lauryl ether;
(5) Brij 99 sold by ICI Americas, Inc. which is a polyoxyethylene (20) oleyl ether;
(6) G-1300 sold by ICI Americas, Inc. which is a polyoxyethylene glyceride ester, a nonionic surfactant; and
(7) G-1350 sold by ICI Americas, Inc., a polyoxylene-polyoxypropylene sorbitan linoleic phthalic ester.

Among the methods of applying lubricants to the fibers of the invention are those described in U.S. Pat. Nos. 5,234,702 and 5,372,739 and U.S. application Ser. No. 08/339,619 filed Nov. 15, 1994, and incorporated herein by reference.

Accordingly, the present invention is also directed to a process for spontaneously transporting an aqueous fluid (which includes water) or an alcoholic fluid on the surface thereof. Therefore, a process of the present invention can be described as a process for spontaneously transporting an aqueous fluid comprising contacting a fiber of the present invention with an aqueous fluid. Furthermore, another process of the present invention can be described as a process for spontaneously transporting an alcoholic fluid comprising contacting a fiber of the present invention with an alcoholic fluid. Once the aqueous fluid or alcoholic fluid contacts the fiber, said aqueous fluid or alcoholic fluid will be spontaneously transported. In many applications, it is preferred to have a portion of the fiber in contact with a source of the aqueous fluid and a different portion of the fiber in contact with a sink (the term "sink" will be defined hereinafter).

Fibers of this invention have the uniquely desirable feature of spontaneously transporting aqueous or alcoholic fluids on their surfaces. Since all of these fibers have finite length, e.g., a tow in a diaper which starts and stops at the ends of the diaper or a staple fiber of some specified cut length, the ability to move fluid ceases once the fluid reaches the ends of the fibers unless "sinks" for the fluid are provided. Sinks may be, for example, fluff pulp or superabsorbant gels, powders or fibers. Ideally, to maximize the utility of this invention, three key features are desired:

(1) a source of the appropriate fluid to be moved,
(2) the spontaneous surface transport of such fluids which initiates the movement of the fluid and fills the conduits through which the fluid moves after the fiber surface becomes "full" of fluid and the spontaneous driving forces no longer exist, and
(3) a sink or sinks for such fluid which are in intimate contact with the fiber at one or more locations along the length of each individual fiber.

For example, the practical significance of these three features can be seen in a diaper within the scope of the present invention during typical use. The fluid is urine, which is deposited in significant quantities in a reasonably periodic manner. After the first deposit the urine will be transported spontaneously along each fiber until such time as the source ceases to emit urine, the urine is absorbed into an adjacent absorbent layer (for which the urine needs to be in contact with the adjacent absorbent layer for at least about 10 seconds) or the urine contacts a sink. As used herein the term "sink" can be defined as a structure which has a greater affinity for the aqueous fluid than the fiber. Assuming the source of fluid still exists the fiber will act as a conduit to the sink until such time as the source dries up. It is clear that the locations of the sinks need to be removed from the location of the source if significant movement is desired (e.g., the outer area of the diaper).

Properly designed capillary structures of round cross-section filaments can exhibit spontaneous fluid movement. However, the capillary structure depends on the location of the adjacent filaments and if they happen to move or be out of position no fluid movement takes place. A unique feature of the present invention is that the individual filaments spontaneously transport aqueous fluids without the need for adjacent filaments. This allows for many benefits such as for the movement of fluids over a much wider surface area. Usually more than one urination occurs before a diaper is changed. The second urination (source—at the impingement zone) will again be transported through the fiber conduits to appropriate sinks. The spontaneously transportable feature is probably of less significance the second time than the first urination because the conduits are partially or totally full of fluid. However, without the spontaneously transportable feature relatively little fluid movement takes place and the source section of the diaper (i.e., the impingement zone) remains very wet whereas the rest of the diaper remains very dry.

Likewise, the practical significance of these three features can be seen in a catamenial within the scope of the present invention during typical use. U.S. patent application entitled "Absorbent Articles, Especially Catamenials, Having Improved Fluid Directionality, Comfort and Fit" by Hugh A. Thompson, John L. Hammons, et al,; "Fluid Handling Structures for Use in Absorbant Articles", by Hugh A. Thompson, et al, and; "Absorbant Core for Use in Catamenials", by Buenger, Horney, et al, all assigned to Procter and Gamble, Co., all filed on Jul. 23, 1991 and all incorporated herein by reference, describe the use of the fibers of this invention in certain absorbant articles, especially catamenials. Preferably, the fibers of this invention are located in a pad-like structure comprising the fibers. The pad is used in conjunction with an absorbant core, with the core serving as a reservoir for fluids which are transferred from the pad comprising the fibers of this invention into the core.

The fibers of the present invention can be comprised of any material known in the art capable of having a cross-section of the desired geometry and capable of being coated or treated so as to reduce the contact angle to an acceptable level. Preferred materials for use in the present invention are polyesters.

The preferred polyester materials useful in the present invention are polyesters or copolyesters that are well known in the art and can be prepared using standard techniques, such as polymerizing dicarboxylic acids or esters thereof and glycols. The dicarboxylic acid compounds used in the production of polyesters and copolyesters are well known to those skilled in the art and illustratively include terephthalic acid, isophthalic acid, p,p'-diphenyldicarboxylic acid, p,p'-dicarboxydiphenylethane, p,p'-dicarboxydiphenylhexane, p,p'-dicarboxydiphenyl ether, p,p'-dicarboxyphenoxyethane, and the like, and the dialkylesters thereof that contain from 1 to about 5 carbon atoms in the alkyl groups thereof.

Suitable aliphatic glycols for the production of polyesters and copolyesters are the acyclic and alicyclic aliphatic glycols having from 2 to 10 carbon atoms, especially those represented by the general formula $HO(CH_2)_pOH$, wherein p is an integer having a value of from 2 to about 10, such as ethylene glycol, trimethylene glycol, tetramethylene glycol, pentamethylene glycol, decamethylene glycol, and the like.

Other known suitable aliphatic glycols include 1,4-cyclohexanedimethanol, 3-ethyl-1,5-pentanediol, 1,4-xylylene, glycol, 2,2,4,4-tetramethyl-1,3-cyclobutanediol, and the like. One can also have present a hydroxylcarboxyl compound such as 4,-hydroxybenzoic acid, 4-hydroxyethoxybenzoic acid, or any of the other hydroxylcarboxyl compounds known as useful to those skilled in the art.

It is also known that mixtures of the above dicarboxylic acid compounds or mixtures of the aliphatic glycols can be used and that a minor amount of the dicarboxylic acid component, generally up to about 10 mole percent, can be replaced by other acids or modifiers such as adipic acid, sebacic acid, or the esters thereof, or with modifiers that impart improved dyeability to the polymers. In addition one can also include pigments, delusterants or optical brighteners by the known procedures and in the known amounts.

The most preferred polyester for use in preparing the fibers of the present invention is poly(ethylene terephthalate) (PET).

Other materials that can be used to make the fibers of the present invention include polyamides such as a nylon, e.g., nylon 66 or nylon 6; polypropylene; polyethylene; and cellulose esters such as cellulose triacetate or cellulose diacetate.

Other preferred materials useful in preparing the fibers of the present invention include binary blends of cellulose esters with aliphatic polyesters or aliphatic-aromatic copolyesters as well as ternary blends of cellulose esters with aliphatic polyester/polyacrylates, aliphatic polyesters/polyvinyl acetates/aliphatic polyesters/polyvinyl alcohol, aliphatic polyesters/polyvinyl chloride, aliphatic polyesters/polycarbonate, aliphatic polyesters/polyvinyl acetate-polyethylene copolymer, aliphatic polyesters/cellulose ethers, aliphatic polyesters/nylon, aliphatic-aromatic copolyesters/polyacrylates/aliphatic-aromatic copolyesters/polyvinyl acetates, aliphatic-aromatic copolyesters/polyvinyl alcohol, aliphatic-aromatic copolyesters/polyvinyl chloride, aliphatic-aromatic copolyesters/polycarbonate, aliphatic-aromatic copolyesters/polyvinyl acetate-polyethylene copolymer, or aliphatic-aromatic copolyesters/cellulose ethers, and aliphatic-aromatic copolyesters/nylon as more fully described in U.S. Pat. Nos. 5,292,783 and 5,446,079 and U.S. applications Ser. Nos. 08/429,400, 08/428,979, and 08/427,944, all filed Apr. 26, 1995, incorporated herein by reference. The preferred blends more particularly comprise binary blends of cellulose esters and aliphatic-aromatic copolyesters, cellulose esters and aliphatic polyesters as well as ternary blends of cellulose esters, aliphatic polyesters and/or aliphatic-aromatic copolyesters, and polymeric compounds as well as fibers, molded objects, and thin films prepared therefrom which have one or more of the above or below described desirable properties. More specifically, the preferred blends include a binary blend comprising:

I.(A) about 5% to about 98% of a $C_1$–$C_{10}$ ester of cellulose having a DS/AGU of about 1.8 to 3.0 and an inherent viscosity of about 0.2 to about 3.0 deciliters/gram as measured at a temperature of 25° C. for a 0.5 g sample in 100 ml of a 60/40 parts by weight solution of phenol/tetrachloroethane, and (B) about 2% to about 95% of a aliphatic-aromatic copolyester having an inherent viscosity of about 0.4 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B);

a binary blend comprising:

II.(A) about 5% to about 98% of a $C_1$–$C_{10}$ ester of cellulose having a DS/AGU of about 1.8 to 2.75 and an inherent viscosity of about 0.2 to about 3.0 deciliters/gram as measured at a temperature of 25° C. for a 0.5 g sample in 100 ml of a 60/40 parts by weight solution of phenol/tetrachloroethane, and (B) about 2% to about 95% of a aliphatic polyester having an inherent viscosity of about 0.4 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B);

ternary blends comprising:

III.(A) about 4% to about 97% of a $C_1$–$C_{10}$ ester of cellulose having a DS/AGU of about 1.8 to 3.0 and an inherent viscosity of about 0.2 to about 3.0 deciliters/gram as measured at a temperature of 25° C. for a 0.5 g sample in 100 ml of a 60/40 parts by weight solution of phenol/tetrachloroethane, (B) about 2% to about 95% of an aliphatic polyester and/or a aliphatic-aromatic copolyester having an inherent viscosity of about 0.4 to about 2.0 deciliters/gram as measured at a temperature of 25° C. for a 0.5 g sample in 100 ml of a 60/40 parts by weight solution of phenol/tetrachloroethane, and (C) about 1% to about 94% of polymeric compounds having an inherent viscosity of about 0.4 to about 2.0 deciliters/gram as measured at a temperature of 25° C. for a 0.5 g sample in 100 ml of a 60/40 parts by weight solution of phenol/tetrachloroethane, said percentages being based on the weight of component (A) plus component (B) plus component (C);

blends also comprising:

IV.(A) about 50% to about 99% of a binary blend of (I) or (II) or a ternary blend of (III) having an inherent viscosity of about 0.4 to about 3.0 deciliters/gram as measured at a temperature of 25° C. for a 0.5 g sample in 100 ml of a 60/40 parts by weight solution of phenol/tetrachloroethane, (B) about 1% to about 50% of biodegradable additives, said percentages being based on the weight of component (A) plus component (B); and blends comprising:

V.(A) about 50% to about 99% of a binary blend of (I) or (II) or a ternary blend of (III) having an inherent viscosity of about 0.4 to about 3.0 deciliters/gram as measured at a temperature of 25° C. for a 0.5 g sample in 100 ml of a 60/40 parts by weight solution of phenol/tetrachloroethane, (B) about 0.05% to about 2% of immiscible hydrophobic agent, said percentages being based on the weight of component (A) plus component (B).

Many of these blends have the advantage of biodegradability or industrial compostability, so that films or fibers made from the blends are useful in disposable absorbant articles such as infant diapers, incontinence briefs, sanitary napkins or catamenials, tampons, etc. They also have the advantage of industrial compostability.

A single fiber of the present invention preferably has a denier of between about 3 and about 1,000, more preferred is between about 10 and about 70.

Fiber shape and fiber/fluid interface variables can be manipulated to increase fluid transport rate per unit weight of fiber (flux) by accomplishing the following:

(a) using less polymer by making the fiber cross-sectional area smaller (thinner legs, walls, backbones, etc., which form the channeled structure);

(b) moderately increasing channel depth-to-width ratio;

(c) changing (increasing or decreasing) channel width to the optimum width, and (d) increasing adhesion tension, $\alpha \cos \theta$, at the channel wall by the proper selection of a lubricant for the fiber surface (which results primarily in a decrease in the contact angle at the wall without a significant lowering of the fluid surface tension at the wall).

The fibers of the present invention preferably have a surface treatment applied thereto. Such surface treatment may or may not be critical to obtain the required spontaneous transportability property. The nature and criticality of such surface treatment for any given fiber can be determined by a skilled artisan through routine experimentation using techniques known in the art and/or disclosed herein. A preferred surface treatment is a coating of a hydrophilic lubricant on the surface of the fiber. Such coating is typically uniformly applied at about a level of at least 0.05 weight percent, with about 0.1 to about 2 weight percent being preferred. Preferred hydrophilic lubricants include polyoxyethylene (23) lauryl ether, polyoxyethylene (20) oleyl ether, polyoxylene-polyoxypropylene-sorbitan linoleic phthalic ester, Milease T, and a potassium lauryl phosphate based lubricant comprising about 70 weight percent poly(ethylene glycol) 600 monolaurate. Many surfactants provide very good wetting of surfaces by lowering fluid surface tension and decreasing contact angle and thereby yield low adhesion tension at the surface. Therefore, it is important that the surfactant possess some attraction for the polyester surface (hydrophobic) and also for water (hydrophilic). It is also preferred that the surfactant bind tightly to the polyester surface and at the same time present high hydrophilicity to the water side of the interface. Another surface treatment is to subject the fibers to oxygen plasma treatment, as taught in, for example, *Plastics Finishing and Decoration*, Chapter 4, Ed. Don Satas, Van Nostrand Reinhold Company (1986).

The novel spinnerets of the present invention must have a specific geometry in order to produce fibers that will spontaneously transport aqueous fluids.

In FIG. 3, W is between 0.064 millimeters (mm) and 0.12 mm.

$X_2$ is $4W^{+4W}_{-1W}$;

$X_4$ is $2W \pm 0.5W$;

$X_6$ is $6W^{+4W}_{-2W}$;

$X_8$ is $6W^{+5W}_{-2W}$;

$X_{10}$ is $7W^{+5W}_{-2W}$;

$X_{12}$ is $9W^{+5W}_{-2W}$;

$X_{14}$ is $10W^{+5W}_{-2W}$;

$X_{16}$ is $11W^{+5W}_{-2W}$;

$X_{18}$ is $6W^{+5W}_{-2W}$;

$\theta_2$ is $30° \pm 30°$;

$\theta_4$ is $45° \pm 45°$;

$\theta_6$ is $30° \pm 30°$;

and $\theta_8$ is $45° \pm 45°$.

Figure 4:
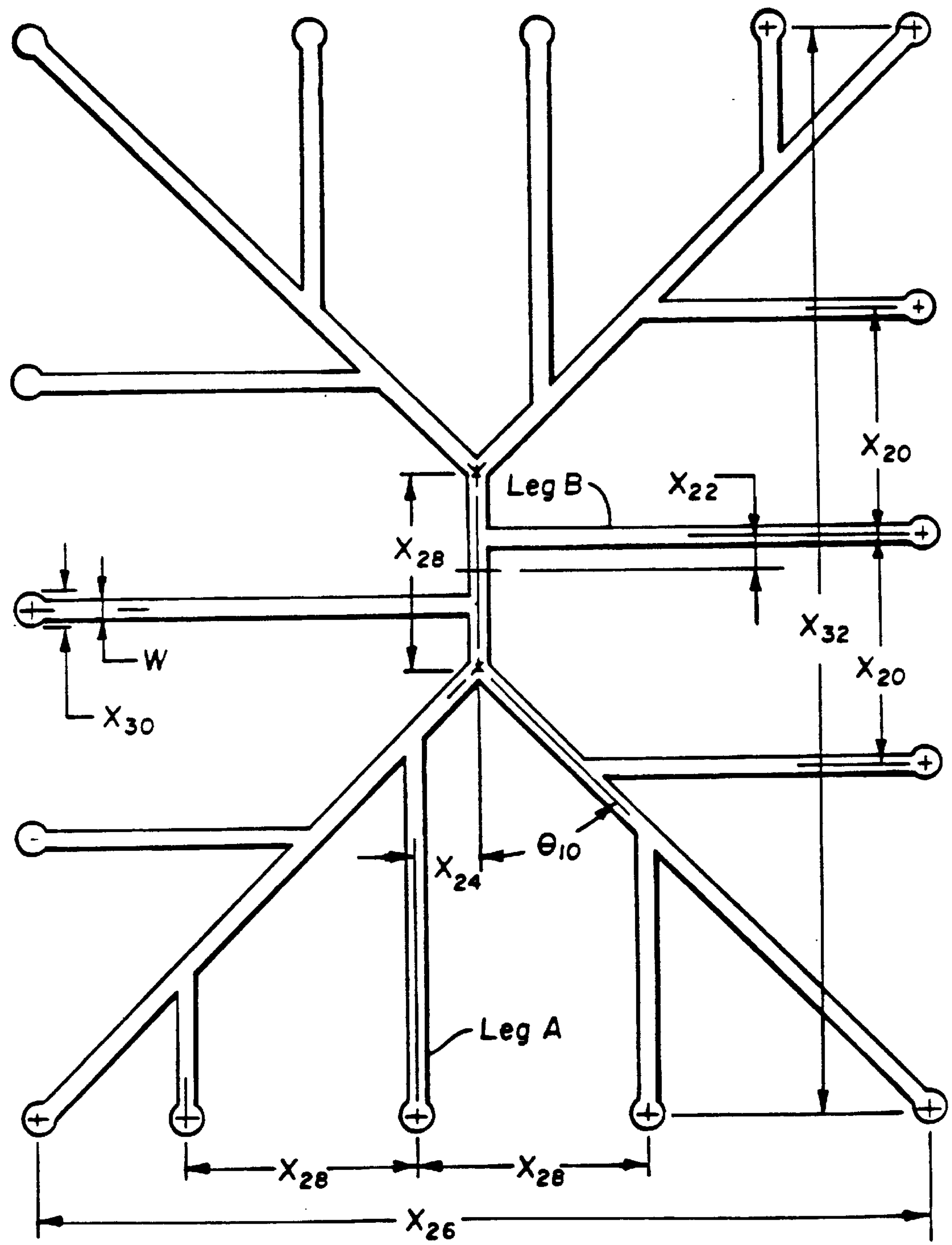
FIG. 4—schematic representation of an orifice of a spinneret useful for producing a spontaneously transportable fiber.

In FIG. 4, W is between 0.064 mm and 0.12 mm;

$X_{20}$ is $17W^{+5W}_{-2W}$;

$X_{22}$ is $3W \pm W$;

$X_{24}$ is $4W \pm 2W$;

$X_{26}$ is $60W^{+8W}_{-4W}$;

$X_{28}$ is $17W^{+5W}_{-2W}$;

$X_{30}$ is $2W \pm 0.5W$;

$X_{32}$ is $72W^{+10W}_{-5W}$;

and $\theta_{10}$ is $45° \pm 15°$.

In addition, each Leg B can vary in length from 0 to $$\frac{X_{26}}{2};$$

and each Leg A can vary in length from 0 to tan $(90-\theta_{10})$ $$\tan(90-\theta_{10})\left[\frac{X_{26}}{2}-X_{24}\right].$$

Figure 5:
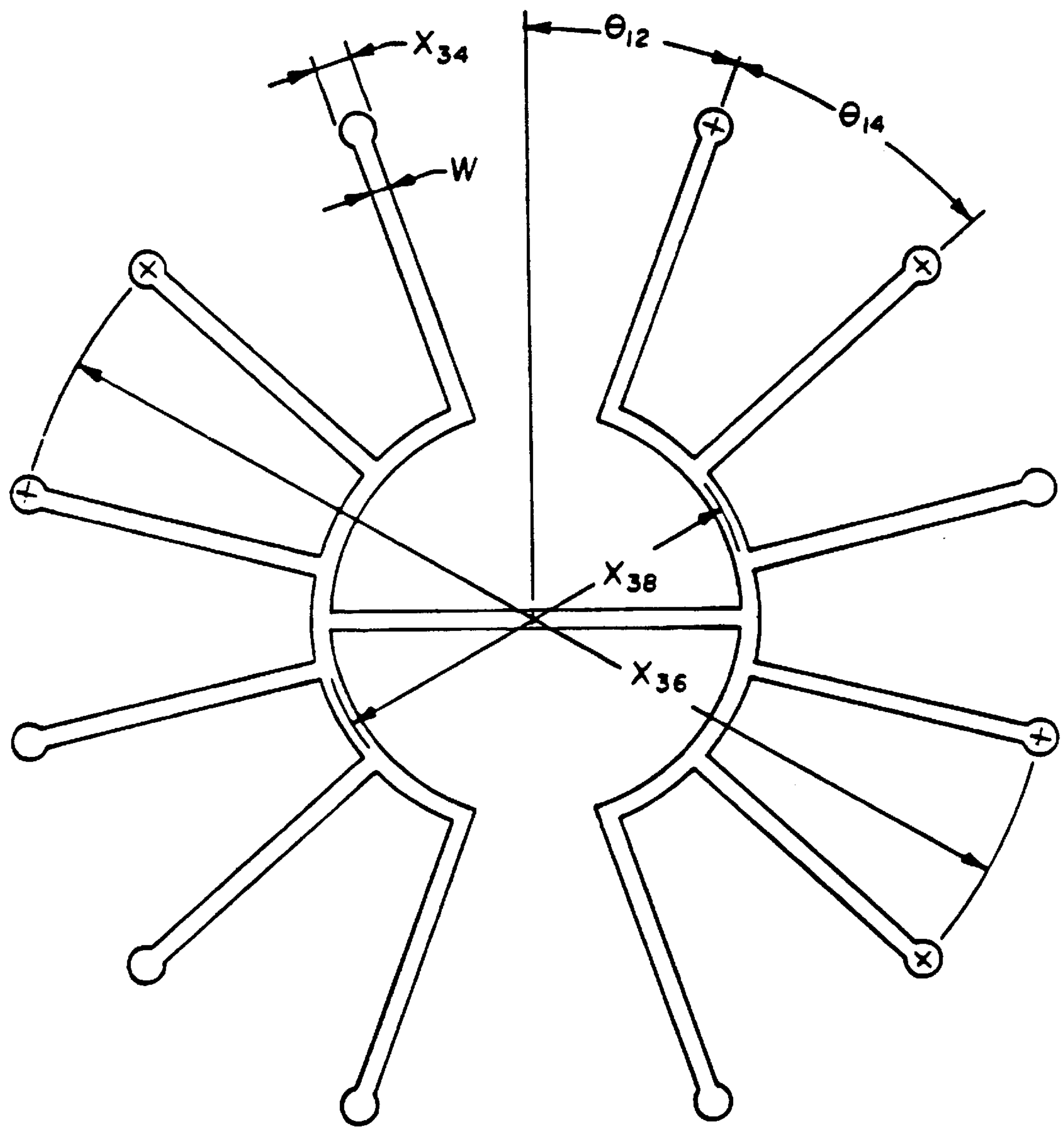
FIG. 5—schematic representation of an orifice of a spinneret useful for producing a spontaneously transportable fiber.

In FIG. 5, W is between 0.064 mm and 0.12 mm;

$X_{34}$ is $2W \pm 0.5W$;

$X_{36}$ is $58W^{+20W}_{-10W}$;

$X_{38}$ is $24W^{+20W}_{-6W}$;

$\theta_{12}$ is $20°^{+15°}_{-10°}$;

-continued $$\theta_{14} \text{ is } \frac{180° - 2\theta_{12}}{n-1};$$

and $n$ = number of legs per 180° = 2 to 6.

and n=number of legs per 180°=2 to 6.

Figure 6:
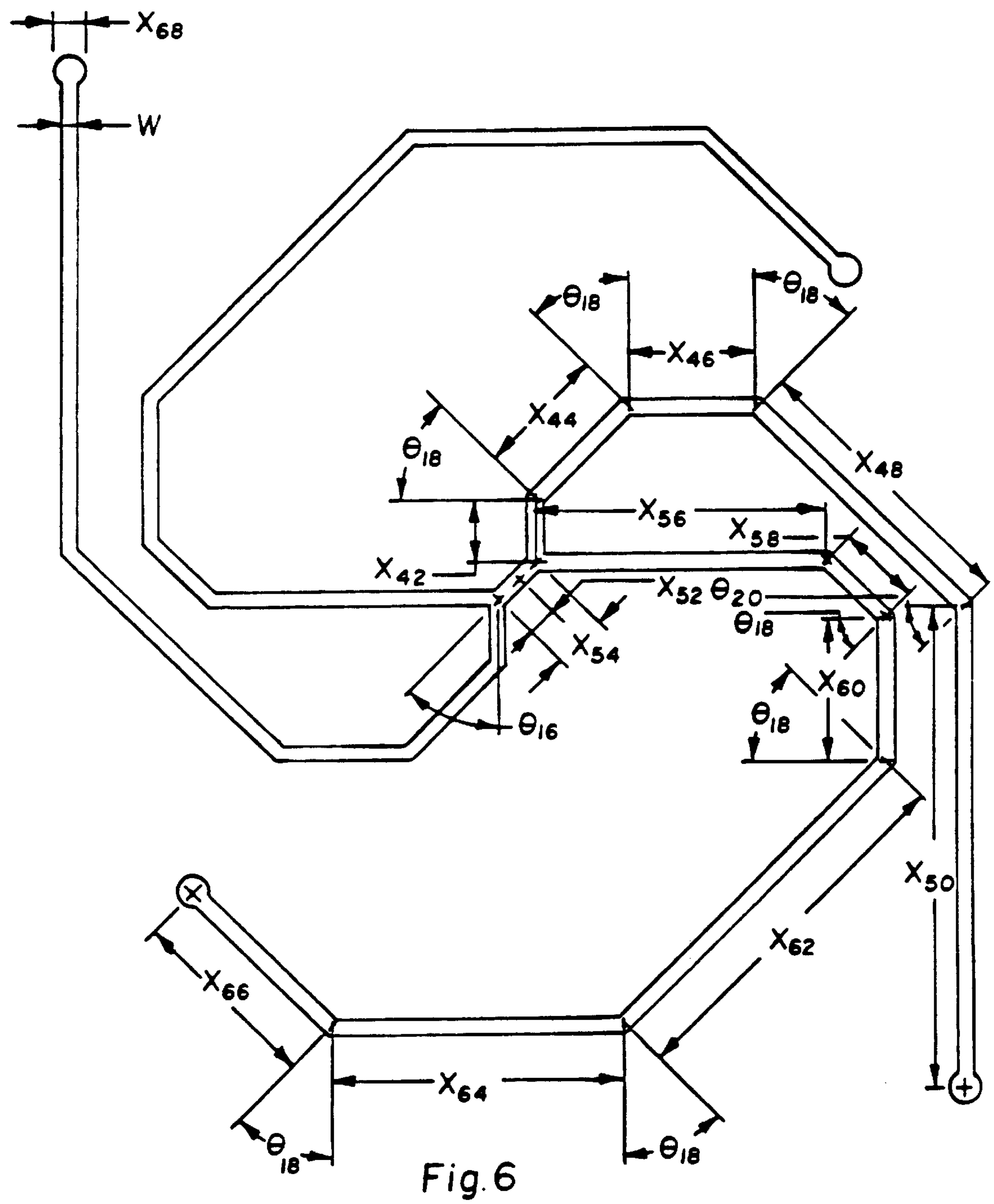
FIG. 6—schematic representation of an orifice of a spinneret useful for producing a spontaneously transportable fiber.
Figure 6:
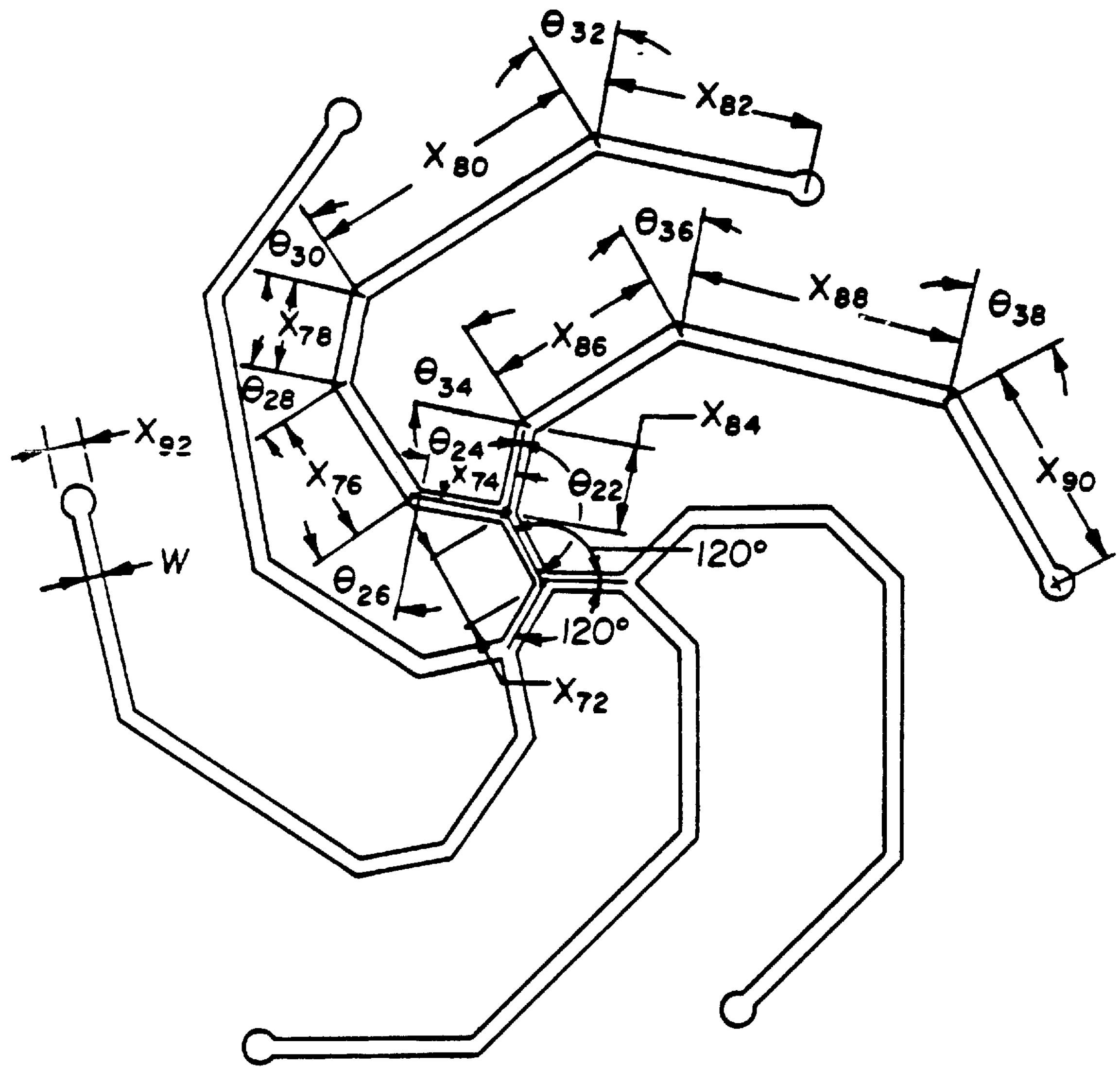

In FIG. 6, W is between 0.064 mm and 0.12 mm;

$X_{42}$ is $6W^{+4W}_{-2W}$;

$X_{44}$ is $11W \pm 5W$;

$X_{46}$ is $11W \pm 5W$;

$X_{48}$ is $24W \pm 10W$;

$X_{50}$ is $38W \pm 13W$;

$X_{52}$ is $3W^{+3W}_{-1W}$;

$X_{54}$ is $6W^{+6W}_{-2W}$;

$X_{56}$ is $11W \pm 5W$;

$X_{58}$ is $7W \pm 5W$;

$X_{60}$ is $17W \pm 7W$;

$X_{62}$ is $28W \pm 11W$;

$X_{64}$ is $24W \pm 10W$;

$X_{66}$ is $17W \pm 7W$;

$X_{68}$ is $2W \pm 0.5W$;

$\theta_{16}$ is $45°^{+30°}_{-15°}$;

$\theta_{18}$ is $45° \pm 15°$;

$\theta_{20}$ is $45° \pm 15°$.

In FIG. 6B, W is between 0.064 mm and 0.12 mm, $X_{72}$ is $8W^{+4W}_{-2W}$, $X_{74}$ is $8W^{+4W}_{-2W}$, $X_{76}$ is $12W \pm 4W$, $X_{78}$ is $8W \pm 4W$, $X_{80}$ is $24W \pm 12W$, $X_{82}$ is $18W \pm 6W$, $X_{84}$ is $8W^{+4W}_{-2W}$, $X_{86}$ is $16W \pm 6W$, $X_{88}$ is $24W \pm 12W$, $X_{90}$ is $18W \pm 6W$, $X_{92}$ is $2W \pm 0.5W$, $\theta_{22}$ is $135° \pm 30°$, $\theta_{24}$ is $90° \pm^{45°}_{30°}$, $\theta_{26}$ is $45° \pm 15°$, $\theta_{28}$ is $45° \pm 15°$, $\theta_{30}$ is $45° \pm 15°$, $\theta_{32}$ is $45° \pm 15°$, $\theta_{34}$ is $45° \pm 15°$, $\theta_{36}$ is $45° \pm 15°$, and $\theta_{38}$ is $45° \pm 15°$.

Figure 7:
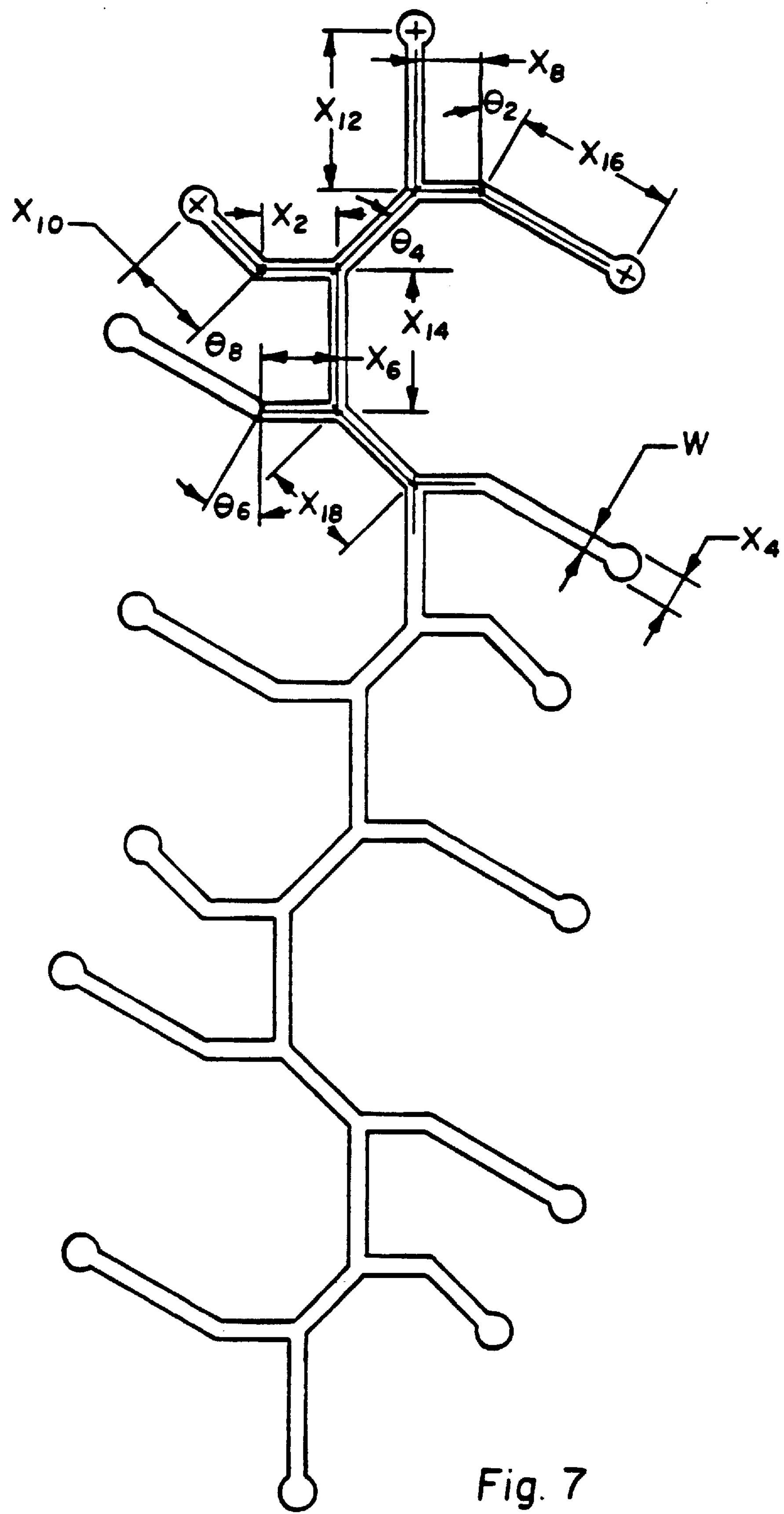
FIG. 7—schematic representation of an orifice of a spinneret having 2 repeating units, joined end to end, of the orifice as shown in FIG. 3.

In FIG. 7, the depicted spinneret orifice contains two repeat units of the spinneret orifice depicted in FIG. 3. Therefore, the same dimensions for FIG. 3 apply to FIG. 7. Likewise, in FIG. 8, the depicted spinneret orifice contains four repeat units of the spinneret orifice depicted in FIG. 3. Therefore, the same dimension for FIG. 3 applies to FIG. 8.

Figure 33:
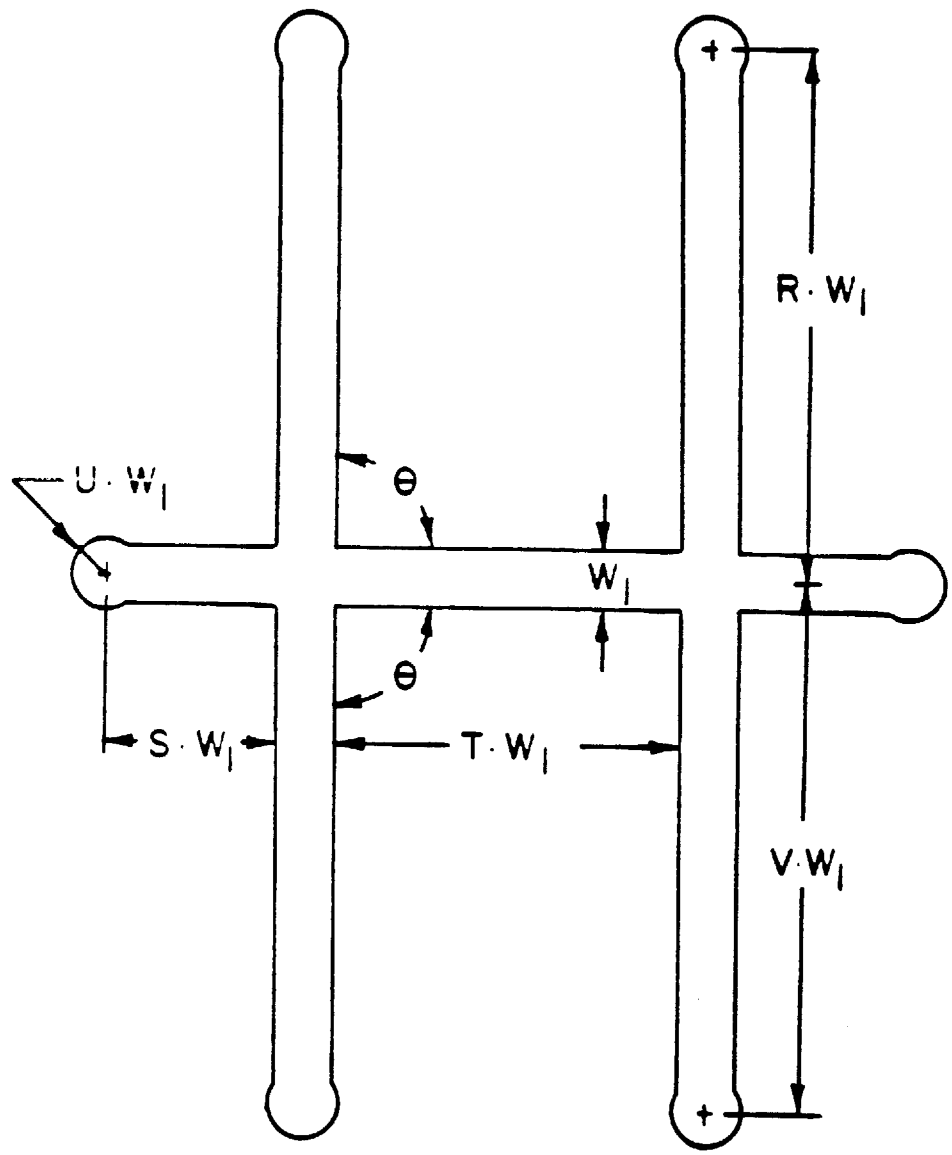
FIG. 33—a schematic representation of a preferred "H" shape orifice of a spinneret useful for producing a spontaneously transportable fiber.

FIG. 33 depicts a preferred "H" shape spinneret orifice of the invention. In FIG. 33 $W_1$ is between 60 and 150 $\mu$, θ is between 80° and 120°, S is between 1 and 20, R is between 10 and 100, T is between 10 and 300, U is between 1 and 25, and V is between 10 and 100. In FIG. 33 it is more preferred that $W_1$ is between 65 and 100$\mu$, θ is between 90° and 110°, S is between 5 and 10, R is between 30 and 75, T is between 30 and 80, U is between 1.5 and 2, and V is between 30 and 75.

Figure 34:
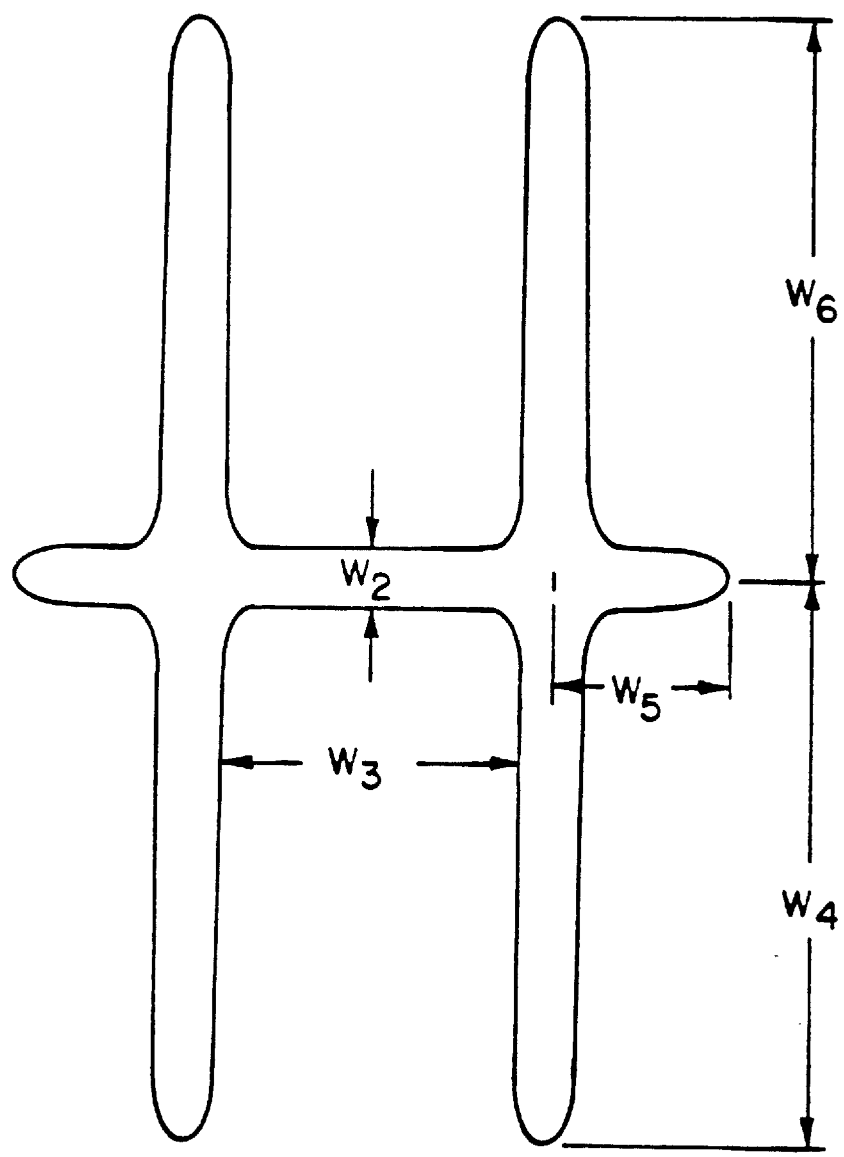
FIG. 34—a schematic representation of a poly(ethylene terephthalate) fiber cross-section made using a spinneret having an orifice as illustrated in FIG. 33. p FIGS. 35A and 35B—are schematic representations of a preferred "H" shape orifice of a spinneret useful for producing a spontaneously transportable fiber (see Example 23). "W" as shown herein is the same as "$W_1$" referred to in Example 23.

FIG. 34 depicts a poly(ethylene terephthalate fiber cross-section made from the spinneret orifice of FIG. 33. In FIG. 34 $W_2$ is less than 20$\mu$, $W_3$ is between 10 and 300$\mu$, $W_4$ is between 20 and 200$\mu$, $W_5$ is between 5 and 50$\mu$, and $W_6$ is between 20 and 200$\mu$. In FIG. 34 it is more preferred that $W_2$ is less than 10$\mu$, $W_3$ is between 20 and 100$\mu$, $W_4$ is between 20 and 100$\mu$, and $W_5$ is between 5 and 20$\mu$.

Figure 16:
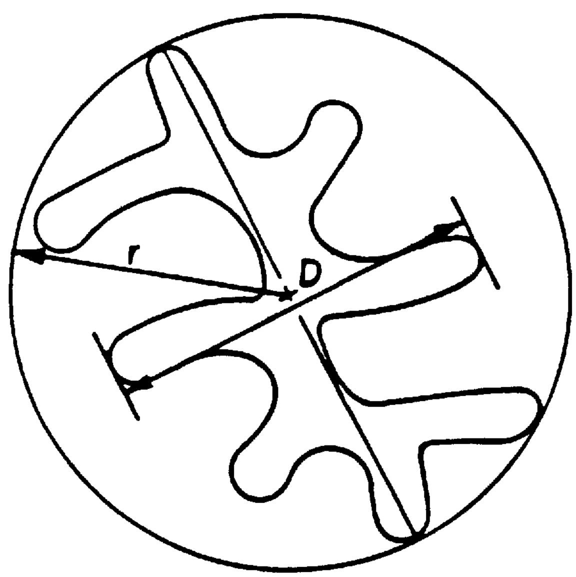
FIG. 16—schematic representation of a fiber cross-section made using a spinneret having an orifice as illustrated in FIG. 3 (Example 1). Exemplified is a typical means of determining the shape factor X.

FIG. 16 illustrates the method for determining the shape factor, X, of the fiber cross-section. In FIG. 16, r=37.5 mm, $P_w$=355.1 mm, and D=49.6 mm. thus, for the fiber cross-section of FIG. 16:

$$X = \frac{355.1}{4 \times 37.5 + (\pi - 2)49.6} = 1.72.$$

Figure 18:
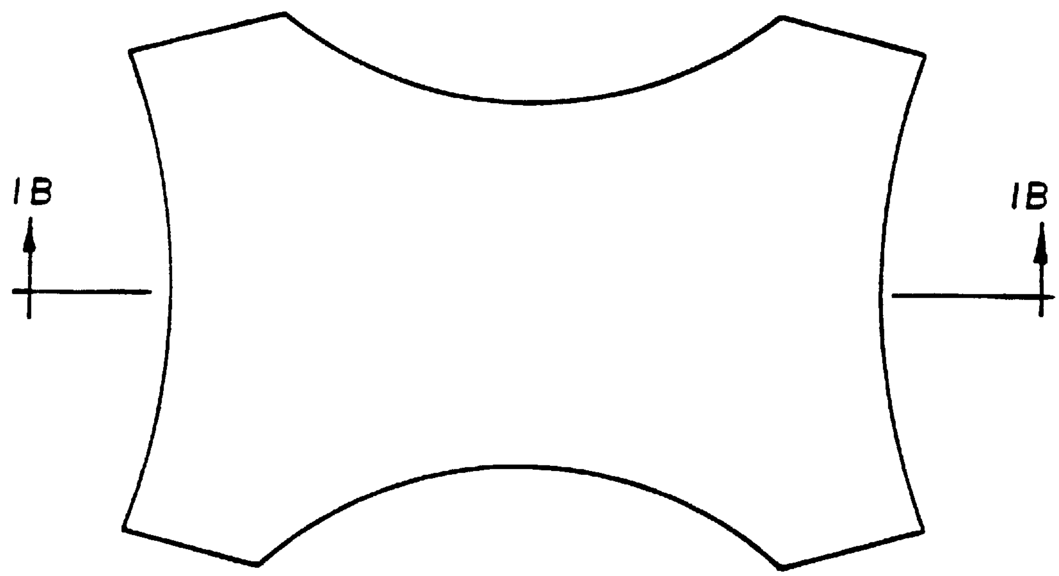
Figure 18:
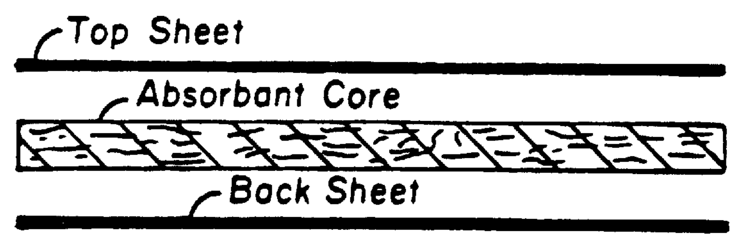

The fibers of the present invention are preferably incorporated into an absorbant article in which it is desired to move or transport aqueous fluids. Such absorbant articles include, but are not limited to, diapers, incontinence pads, feminine hygiene articles such as tampons, ink cartridges, wipes, and the like. FIG. 18A shows a schematic representation of the top view of a typical diaper and FIG. 18B shows an exploded side view of a typical diaper along the major axis of the diaper.

The fibers of the present invention can be in the form of crimped or uncrimped tows or staple fibers comprising a plurality of the fibers of the present invention.

An absorbant article of the present invention comprises two or more fibers of the present invention wherein at least part of said fibers are located near the center of said absorbant article and at least part of the same said fibers are located away from the center of said absorbant article; and wherein said fibers are capable of being in contact with an aqueous fluid for about at least 10 seconds near the center of said absorbant article; and wherein away from the center of said absorbant article one or more sinks are present in said absorbant article that are in contact with said fiber. As used in this context, "near the center" of the absorbant article means the geometric center and the area consisting of 50 area % of the total article immediately surrounding said geometric center; "away from the center" of the absorbant article means the remaining 50 area % that is not near the center of the article. Preferred sinks are fluff pulp, superabsorbant material, and combinations thereof. It is preferred that said sinks are in contact with a given fiber near the end of such fiber in the area away from the center of the article. As used in this context the term "near the end" of a fiber refers to an actual end of a fiber or the area consisting of the end 10% of the length of the fiber.

Another preferred absorbant article of the present invention comprises a diaper or incontinent pad having a major axis and a minor axis and a length in excess of a width which comprises a top sheet, a back sheet, and an absorbant core comprising at least one absorbant layer wherein said article further comprises the tow of the present invention. The tow may be crimped or uncrimped.

The tow in said absorbant article can be located in several different positions with several different spatial orientations. For example, the tow can be uniformly spread across all or part of the width of the article and the fibers of the tow can be substantially parallel to the major axis of the article and extend from about ½ to substantially the length of the article (see FIG. 23B).

Figure 23:
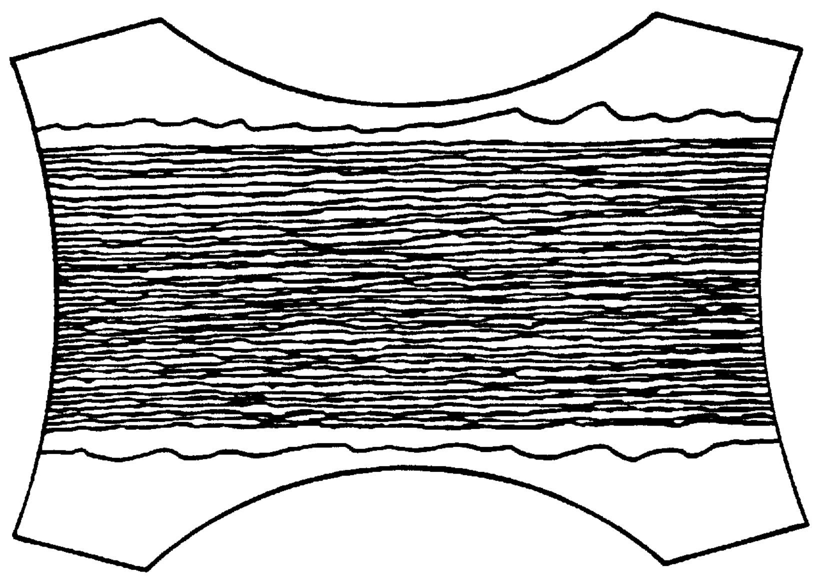
Figure 23:
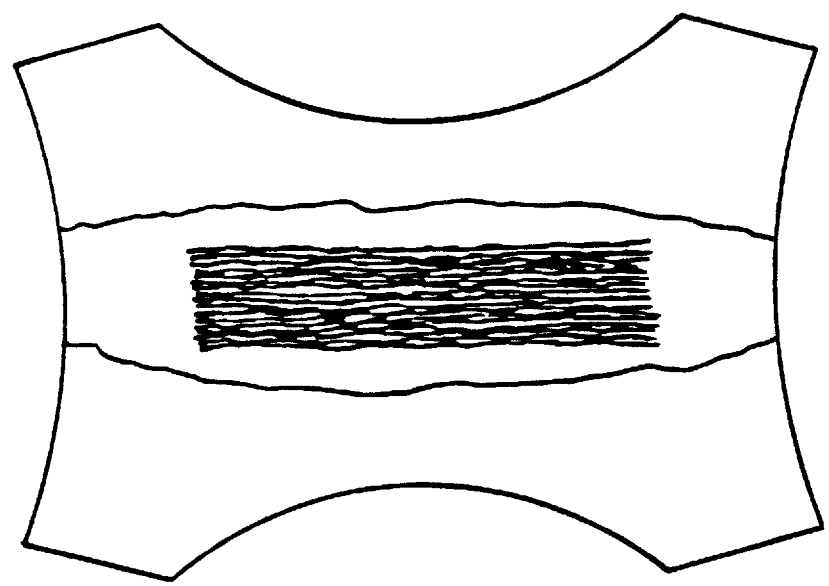

Alternatively, the fibers of the tow can be substantially parallel to the major axis of the diaper and extend substantially the length of the diaper (see FIG. 23A).

By use of a tow of the fibers of the invention in an absorbant article such as a diaper, urine can be transported to a larger surface area on the diaper. Thus, the amount of superabsorbant material required in the diaper can be reduced and the diaper surface will be drier.

By utilizing the fibers of the present invention in a diaper construction, it is preferred that at least one of the following benefits be realized.

(i) The effective surface area of the diaper utilized for urine/aqueous fluid movement will increase by 5% to 30%.

(ii) The amount of superabsorbant material utilized in the diaper will reduce by 2% to 25%.

(iii) The diaper will be thinner by about 2% to 15%.

(iv) The strikethrough (seconds)/rewet (grams) responses as measured by the strikethrough/rewet test described in U.S. Pat. No. 4,324,247 are improved with the strike-through being reduced from about 2 to about 50% and the rewet being reduced from about 2 to about 70% when compared to equivalent structures without the fibers (tow) of this invention being present. This results in the interface between the diaper and the wearer remaining drier.

The fibers of the tow can be located in the absorbant article at any place which will result in an overall beneficial effect. For example, the fibers can be located between the top sheet and the absorbant core, incorporated into the absorbant core, between the absorbant core and the back sheet, or multiple combinations of the above.

The top sheet of the absorbant article of the present invention can be made of any material known in the art for such use. Such materials include, but are not limited to, polypropylene, polyethylene, polyethylene terephthalate, cellulose or rayon; preferred is polypropylene. The top sheet is the sheet which is designed to be in contact with the body during typical end uses. Such a top sheet is alternatively referred to in the art as a "facing sheet," and it is typically comprised of a web of short and/or long fibers.

The back sheet of the absorbant article of the present invention can be made of any material known in the art for such use. Such materials include, but are not limited to, polyethylene, a polyester, or polypropylene; preferred is polyethylene. The back sheet is typically impervious to body fluids such as urine.

The absorbant core of the absorbant article of the present invention preferably comprises fluff pulp and, optionally, superabsorbant powder. Fluff pulp is used extensively in the art. Fluff pulp is a batt formed of loosely compacted short cellulose fibers, such as wood pulp fibers, or cotton linters, or mixtures thereof, which are primarily held together by interfiber bonds usually requiring no added adhesive although thermoplastic binder(s) may also be used. This batt is a low density coherent web of loosely compacted fibers preferably comminuted wood pulp fibers. Examples of absorbant powder are polyacrylates, acrylic acid based polymers, saponified starch, and polyacrylonitrile graft copolymers.

Figure 24:
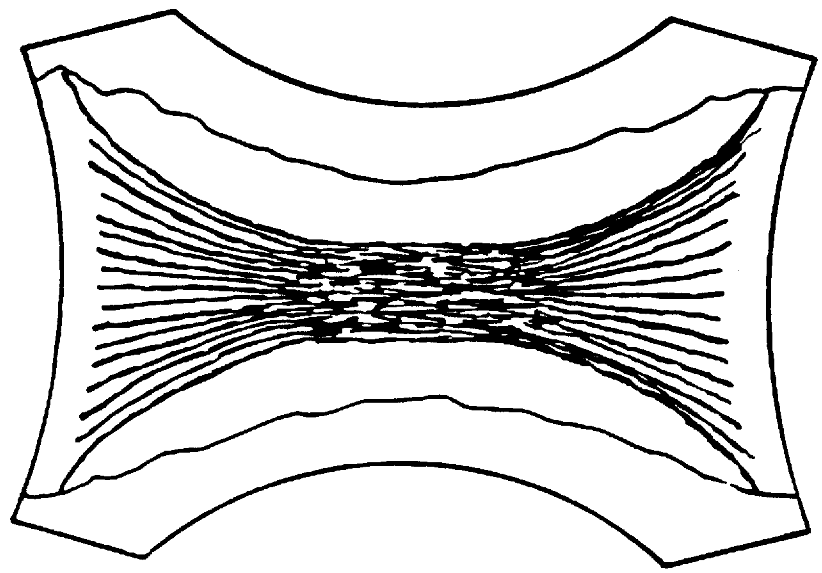
FIG. 24—a schematic representation of the top view of a diaper. The lines in the cut-away view represent tightly compacted tow (made from fibers of the present invention) in the impingement zone and the tow is flared at the end.

Other preferred embodiments of the absorbant article of the present invention include articles wherein the fibers of the tow are tightly compacted in the impingement zone such that the fibers are substantially in contact with each other, and toward each end of the length of the article the fibers of the tow flare and are substantially not in contact with each other (see FIG. 24). In addition, the tow can have from one half to ten turns of twist in the impingement zone. The terms "impingement zone", "impinging area", and like terms refer to that area or zone where body fluid first contacts or impinges upon the absorbant article during its intended use. The impingement zone may be near the center of the absorbant article, away from the center, or overlapping both areas.

Figure 22:
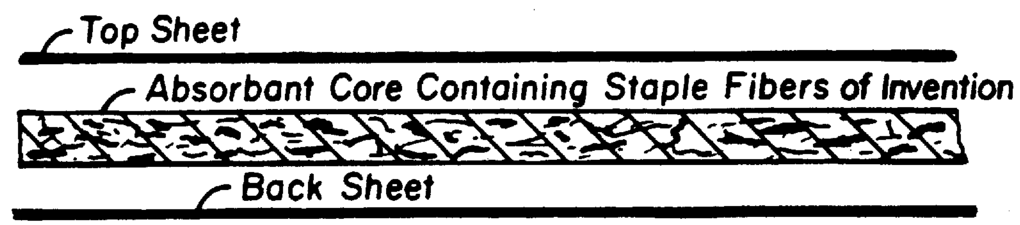
FIG. 22—a schematic representation of an exploded side view of a diaper along the major axis of the diaper. The staple fibers made from fibers of the present invention is in the absorbant core.

It is also contemplated that the fibers of the present invention can be in the form of staple fiber which may or may not be crimped. When in the form of staple fiber, a preferred absorbant article of the present invention comprises a diaper or incontinent pad having a major axis and a minor axis and a length in excess of a width comprising a top sheet, a back sheet, and an absorbant core comprising at least one absorbant layer wherein said core comprises an intimate blend of the staple fiber of the present invention (see FIG. 22).

Figure 25:
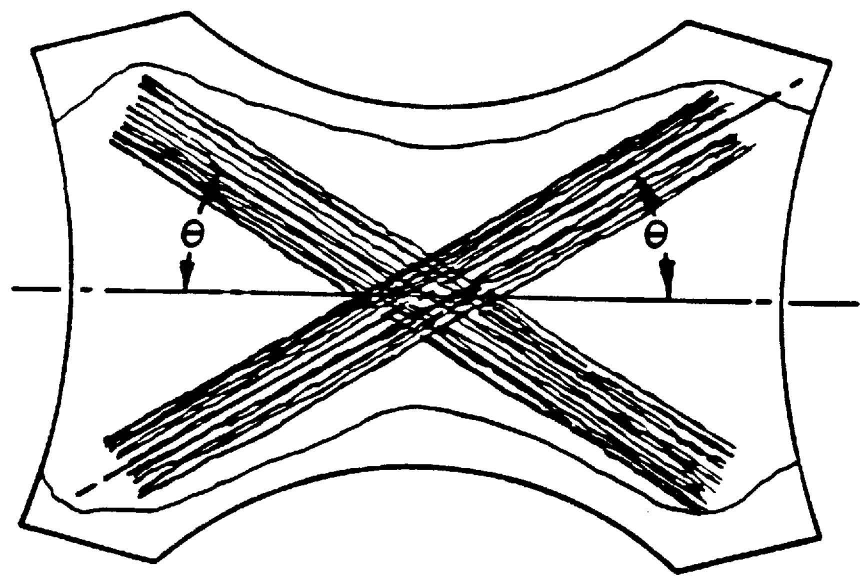
FIG. 25—a schematic representation of the top view of a diaper. The lines in the cut-away view represent tow made from fibers of the present invention. The major axis of the tow is inclined at an angle of 30° with respect to the major axis of the diaper.

Another preferred embodiment of the absorbant article of the present invention is an article containing up to three tows of the invention wherein the major axis of each tow lies between ±30° around the major axis of the article and wherein the tows lie either just beneath the top sheet, lie intimately mixed with the absorbant core or lie adjacent to the back sheet (see FIG. 25).

Another preferred embodiment of the absorbant article of the present invention is a two piece diaper wherein one piece contains tow of the invention and receives the impinging fluid during the diaper's intended use and is reusable, and wherein the second piece is a fluid storage element and is replaceable.

The absorbant article of this invention can optionally contain a tissue or low density spacer layer which is adjacent to the top sheet between the top sheet and absorbant core. In such case the tow preferably lies between the absorbant core and said tissue or density spacer.

In still another preferred embodiment of the absorbant article of the present invention the fibers of the tow are in intimate contact with part of the absorbant core located away from the impingement zone.

Other absorbant articles contemplated by the present invention (which may or may not have a specific impingement zone) in which the fibers of the present invention can be beneficial include, but are not limited to, a sweat absorbing headband or wristband, a surgical sponge, a wound dressing, a sweat absorbing insole for footwear, a general purpose wiping article, a fabric softener strip for use in clothes dryers, a wound drain or a surgical drain, a towel, a geotextile, athletic clothing such as athletic socks and jogging suits, a cosmetic applicator, a furniture polish applicator, a pap smear sampler, a throat culture sampler, a blood-analyzer test element, household and industrial deodorizers, humidifier fabric, moist filter media, orthopaedic cast liners, wipes for medical applications (e.g., containing an alcoholic fluid for use on the surface of skin) and the like.

Ink cartridges are typically made with tows of cellulose ester fibers and polyester fibers. Important criteria for ink cartridges are (i) ink holding capacity and (ii) effective utilization of the ink reservoir. The art of making ink cartridges is described in U.S. Pat. Nos. 4,104,781, 4,286,005, and 3,715,254. The use of fiber bundles made from fibers of the present invention in these ink cartridges offer significant advantages of increased ink holding capacity and/or effective utilization of the ink reservoir due to the nature of the fiber cross-sections and the spontaneous surface transportable nature of the single fibers of the present invention.

In the geotextile field, one of the important functions of the geotextile material is to transport rain water and other aqueous fluids from unwanted regions of the land to distant areas. It is believed that due to the spontaneous surface transportable nature of the fibers of the present invention, articles made from these fibers will enhance in transporting aqueous fluids from one region to another area in geotextile applications.

In active sports and outdoor activities, it is important that the human body remain relatively dry for comfort. Generally, human sweat or perspiration causes a feeling of being "wet". One of the important functions of garments and other articles worn next to skin is then to rapidly transport the "sweat" or "perspiration" from the skin to the garment or article worn next to the skin. Furthermore, it is important that such garments and articles should not absorb the bulk of this "sweat"; otherwise, it will take a long time to remove or dry the aqueous fluids from such garments and articles. For example, garments or such articles made of cotton or cellulosic fibers have a very high water absorption capacity (7–10%) and thus may not be highly desirable in such applications. However, garments or such articles worn next to skin made from fibers of the present invention and/or those in conjunction with blends of other fiber types may be very desirable. The spontaneous surface transportable nature of the fibers of the present invention can lead to rapidly removing the "sweat" or "perspiration" from the human body and thereby keeping the body relatively dry. Thus, a sweat absorbing headband or wristband, an insole for footwear, a towel, athletic socks, jogging suit, etc. made from fibers of the present invention can be highly desirable.

The fibers of the present invention can be prepared by techniques known in the art and/or disclosed herein using a novel spinneret of the present invention or other spinneret that will result in a fiber cross-section of the appropriate geometry and properties.

In general, a process of the present invention can be described as a process for preparing a fiber of the present invention which comprises heating a material capable of forming a fiber at or above its melting point followed by extruding said heated material through at least one spinneret having at least one orifice capable of forming the desired fiber. The fiber may be drafted and/or thermally stabilized. The fiber thus formed may then optionally be treated with a surface treatment such as a hydrophilic coating or plasma treatment as described hereinbefore.

The absorbant articles of the present invention can be made by use of techniques known in the art, for example in U.S. Pat. Nos. 4,573,986; 3,938,522; 4,102,340; 4,044,768; 4,282,874; 4,285,342; 4,333,463; 4,731,066; 4,681,577; 4,685,914; and 4,654,040; and/or by techniques disclosed herein. The tow of the present invention can be incorporated into the absorbant article at any location which will improve fluid movement so as to better utilize the absorbant materials of the article.

Spunbonded structures, well known in the art, can also be made from filament strands of the present invention. Care must be exercised in the calendaring step so as not to damage the cross-section of the fibers and thereby inhibit the spontaneous surface transport.

Continuous filament yarns of typical textile deniers and filament counts can also be made using the present invention. The yarns are useful in providing scrim fabrics which will spontaneously surface transport aqueous fluids.

The following examples are to illustrate the invention but should not be interpreted as a limitation thereon.

EXAMPLES

Example 1 (Base Fiber Preparation)

Figure 9:
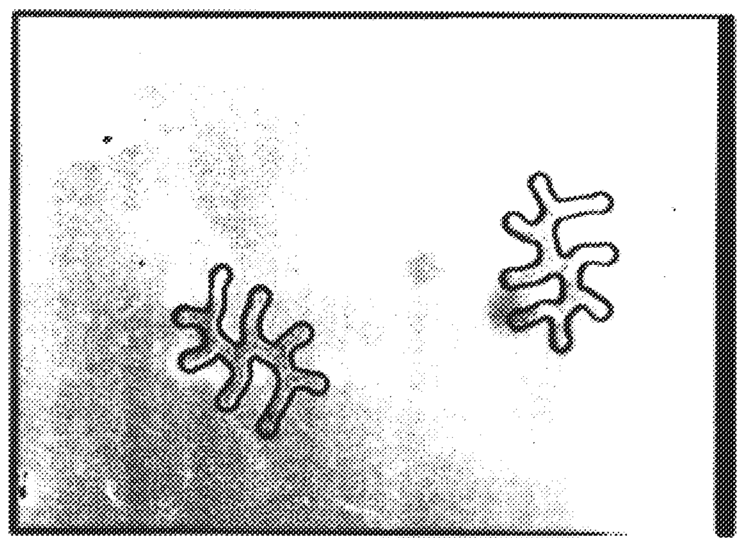
FIG. 9—photomicrograph of a poly(ethylene terephthalate) fiber cross-section made using a spinneret having an orifice as illustrated in FIG. 3 (specific dimensions of spinneret orifice described in Example 1).

Poly(ethylene terephthalate) (PET) polymer of 0.6 I.V. was used in this example. I.V. is the inherent viscosity as measured at 25° C. at a polymer concentration of 0.50 g/100 milliliters (mL) in a suitable solvent such as a mixture of 60% phenol and 40% tetrachloroethane by weight. The polymer was dried to a moisture level of ≦0.003 weight percent in a Patterson Conaform dryer at 120° C. for a period of 8 hours. The polymer was extruded at 283° C. through an Egan extruder, 1.5-inch diameter, with a length to diameter ratio of 28:1. The fiber was extruded through an eight orifice spinneret wherein each orifice was as shown in FIG. 3, W was 0.084 mm, $X_2$ was 4W, $X_4$ was 2W, $X_6$ was 6W, $X_8$ was 6W, $X_{10}$ was 7W, $X_{12}$ was 9W, $X_{14}$ was 10W, $X_{16}$ was 11W, $X_{18}$ was 6W, $\theta_2$ was 0°, $\theta_4$ was 45°, $\theta_6$ was 30°, and $\theta_8$ was 45°. The polymer throughput was about 7 pounds (lb)/hour. The air quench system has a cross-flow configuration. The quench air velocity at the top of the screen was an average of 294 feet (ft)/minute. At a distance of about 7 inches from the top of the screen the average velocity of the quench air was about 285 ft/minute, and at a distance of about 14 inches from the top of the screen the average quench air velocity was about 279 ft/minute. At about 21 inches from the top of the air screen the average air velocity was about 340 ft/minute. The rest of the screen was blocked. Spinning lubricant was applied via ceramic kiss rolls. The lubricant had a general composition as follows: it was a potassium lauryl phosphate (PLP) based lubricant having poly (ethylene glycol) 600 monolaurate (70% by weight) and polyoxyethylene (5) potassium lauryl phosphate (30% by weight). An emulsion of the above lubricant with water (90%) was used as the spinning lubricant. The lubricant level on the fiber samples was about 1.5%. Fibers of 20 dpf (denier per filament) were wound at 3,000 meters per minute (MPM) on a Barmag SW4SL winder. A photomicrograph of a cross-section of this fiber is shown in FIG. 9 (150× magnification). The single fiber was tested for spontaneous surface transportation of an aqueous solution which was aqueous Syltint Poly Red® (obtained from Milliken Chemicals) which is 80 weight % water and 20 weight % red colorant. The single fiber of 20 dpf spontaneously surface transported the above aqueous solution. The following denier per filament PET fibers were also made at different speeds as shown in Table I below:

TABLE I

| dpf | Spin Speed (MPM) | Winder |
|---|---|---|
| 20 | 3,000 | Barmag |
| 40 | 1,500 | Leesona |
| 60 | 1,000 | Leesona |
| 120 | 500 | Leesona |
| 240 | 225 | Leesona |
| 400 | 150 | Leesona |

All the single fibers of above PET fiber with the dpf of 20, 40, 60, 120, 240, and 400 spontaneously surface transported the aqueous solution of Syltint Poly Red® liquid. The value of the "X" parameter (as defined hereinbefore) for these fibers was about 1.7. PET film of 0.02 inch thickness was compression molded from the same polymer as that used for making the above fiber. The contact angle of distilled water on the above film was measured in air with a contact angle goniometer. The contact angle was 71.7°. Another sample of the same film as above was sprayed with the same lubricant as used for making the fiber in this example at about 1.5% level. The contact angle of distilled water on the PET film sprayed with the lubricant was about 7°. Thus, the factor $(1-X\cos\theta)$ in this case was $(1-1.7(\cos 7°))=-0.69$, which is less than zero.

Example 2 (Base Fiber Preparation)

Figure 11:
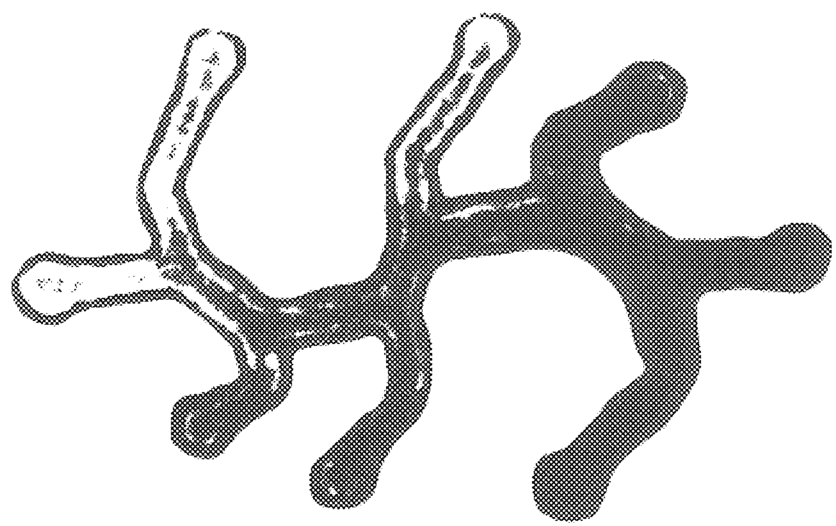
FIG. 11—photomicrograph of a nylon 66 fiber cross-section made using a spinneret having an orifice as illustrated in FIG. 3 (specific dimensions of spinneret orifice described in Example 2).

Polyhexamethylene adipamide (nylon 66) was obtained from Du Pont (Zytel® 42). The polymer was extruded at 279° C. A spinneret as shown in FIG. 3 was used to form 46 dpf fiber at 255 meters/minute speed. The specific dimensions of the spinneret orifices were the same as described in Example 1 except that $\theta_2$ was 30° instead of 0°. The quenching conditions were the same as those for obtaining PET fiber as in Example 1. A photomicrograph of the fiber cross-section is shown in FIG. 11 (150× magnification). The lubricant level on the fiber was about 1.8% by weight. The same lubricant as used in the PET fiber was used (Example 1). This Nylon 66 fiber spontaneously transported the aqueous Syltint Poly Red® solution on the fiber surface. The value of the "X" parameter for this fiber was about 1.9. Nylon 66 film of 0.02 inch thickness was compression molded from the same polymer as that used for making the fiber of Example 2. The contact angle of distilled water on the above film was measured in air with a contact angle goniometer. The contact angle was 64°. Another sample of the same film as above was sprayed with the same lubricant as used for making the fiber in this example at about the 1.8% level. The contact angle of distilled water on the nylon 66 film sprayed with the lubricant was about 2°. Thus, the factor $(1-X \cos \theta)$ in this case was $(1-1.9(\cos 2°))=-0.9$, which is less than zero.

Example 3 (Base Fiber Preparation)

Figure 10:
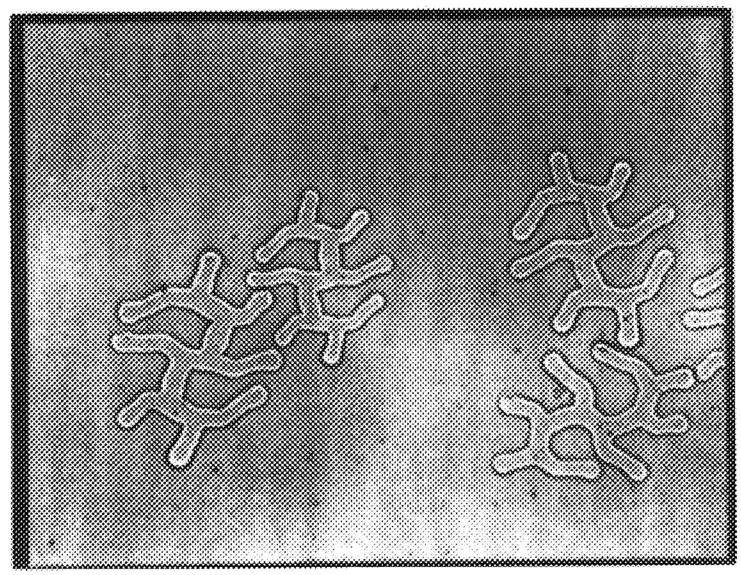
FIG. 10—photomicrograph of a polypropylene fiber cross-section made using a spinneret having an orifice as illustrated in FIG. 3 (specific dimensions of spinneret orifice described in Example 2).

Polypropylene polymer was obtained from Shell Company (Grade 5C14). It was extruded at 279° C. A spinneret as shown in FIG. 3 was used to form 51 dpf fiber at 2,000 MPM speed. The specific dimensions of the spinneret orifices were the same as in Example 2. The quenching conditions were the same as those for obtaining PET fiber. A photomicrograph of the fiber cross-section is shown in FIG. 10 (375× magnification). The lubricant level on the fiber was 2.6%. The same lubricant as used in PET fiber was used (Example 1). The polypropylene fiber spontaneously transported the aqueous Syltint Poly Red® solution on the fiber surface. This spontaneously transportable phenomenon along the fiber surface was also observed for a 10 dpf, single polypropylene fiber. The value of the "X" parameter for this fiber was about 2.2. Polypropylene film of 0.02 inch thickness was compression molded from the same polymer as that used for making the above fiber of Example 3. The contact angle of distilled water on the above film was measured in air with a contact angle goniometer. The contact angle was about 110°. Another sample of the same film as above was sprayed with the same lubricant as used for making the fiber in this example at about the 2.6% level. The contact angle of distilled water on the polypropylene film sprayed with the lubricant was 12°. Thus, the factor $(1-X \cos \theta)$ in this case was −1.1, which is less than zero.

Example 4 (Base Fiber Preparation)

Cellulose acetate (Eastman Grade CA 398-30, Class I) was blended with PEG 400 polymer and small quantities of antioxidant and thermal stabilizer. The blend was melt extruded at 270° C. A spinneret as shown in FIG. 3 was used to form 115 dpf fiber at 540 meters/minute speed. The specific dimensions of the spinneret orifices were the same as in Example 2. No forced quench air was used. The lubricant level on the fiber was 1.6%. The same lubricant as used in the PET fibers (Example 1) was used. The cellulose acetate fiber spontaneously transported the aqueous Syltint Poly Red® solution on the fiber surface. The value of the "X" parameter for this fiber was about 1.8.

Example 5 (Comparative)

PET fiber of Example 1 was made without any spinning lubricant at 20 dpf. A single fiber did not spontaneously transport the aqueous Syltint Poly Red® solution along the fiber surface.

Example 6 (Comparative)

PET fiber of circular cross-section was made. The denier per filament of the fiber was 20. It had about 1.5% of the lubricant used in Example 1. A single fiber did not spontaneously transport the aqueous Syltint Poly Red® solution along the fiber surface.

Example 7 (Base Fiber Preparation)

Poly(ethylene terephthalate) (PET) fiber of Example 5 (without any spinning lubricant) was treated with oxygen plasma for 30 seconds. Model "Plasmod" oxygen plasma equipment was used. Exciter power was provided by the RF generator operating at 13.56 MHz frequency. The plasma treatment was conducted at a constant level of 50 watts power. The oxygen plasma treated fiber spontaneously transported the aqueous Syltint Poly Red® solution along the fiber. This fiber was tested again after washing five times and after 3 days and the spontaneously transportable behavior with the above aqueous solution was still observed. In order to determine the reduction in contact angle after the plasma treatment, a PET film of the same material as that of the fiber was subjected to the oxygen plasma treatment under the same conditions as those used for the fiber sample. The average contact angle of the oxygen plasma treated film with distilled water in air was observed to be 26° as measured by a contact angle goniometer. The corresponding contact angle for the control PET film (not exposed to the oxygen plasma) was 70°. The significant reduction in contact angle upon subjecting the untreated PET fiber to the oxygen plasma treatment rendered it to be spontaneously surface transportable for aqueous solutions.

Example 8 (Base Fiber Preparation)

Figure 12:
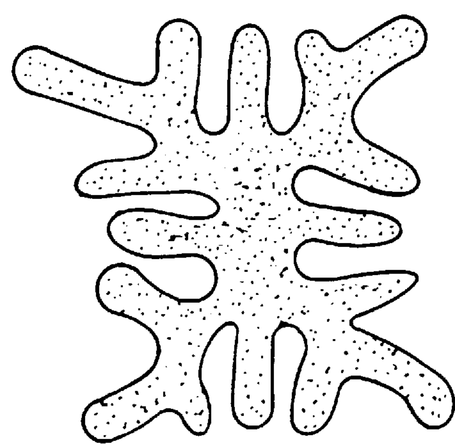
FIG. 12—schematic representation of a poly(ethylene terephthalate) fiber cross-section made using a spinneret having an orifice as illustrated in FIG. 4 (specific dimensions of spinneret orifice described in Example 8).

Poly(ethylene terephthalate) (PET) polymer of 0.6 IV was used in this example. It was extruded through a spinneret having eight orifices as shown in FIG. 4 wherein W was 0.084 mm, $X_{20}$ was 17W, $X_{22}$ was 3W, $X_{24}$ was 4W, $X_{26}$ was 60W, $X_{28}$ was 17W, $X_{30}$ was 2W, $X_{32}$ was 72W, $\theta_{10}$ was 45°, Leg B was 30W, and Leg A was 26W. The rest of the processing conditions were the same as those described in Example 1. A 100 dpf fiber was spun at 600 MPM. A sketch of the cross-section of the fiber is shown in FIG. 12. The lubricant level on the fiber was about 1%. The same lubricant as used in Example 1 was used. The above fiber spontaneously transported the aqueous Syltint Poly Red® solution along the fiber surface. The value of the "X" parameter for this fiber was 1.5.

Example 9 (Base Fiber Preparation)

Figure 13:
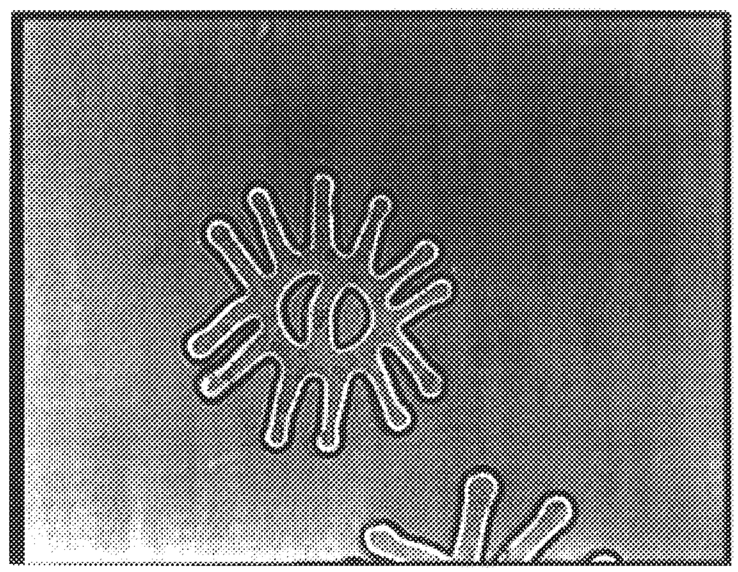
FIG. 13—photomicrograph of a poly(ethylene terephthalate) fiber cross-section made using a spinneret having an orifice as illustrated in FIG. 5 (specific dimensions of spinneret orifice described in Example 9).

Poly(ethylene terephthalate) polymer of 0.6 IV was used in this example. It was extruded through a spinneret having eight orifices as shown in FIG. 5 wherein W was 0.10 mm, $X_{34}$ was 2W, $X_{36}$ was 58W, $X_{38}$ was 24W, $\theta_{12}$ was 20°, $\theta_{14}$ was 28°, and n is 6. The rest of the extruding and spinning conditions were the same as those described in Example 1. A photomicrograph of the fiber cross-section is shown in FIG. 13 (585× magnification). A 20 dpf fiber was spun at 3000 MPM. The lubricant level on the fiber was about 1.7%. The same lubricant as used in Example 1 was used. The above fiber spontaneously transported the aqueous Syltint Poly Red® solution along the fiber surface. The value of the "X" parameter for this fiber was about 2.4.

Example 10 (Base Fiber Preparation)

Figure 14:
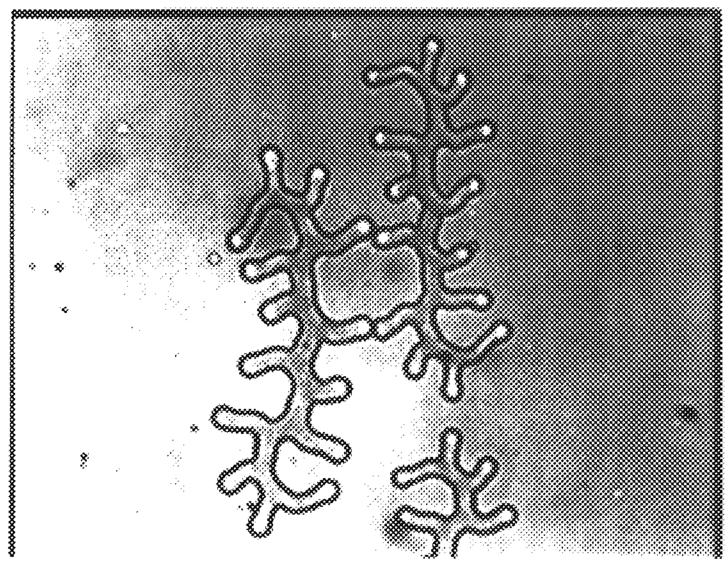
FIG. 14—photomicrograph of a poly(ethylene terephthalate) fiber cross-section made using a spinneret having an orifice as illustrated in FIG. 7 (specific dimensions of spinneret orifice described in Example 10).

Poly(ethylene terephthalate) (PET) polymer of about 0.6 IV was used in this example. The polymer was extruded through a spinneret having four orifices as shown in FIG. 7 wherein the dimensions of the orifices were repeats of the dimensions described in Example 2. The rest of the processing conditions were the same as those described in Example 1 unless otherwise stated. A 200 dpf fiber was spun at 600 MPM. The polymer throughput was about 7 lbs/hr. An optical photomicrograph of the fiber is shown in FIG. 14 (150× magnification). The lubricant level on the fiber was 2.0%. The same lubricant as used in Example 1 was used. The above fiber spontaneously transported the aqueous Syltint Poly Red® solution along the fiber surface. The value of the "X" parameter for this fiber was about 2.2.

Example 11 (Base Fiber Preparation)

Figure 8:
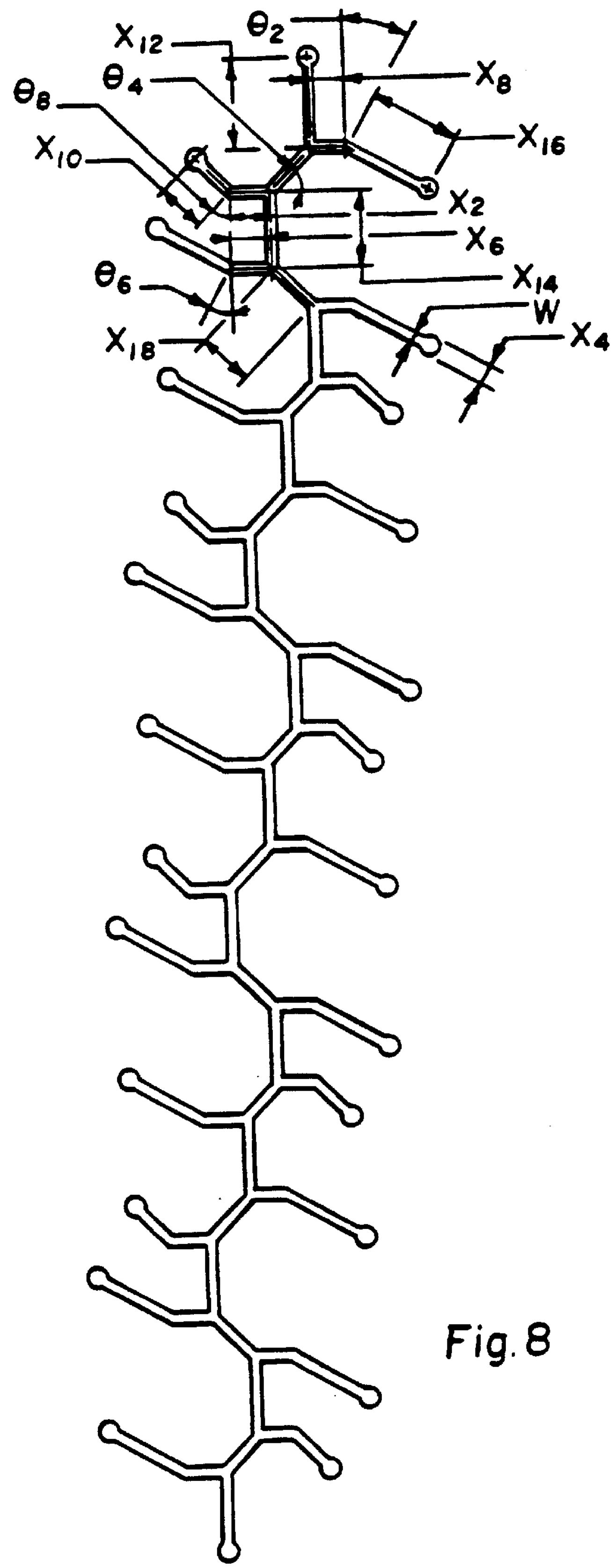
FIG. 8—schematic representation of an orifice of a spinneret having 4 repeating units, joined end to end, of the orifice as shown in FIG. 3.
Figure 15:
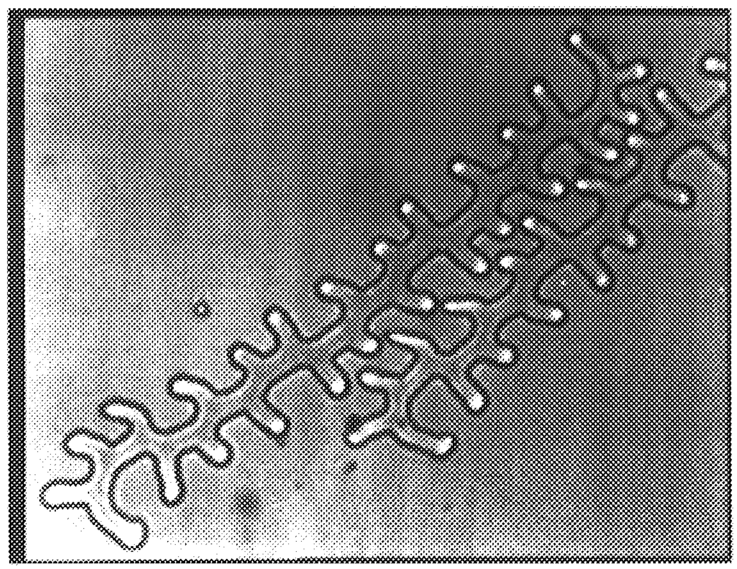
FIG. 15—photomicrograph of a poly(ethylene terephthalate) fiber cross-section made using a spinneret having an orifice as illustrated in FIG. 8 (specific dimensions of spinneret orifice described in Example 11).

Poly(ethylene terephthalate) (PET) polymer of 0.6 IV was used in this example. The polymer was extruded through a spinneret having two orifices as shown in FIG. 8 wherein the dimensions of the orifices were repeats of the dimensions described in Example 2. The rest of the processing conditions were the same as those described in Example 1. A 364 dpf fiber was spun at 600 MPM. The cross-section of the fiber is shown in FIG. 15 (150× magnification). The lubricant level on the fiber was about 2.7%. The same lubricant as used in Example 1 was used. The above fiber spontaneously transported the aqueous Syltint Poly Red® solution along the fiber surface. The value of the "X" parameter for this fiber was 2.1.

Example 12 (Base Fiber Preparation)

Figure 17:
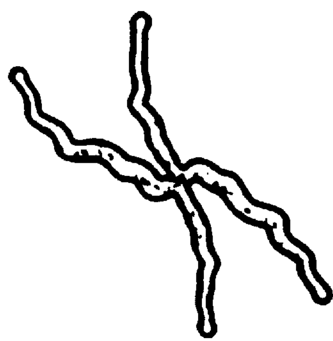
FIG. 17—photomicrograph of a poly(ethylene terephthalate) fiber cross-section made using a spinneret having an orifice as illustrated in FIG. 6 (specific dimensions of spinneret orifice described in Example 12).
Figure 17:
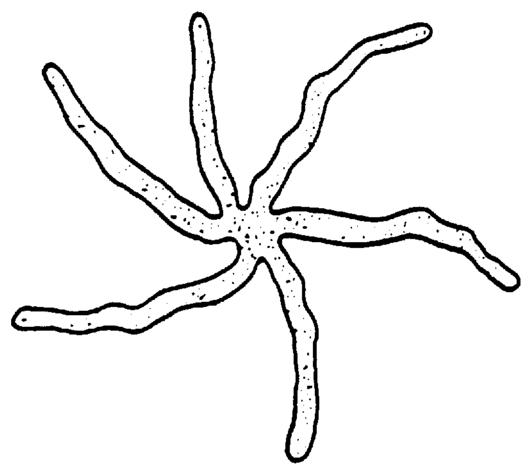

Poly(ethylene terephthalate) (PET) polymer of 0.6 IV was used in this example. It was extruded through a spinneret having eight orifices as shown in FIG. 6 wherein W was 0.10 mm, $X_{42}$ was 6W, $X_{44}$ was 11W, $X_{46}$ was 11W, $X_{48}$ was 24W, $X_{50}$ was 38W, $X_{52}$ was 3W, $X_{54}$ was 6W, $X_{56}$ was 11W, $X_{58}$ was 7W, $X_{60}$ was 17W, $X_{62}$ was 28W, $X_{64}$ was 24W, $X_{66}$ was 17W, $X_{68}$ was 2W, $\theta_{16}$ was 45°, $\theta_{18}$ was 45°, and $\theta_{20}$ was 45°. The rest of the processing conditions were the same as those described in Example 1. A 100 dpf fiber was spun at 600 MPM. The cross-section of the fiber is shown in FIG. 17. The lubricant level on the fiber was about 1%. The same lubricant as used in Example 1 was used. The above fiber spontaneously transported the aqueous Syltint Poly Red® solution along the fiber surface. The value of the "X" parameter for this fiber was 1.8.

Example 13 (Base Fiber Preparation)

PET polymer of 0.6 I.V. was used in this example. It was extruded through a spinneret having 8 orifices as shown in FIG. 6B wherein W was 0.10 mm, $X_{72}$ was 8W, $X_{74}$ was 8W, $X_{76}$ was 12W, $X_{78}$ was 8W, $X_{80}$ was 24W, $X_{82}$ was 18W, $X_{84}$ was 8W, $X_{86}$ was 16W, $X_{88}$ was 24W, $X_{90}$ was 18W, $X_{92}$ was 2W, $\theta_{22}$ was 135°, $\theta_{24}$ was 90°, $\theta_{26}$ was 45°, $\theta_{28}$ was 45°, $\theta_{30}$ was 45°, $\theta_{32}$ was 45°, $\theta_{34}$ was 45°, $\theta_{36}$ was 45°, and $\theta_{38}$ was 45°. A 20 dpf fiber was spun at 3,000 m/min. The rest of the processing conditions are the same as those used in Example 1. The lubricant level on the fiber was about 1%. The cross-section of the fiber is shown in FIG. 17B. This fiber spontaneously transported the aqueous Syltint Poly Red® solution along the fiber surface. The "X" value for this fiber is about 2.1.

Example 14 (Example of the Invention)

Figure 19:
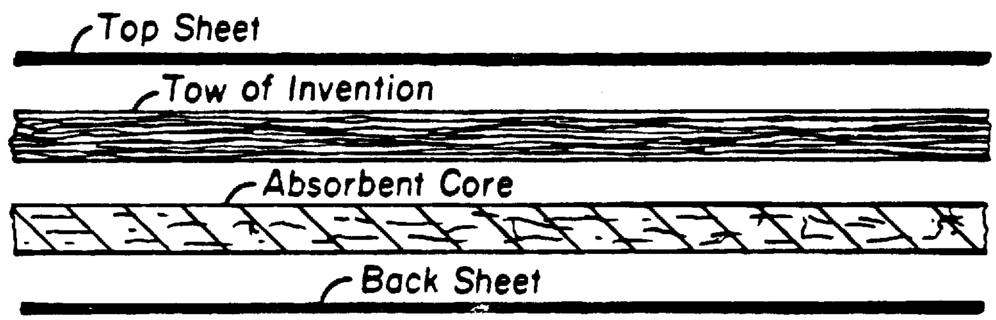
FIG. 19—a schematic representation of an exploded side view of a diaper along the major axis of the diaper. The tow made from fibers of the present invention is placed below the top sheet and above the absorbant core.

A disposable absorbant article is prepared comprising (a) a liquid impervious backing sheet made of polyethylene, (b) a relatively hydrophobic, liquid pervious top sheet made of polypropylene, (c) a layered absorbant core positioned between said backing sheet and said top sheet, and (d) tow or fibers of the present invention. The cover or facing provided on the absorbant structure is a non-woven fabric having a high degree of moisture permeability. For example, the fabric may be polyester, polyethylene, polypropylene, nylon, rayon, or the like. Preferably, the fabric used for the cover is a lightweight fabric in the range of 0.3 to 5.0 oz./square yard and with a density less than 0.3 g/cc. The most suitable fabrics have unusually high elongation, softness, and drape characteristics. Though the cover is moisture permeable, it is preferably of the type which after permeation of the moisture prevents strike-back of the body fluid when the absorbant structure is approaching saturation. The body of the cellulosic fibrous batt (fluff pulp) is substantially more wettable than the cover and tends to draw liquid away from the facing layer. The cellulosic batt may be wrapped in a tissue. It may not be necessary to have a tissue wrapping the cellulosic batt. However, if the cellulosic batt is quite thick, such as an inch or more, it may be desirable to provide a tissue wrap to assist with maintenance of the desired shape of the absorbant structure. The cellulosic batt also contains a water-swellable, water-insoluble absorbant composition. The superabsorbant particles are generally in the form of a dry solid water-swellable, water-insoluble absorbant composition such as an ionic complex of a water-soluble anionic polyelectrolyte and a polyvalent metal cation. Typical superabsorbant compositions are illustrated in U.S. Pat. No. 4,090,013 to S. H. Ganslaw et al. and U.S. Pat. No. 4,043,952 to S. H. Ganslaw et al. The superabsorbant material may be in the form of individual particles or strips of film to which the superabsorbant material is adhered to other known superabsorbant compositions. The superabsorbant material may be affixed to the base of the superabsorbant reservoir or may simply lie independently within the reservoir. The fibers of the present invention may be placed in a tow form or fiber bundle immediately below the top sheet as shown in FIG. 19. By using the tow of the fibers of the present invention, the body fluid (e.g., urine) will be spread farther along the absorbant article (thus improving the strikethrough and rewet properties), thereby more effectively utilizing the available absorbant area and superabsorbant material and resulting in a drier skin-absorbant article interface.

Example 15 (Example of the Invention)

Figure 21:
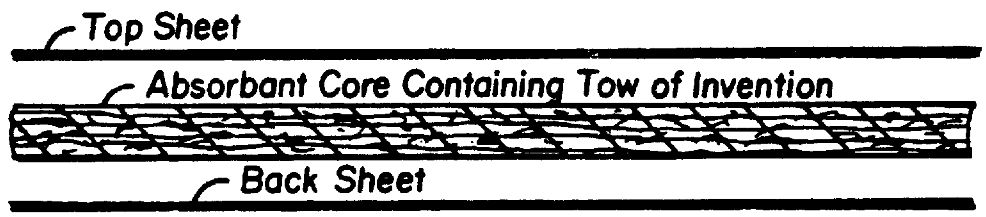
FIG. 21—a schematic representation of an exploded side view of a diaper along the major axis of the diaper. The tow made from fibers of the present invention is placed within the absorbant core.

The components of the disposable absorbant article are the same as in Example 14. However, in this case the fibers of the present invention are placed in a tow form within the cellulosic batt (absorbant core) as shown in FIG. 21. By using the tow of the fibers of the present invention, the body fluid (e.g., urine) will be spread farther along the absorbant article (thus improving the strikethrough and rewet properties), thereby more effectively utilizing the available absorbant area and superabsorbant material and resulting in a drier skin-absorbant article interface.

Example 16 (Example of the Invention)

Figure 20:
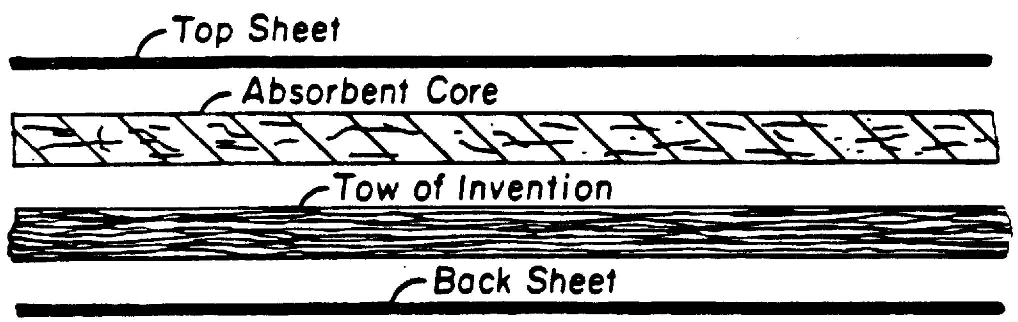
FIG. 20—a schematic representation of an exploded side view of a diaper along the major axis of the diaper. The tow made from fibers of the present invention is placed below the absorbant core and above the back sheet.

The components of the disposable absorbant article are the same as in Example 14. However, in this case the fibers of the present invention are placed in the tow form immediately below the cellulosic batt (absorbant core) as shown in FIG. 20. By using the tow of the fibers of the present invention, the body fluid (e.g., urine) will be spread farther along the absorbant article (thus improving the strikethrough and rewet properties), thereby more effectively utilizing the available absorbent area and superabsorbant material and resulting in a drier skin-absorbant article interface.

Example 17 (Example of the Invention)

The components of the disposable absorbant article are the same as in Example 14. However, in this case the fibers of the present invention are placed in the layer containing the cellulosic batt (absorbant core). There is an intimate blend of the staple fiber of the present invention and fluff pulp (hydrophilic cellulosic fiber). The fibers of the present invention are in cut, staple form 0.25 inch to 6 inches in length (see FIG. 22). By using the tow of the fibers of the present invention, the body fluid (e.g., urine) will be spread farther along the absorbant article (thus improving the strikethrough and rewet properties), thereby more effectively utilizing the available absorbant area and superabsorbant material and resulting in a drier skin-absorbant article interface.

Example 18 (Example of the Invention)

Figure 26:
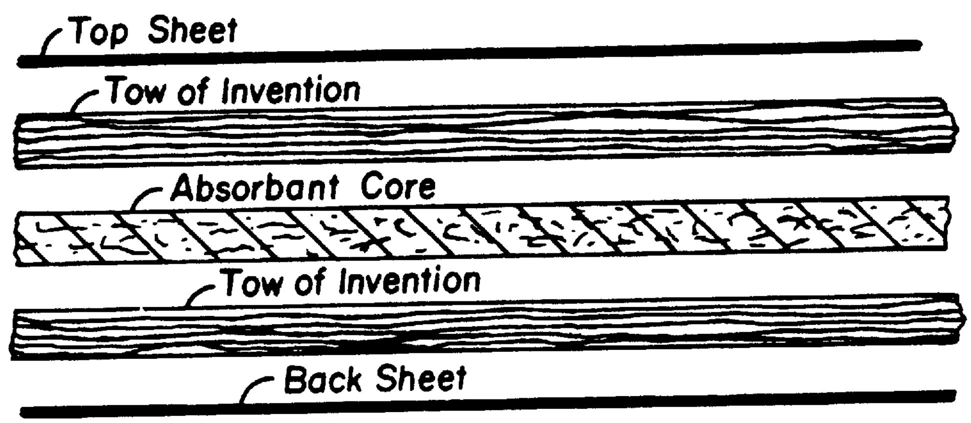
FIG. 26—a schematic representation of an exploded side view of a diaper along the major axis of the diaper. The tow made from fibers of the present invention is placed above and below the absorbant core.

The components of the disposable absorbant article are the same as in Example 14. However, in this case the fibers of the present invention are placed in the tow form above and below the cellulosic batt (absorbent core) as shown in FIG. 26. By using the tow of the fibers of the present invention, the body fluid (e.g., urine) will be spread farther along the absorbant article (thus improving the strikethrough and rewet properties), thereby more effectively utilizing the available absorbant area and superabsorbant material and resulting in a drier skin-absorbant article interface.

Example 19 (Example of the Invention)

The components of the disposable absorbant article are the same as in Example 14. However, in this case the fibers of the present invention are in the tow form and tightly compacted in the impingement zone (the tow may also be twisted in the impingement zone) such that the fibers are substantially in contact with each other (thereby promoting rapid movement of urine or other bodily fluids along the fiber axis due to the combined action of the spontaneous surface transportable nature of these single fibers and the capillary flow in the void space between the fibers), and toward each end of the length of the article the fibers of the tow flare and are substantially not in contact with each other. One possible arrangement is shown in FIG. 24. This arrangement will allow rapid movement of urine from the impingement zone to the outer areas of the diaper. By using the tow of the fibers of the present invention, the body fluid (e.g., urine) will be spread farther along the absorbant article (thus improving the strikethrough and rewet properties), thereby more effectively utilizing the available absorbant area and superabsorbant material and resulting in a drier skin-absorbant article interface.

Example 20 (Example of the Invention)

Tows of this invention are very useful for making ink reservoir cartridges for writing instruments which utilize aqueous based inks. 96/8 d/f PET yarns were made using the conditions of Example 1 except the lubricant level was 3.4%. These yarns were plied, drafted 1.5X, thermally stabilized, crimped and pulled into cylindrical cartridges (0.70 cm in diameter) such that the density in the cartridges ranged from about 0.10 g/cc to about 0.25 g/cc. Appropriate round cross-section PET control was made at 8 dpf with 1% of the lubricant used in Example 1, crimped and pulled into the same size cylindrical cartridges such that the densities ranged from about 0.10 g/cc to about 0.25 g/cc. These cylindrical cartridges were cut to lengths of 7.95 cm and all of the testing was done using Sheaffer Skript® writing fluid, washable black #632.

Figure 27:
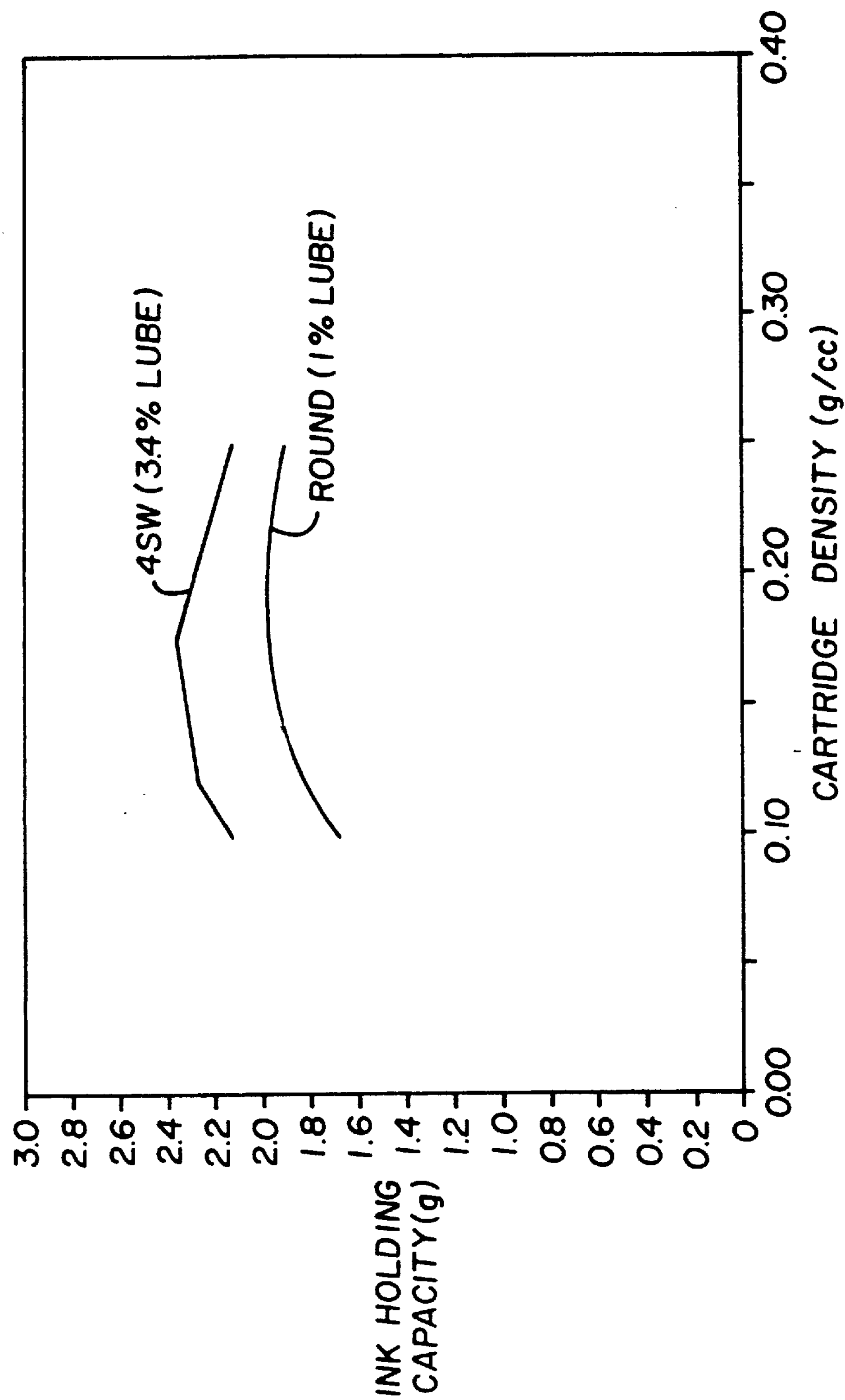
FIG. 27—graph of the ink holding capacity in grams (g) versus cartridge density in grams per cubic centimeter (g/cc) for an ink cartridge made from fibers of the present invention (line labeled "4SW") and for an ink cartridge made from fibers of the prior art of round cross-section (line labeled "round").

FIG. 27 shows the ink holding capacity versus cartridge density for cartridges made from fibers of the present invention and round fiber controls. This test basically involved dripping ink into the cartridges of known weight held in a vertical position and determining the amount of ink the cartridge held when it began to drip from the bottom of the cartridge. This weight in grams was called the ink holding capacity of the cartridge being tested. The improvement ranged from about 13% to 26% over the range of densities tested.

Figure 28:
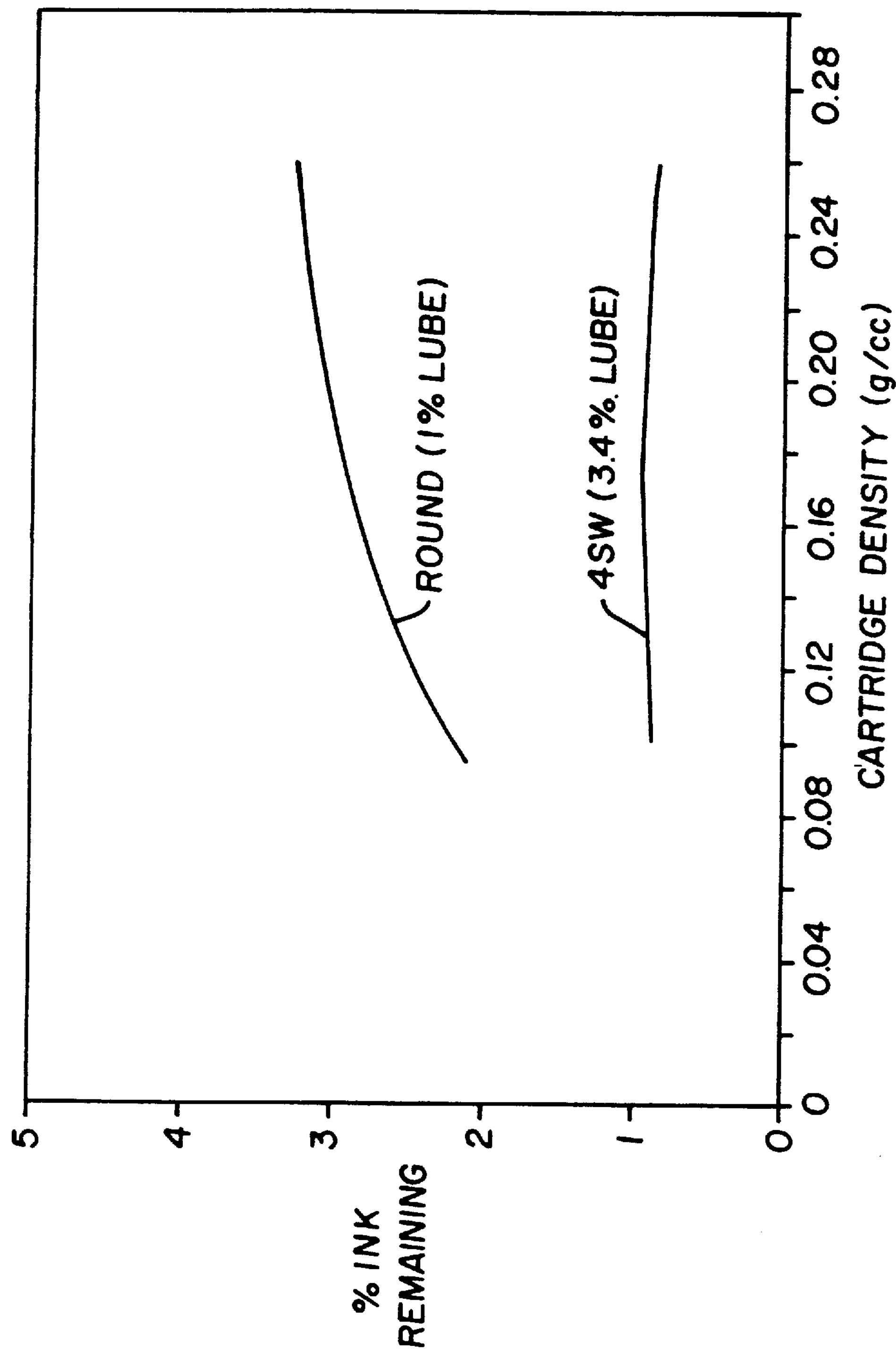
FIG. 28—graph of the percent ink remaining versus cartridge density (g/cc) for an ink cartridge made from fibers of the present invention (line labeled "4SW") and for an ink cartridge made from fibers of the prior art of round cross-section (line labeled "round").

FIG. 28 shows the percent ink remaining versus cartridge density for cartridges made from PET fibers of the present invention and round PET fiber controls. Percent ink remaining was defined as ink remaining in the cartridge after dewicking (g)/ink holding capacity (g)×100 where the ink remaining in the cartridge after dewicking was determined by weighing the cartridge, filling it with ink (ink holding capacity), weighing the cartridge plus ink, contacting the bottom of the cartridge with Type F2 Buckeye Filter paper and dewicking until such time as no ink left the cartridge, weighing the cartridge plus ink remaining and finally subtracting the weight of the cartridge to determine the weight in grams of the ink remaining in the cartridge. Notice the clearly superior behavior of the cartridge containing fibers of the present invention.

Figure 29:
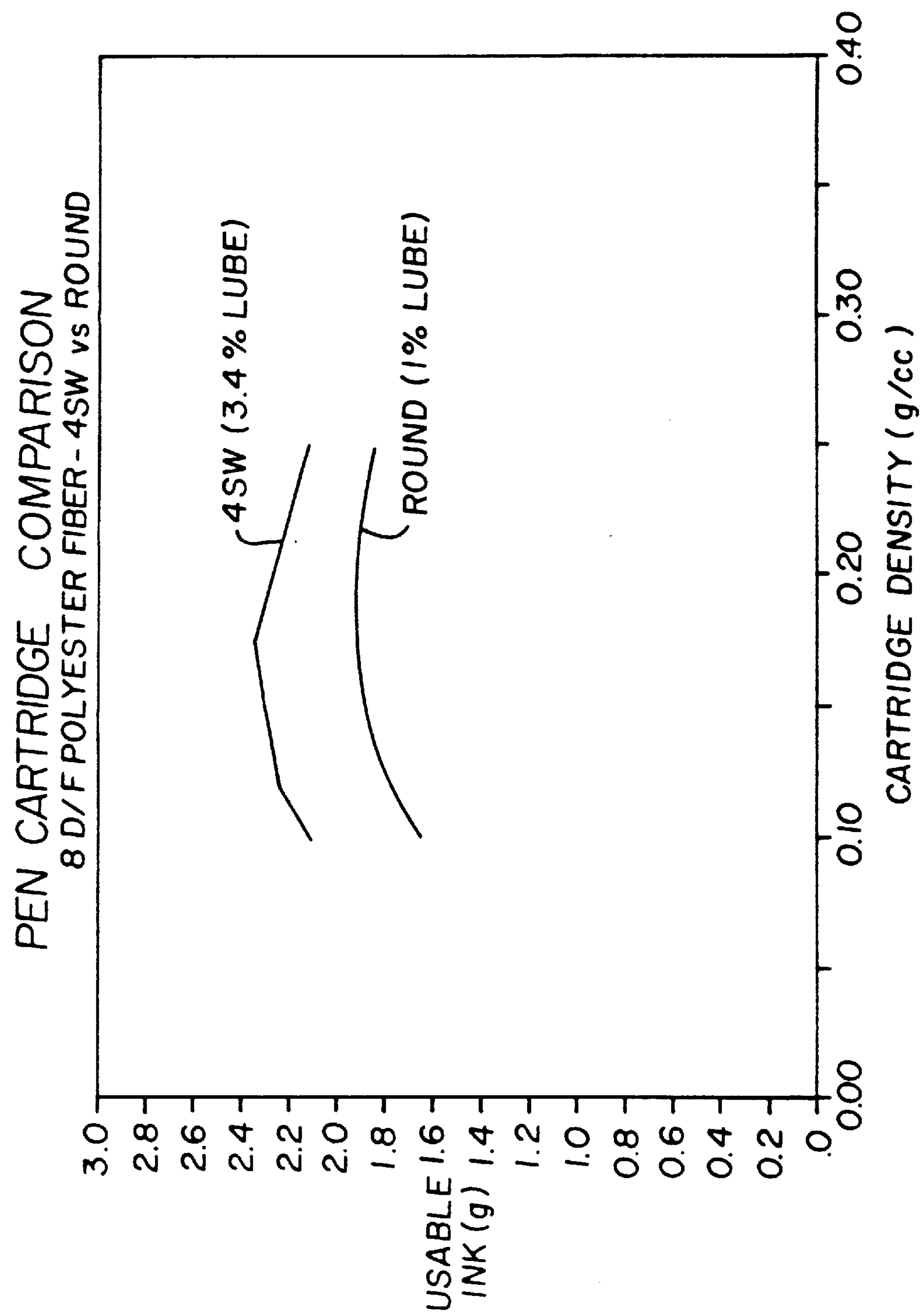
FIG. 29—graph of the useable ink (g) versus cartridge density (g/cc) for an ink cartridge made from fibers of the present invention (line labeled "4SW") and for an ink cartridge made from fibers of the prior art of round cross-section (line labeled "round").

FIG. 29 shows useable ink versus cartridge density for cartridges made from fibers of the present invention and round fiber controls. This test involved dripping ink into the cartridge of known weight such that its ink holding capacity was equaled, contacting the bottom of the cartridge with Type F2 Buckeye Filter paper and dewicking until such time as no ink left the cartridge, weighing the cartridge plus unavailable ink and subtracting the weight of the unavailable ink (g) from the ink holding capacity (g) to determine the useable ink in grams. The improvement range from about 15% to about 30% over the range of densities tested.

Figure 30:
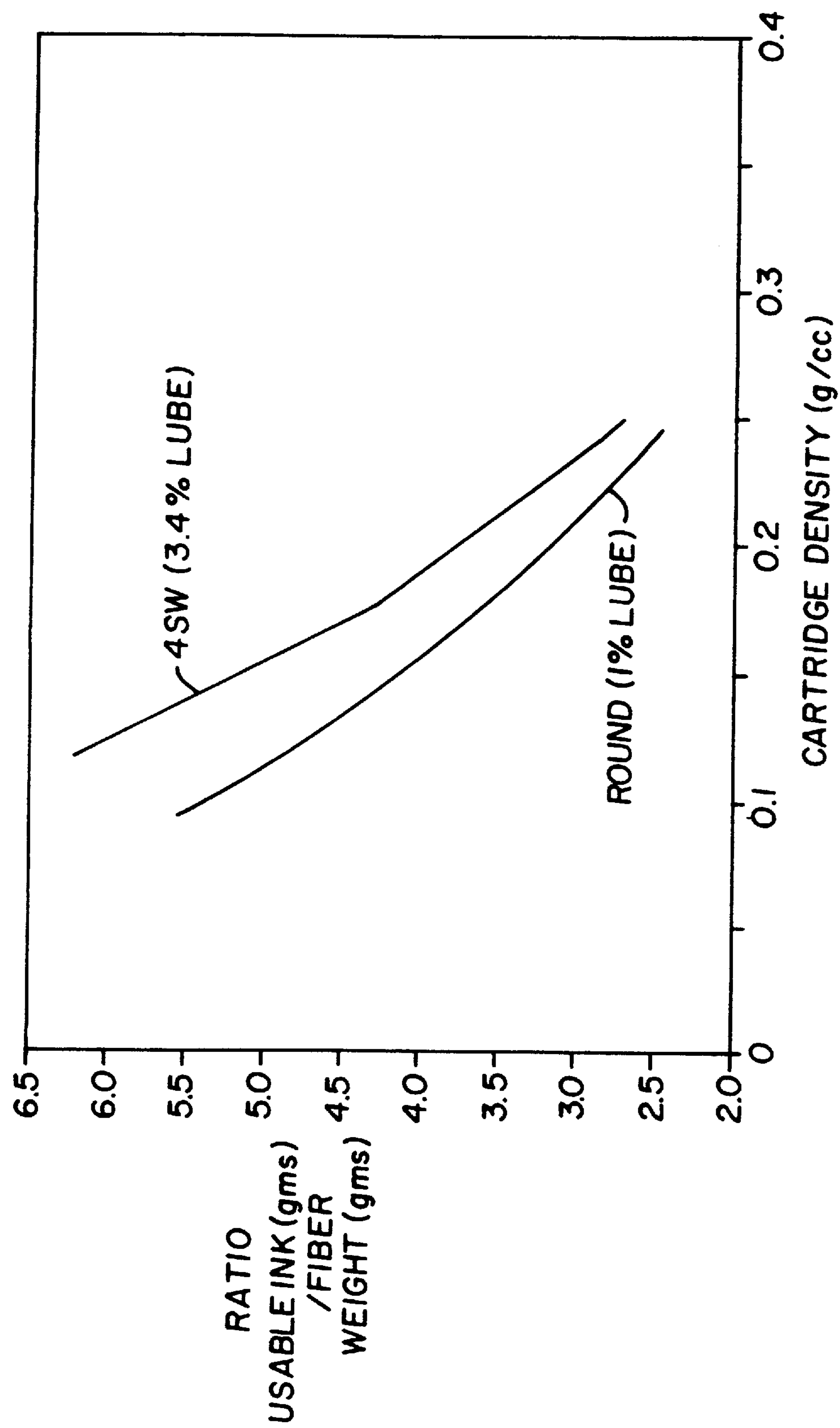
FIG. 30—graph of the ratio of useable ink (g)/fiber weight (g) versus cartridge density (g/cc) for an ink cartridge made from fibers of the present invention (line labeled "4SW") and for an ink cartridge made from fibers of the prior art of round cross-section (line labeled "round").

FIG. 30 shows the ratio of useable ink to fiber weight versus cartridge density for cartridges made from fibers of the present invention and round fiber controls. Notice the significant improvement of the cartridges made from fibers of the present invention.

Example 21—Uphill Flux Test

Scope and Significance

This method is used to determine the fluid transport rate of capillary transport materials from a reservoir of synthetic urine fluid along an incline to an absorbant. This computer monitored version of the method automatically measures the fluid uptake of the test materials and provided a profile of the weight gain of the transport and absorbant storage materials with time. The spontaneous movement of the fluid up the incline and through the transport material is a quantitative measure of the surface and capillary forces acting on the fluid in opposition to gravity. Uphill transport testing provides a means of comparing rate differences due to the type and size of capillary transport materials as well as surface treatments and geometries. The test can also be used to evaluate the effects of test fluid surface tension as well as different absorbant materials. Finally, the test can be modified to simulate in-use conditions such as removing the reservoir and replacing it later to simulate multiple urine additions.

Summary of Method

The uphill transport test is used to determine the fluid transport rate of capillary transport materials from a reservoir of synthetic urine test fluid along a 20 cm long ramp to an absorbant on an attached platform at 10 cm height. Once the prepared specimen is mounted on the platform/incline, the operator initiates the test according to the instructions given by the computer program by placing the lower end of the transport material in the reservoir of fluid. The test continues for 90 minutes or until terminated by the operator.

Definitions

The terms employed in this method are commonly used in normal laboratory practice and require no special comment.

Safety Precautions

Normal safety precautions and safe handling practices should be observed.

Sources of Error

Fluid transport is very surface and geometry dependent. Surface contamination should be avoided and sample handling should be minimized.

Condition all fiber and fabric samples, including the storage or absorbant material, at least overnight in the laboratory before testing so that the moisture content is controlled by the relative humidity in the laboratory.

The balance is very sensitive to fluid movement in the two reservoirs. Because the fluid transported by the test specimen is the measured response of the test, an accurate tare weight of the fluid before the test is started is essential. The computer does not take this tare weight reading until the specimen to be tested has been identified to the computer and the label is accepted as correct by the operator. Therefore, prior to this time in the program, adjustments in the specimen or test apparatus can be made without affecting the results. All adjustments must be made prior to this point in the testing procedure.

Apparatus

Figure 39:
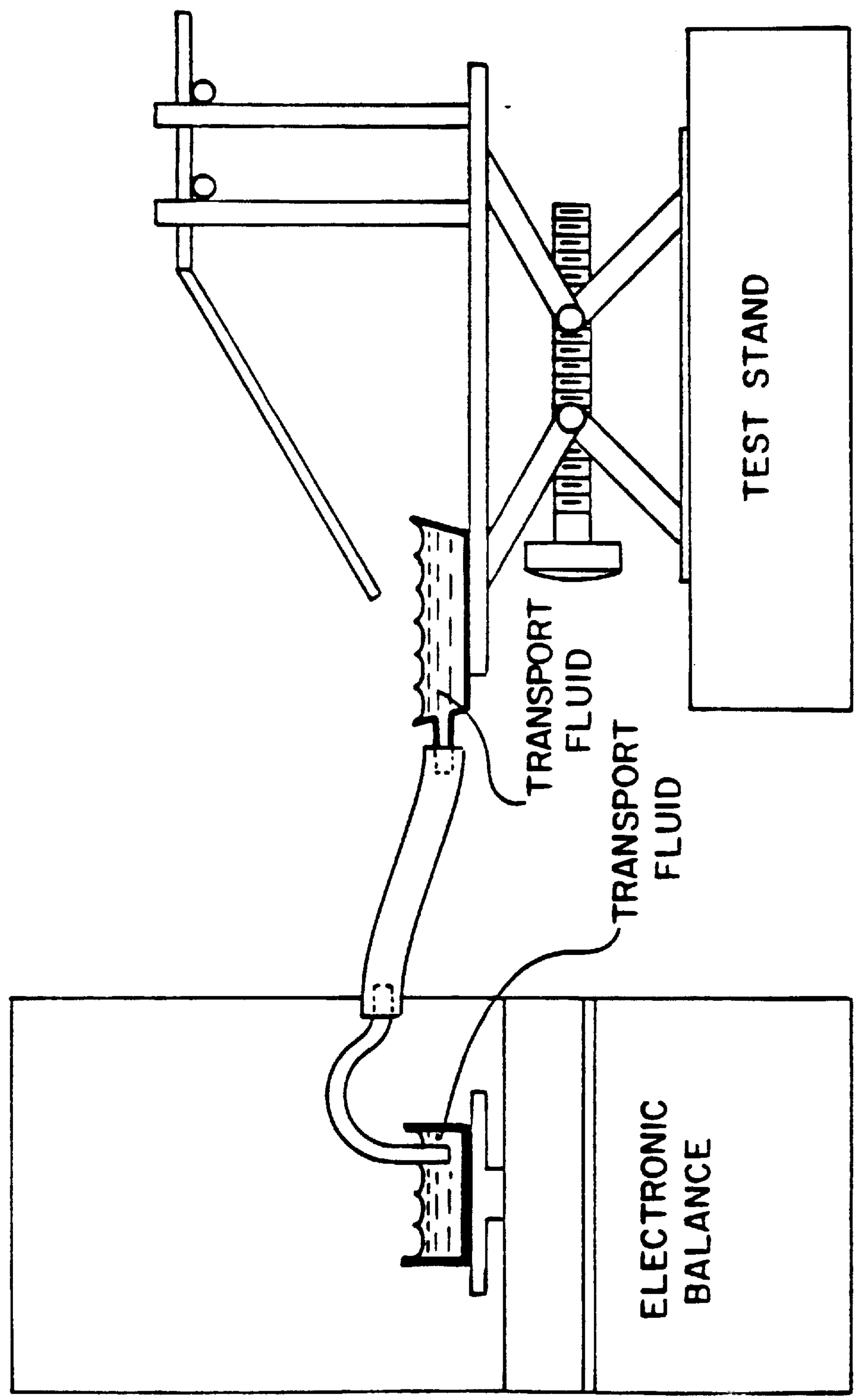
FIG. 39—a schematic representation of the apparatus used to determine uphill flux.

A schematic representation of the apparatus used is in FIG. 39.

Reagents and Materials

- SYN-URINE test fluid from Jayco Pharmaceuticals (dyed with food coloring to aid observation)
- Transport material of choice, in most cases this will be a sheet of PET filaments
- Absorbant or storage material, such as Bounty® towels or diaper core sections Calibration and Standardization Sample Preparation Weigh a quantity of transport material precut to 40 cm length. Pull out a 20 cm length of Saran Wrap from its 12-inch wide dispenser box. The 11 ½-inch wide roll of wrap is just the right size to place around the transport material from the bottom or back side to the top side with the ends of the wrap just meeting on the top for minimum overlap (⅛–¼ inch). Wrap loosely with Saran Wrap with about 5 cm of transport material sticking out from the end to be placed in the reservoir and with 15 cm sticking out from the end to be placed in the absorbant. The resulting area of transport material covered with wrap will be 20 cm length by 5 ½ inch width. This covering minimizes evaporation from the transport material between the reservoir and the absorbant. Cut the absorbant material of choice to 6 inch×6 inch size.

Mount the covered transport material on the ramp with its previously assembled absorbant or assemble the transport material/absorbant layers on the ramp. Be sure the filled reservoir has been previously covered with stiff paper or cardboard so the 5 cm tail of the transport material will not enter the fluid until the computer has been set up and is ready to start the data collection process. Once the absorbant is in place on the horizontal part of the ramp, apply a load weight over the absorbant (usually 0.1 psi).

Procedure

After turning on the computer, note the test menu and the C> prompt. Type “date” and enter the current date [Return]. Type “UP” to start the test program. Follow the instructions on the computer screen. Stop after you have labeled the sample to be tested. Accepting the labeling as correct will cause the computer to read the balance, and this must not occur until the balance has stabilized with the test specimen and any weights completely in place.

The test is started once the balance is stable by removing the reservoir cover and allowing the transport material to enter the transport fluid. Press [Return] when this occurs to start the computer program that collects the weight data.

The computer program is designed so that two transport processes are followed. The first one is when the fluid moves up the incline of the ramp until the fluid front just reaches the absorbant at the top of the incline. This is the “induction” process. The computer must know when the fluid reaches the absorbant material. Pressing the F5 key tells the computer to calculate the induction process and to begin collecting data for the “transport” process that occurs as the fluid moves in the absorbant material at the top of the ramp.

At the end of the test (90 minutes total or sooner if the test is terminated by the operator) enter the weight of the transport material as requested by the computer. The computer calculates the appropriate times and flux values and puts the results on the printer. The computer is programmed in any conventional way to carry out these calculations. The specific program used in the Examples of this invention is exemplified in Example 24.

Example 22—Measurement of Adhesion Tension

This describes the measurement of adhesion tension between a liquid and the surface of a polymer film. The adhesion tension at a solid-liquid-air interface is defined as the force per unit length of interface exerted on the solid surface in the plane of the surface and normal to the interface. The apparatus used here consists of a Cahn 2000 Recording Microbalance with a resolution of about 0.1 $\mu$g and a Rame Harte Vertical Platform Assembly, which moves vertically at uniform speeds down to a fraction of a micron per second.

About 50 ml of the liquid of interest is placed beneath the microbalance on the platform in a cylindrical container with a diameter of about 5 cm. A rectangular sample approximately 1 cm by 2 cm is cut from the polymer film with shears or with a razor knife depending on the thickness of the film. The sample should be flat and of uniform thickness and must be relatively rigid. It is important that the edges be straight, square and sharp and that the surface be free of fingerprints or other contamination. The sample is suspended from the microbalance by means of a small hook fastened with glue or tape to the center of one of the short edges. The hook should be bent gently so that the sample hangs vertically with its bottom edge parallel to the liquid surface, and the liquid container should be centered beneath it. The platform is raised by means of a coarse motor until the liquid surface is within 1 mm but not touching the bottom edge of the film. The alignment and position of the film may be easily determined by observation of the reflection of the film edge in the liquid surface. After adjustment of the microbalance to tare away the weight of the sample the net force is recorded as an apparent mass reading. The fine motor on the platform is then used to raise the liquid surface at a speed of about 2.5 μm per second. When the liquid makes contact with the film edge a force due to the adhesion tension is recorded. By means of the continued elevation of the platform the film is slowly immersed to a depth of about 0.4 cm at which point the test is discontinued and the platform is returned to its initial level.

During the immersion, random fluctuations in the force are observed due to inhomogeneities on the film surface while the average force decreases gradually because of the effect of buoyancy. The wetting force is determined by extrapolation of a line drawn through the force reading back to the point where initial contact of the film with the surface was made. At this point buoyancy does not contribute to the force. The perimeter of the film edge is then determined by careful measurement of the length of the bottom edge and the thickness of the film by means of a caliper and micrometer. The adhesion tension is calculated according to the following formula:

$$a = \frac{mg}{2(w+t)}$$

where a=adhesion tension, dyne/cm m=balance reading, g g=acceleration of gravity (=977.2 cm/sec$^2$ at Kingsport, Tenn.)

w=width of bottom edge of sample, cm t=film thickness, cm

Example 23—(TABLE II)

This is a comparative example which shows the surprisingly strong influence of increasing the adhesion tension from 32 to 60 dynes/cm on the uphill flux for a series of different spontaneously wettable fibers. Sample 001-4B was identical to 001-7B except that 001-4B had 0.5% 70% PEG 600 monolaurate and 30% potassium lauryl phosphate applied during spinning. This finish obviously inhibited an effective plasma treatment on the sample. Compare the other paired samples to see the dramatic increase in fluxes by increasing the adhesion tension. The specific dimensions for the spinneret orifice of FIG. 35 were as follows: $W_1$=100 microns, θ=90°, S=10, R=50, T=20, U=1.3, V=50 (see FIG. 33). The specific dimensions for the spinneret orifice of FIG. 36 were as follows: $W_1$=100 microns, θ=90°, S=10, R=50, T=10, U=1.3, V=50 (see FIG. 33).

Example 24

Figure 54:
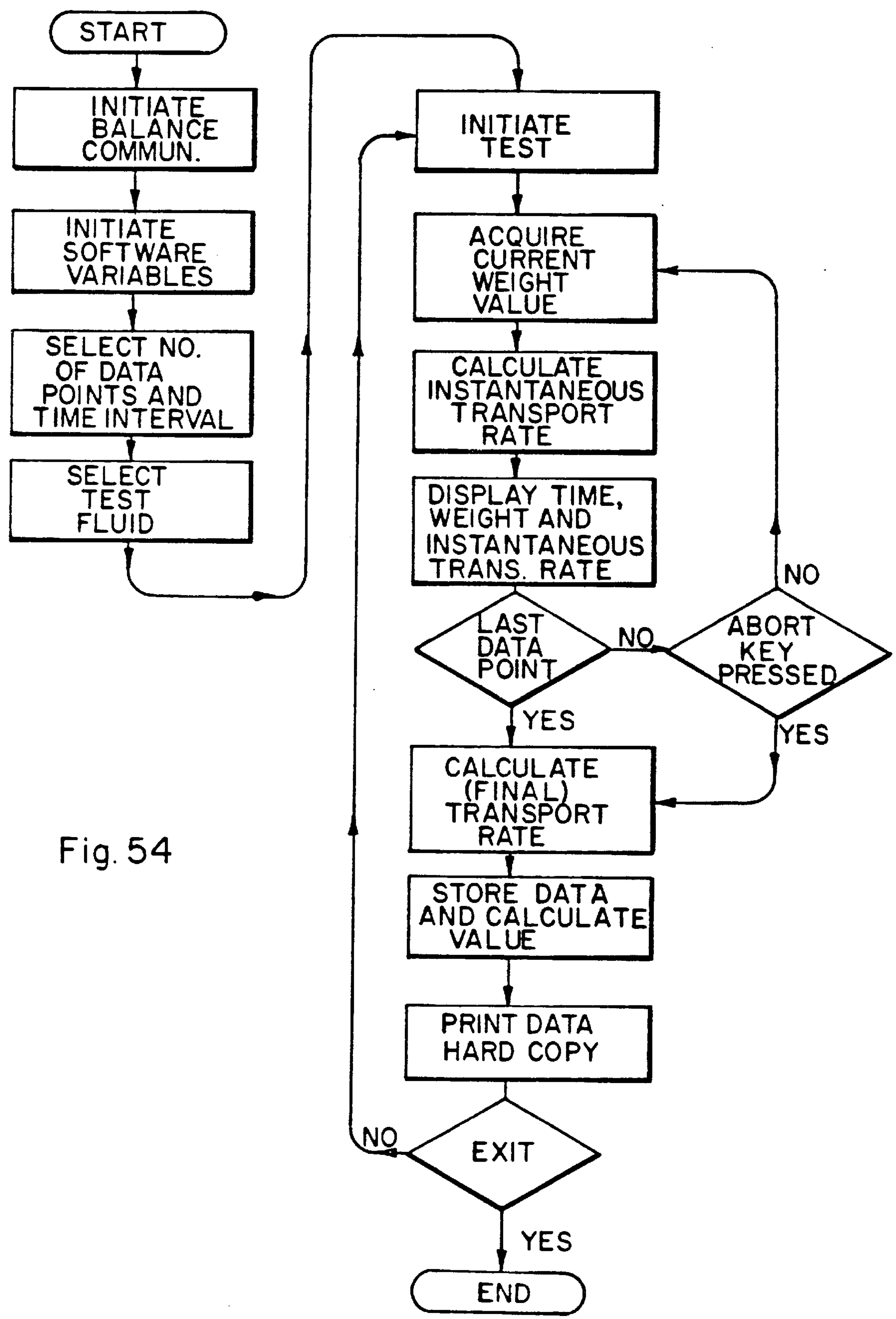
FIG. 54—a schematic representation of the programming of the computer used in the uphill flux test.

Any computing means can be used in the uphill flux test provided that it has enough memory and speed. The computer is programmed in any conventional way to carry out the steps of the uphill flux test. The programming will be apparent from the previous description. A useful summary of the program is set forth in FIG. 54.

The specific computer program used specifically in the uphill flux test used in this invention is incorporated herein as follows:

Language is Microsoft "Quick Basic".

```
                File:   UP.BAS

DECLARE SUB LIMITS (DAT!(), TM!, AVE!, LIMFLG!)
DECLARE FUNCTION DSKFUL! ()
DECLARE SUB WIN (r!, c!, max!, array$(), FLG!)
    '************************( UPHILL,BAS )*************************
    'The software for the UPHILL FIBER FLUX TEST for testing
    'competitive fiber samples in a wetting applications. (Ex. -
    'disposable diapers)
    '***************************************************************
    '
    '
                DIM DATUM(730)
                DIM TBUF$(730), MESS$(10), AFILE$(18), B$(255),
                DESC$(200)

    '****( Set ERROR trapping )****
              ON ERROR GOTO ERTRAP
    '****( Set EXIT function trap for F1 )****
                ON KEY(1) GOSUB TEXIT
                KEY(1) ON
                COLOR 15, 0, 0
    '****( Initialize RS232 port for Balance communications )****
                OPEN "COM1:2400,E,7,1,CS,CD,DS,RS,LF" FOR RANDOM AS #1
    '
    '****(Disable Control Bar on balance to stop errors)****
                PRINT #1, "R1"; CHR$(13); CHR$(10);
    '
    ' ****( WIND Data points taken at TI seconds intervals )****
    '
DATAST:         CLS
                MESS$(1) = "                  UPHILL FLUX TEST         "
                MESS$(2) = "           ---< DATA INTERVAL SETUP >---   "
                MESS$(3) = "               1. NUMBER OF POINTS         "
                MESS$(4) = "               2. TIME BETWEEN POINTS      "
                CALL WIN(1, 1, 4, MESS$(), 0)
                PRINT
```

```
DSTA:           PRINT "Enter time between data points;"
                PRINT "       Choose 60,120,180,240,300,or 360
                seconds"
                INPUT "                             Default = 60
                seconds: ", AAA$
                IF (VAL(AAA$) = 0) THEN TI = 60 ELSE TI = VAL (AAA$)
                SELECT CASE TI
                      CASE IS = 60
                            GOTO DSTB
                      CASE IS = 120
                            GOTO DSTB
                      CASE IS = 180
                            GOTO DSTB
                      CASE IS = 240
                            GOTO DSTB
                      CASE IS = 300
                            GOTO DSTB
                      CASE IS = 360
                            GOTO DSTB
                      CASE ELSE
                            GOTO DSTA
                END SELECT
DSTB:           PRINT : PRINT "Enter maximum no. of data points;"
                INPUT "Choose 15 - 720 points; Default = 15 points: ",
                AAA$
                IF (VAL(AAA$) = 0) THEN WIND = 15 ELSE WIND =
                VAL(AAA$)
                IF (WIND < 15 OR WIND > 720) GOTO DSTB
                TOTIME = WIND * TI: HR = INT(TOTIME / 3600)
                MIN = INT((TOTIME - 3600 * HR) / 60)
                SEC = (TOTIME - HR * 3600 - MIN * 60)
                PRINT
                PRINT "The maximum test time chosen  = "; HR;
                " hours "; MIN;
                PRINT " minutes "; SEC; " seconds."
                PRINT
                INPUT "IS THIS CORRECT? ", AAA$
                IF AAA$ = "n" OR AAA$ = "N" THEN GOTO DATAST
                DR$ = "": A1$ = "": A2$ = "": REM INIT DATA FILE NAMES
     '****( Show title screen and Prompt for disk in drive b: )****
START:          CLS
                GOSUB TITLE
                FOR I = 1 TO 3
                PRINT
                NEXT I
                GOSUB BELL
                GOSUB CLKSET
                FOR I = 1 TO 2
                PRINT
                NEXT I
INSERT:         PRINT "                 INSERT diskette in Drive A:"
                INPUT "                 Press <ENTER> - - - ", AAA$
                OPEN "A:\UPHILL.CFG" FOR OUTPUT AS #2: CLOSE #2
                GOSUB WARN
    '
    '****( General instructions )****
                CLS
                GOSUB INSTRUCT
    '
    '****( Chk. Disk Capacity & Prepare Operator )****
PREP:           CLS : LOCATE 12, 2: PRINT "Please Wait, Checking Disk
                Space..."
```

```
                  WHILE DSKFUL < (2 * TOTIME * 35 / 60)
                        CLS
                        MESS$(O) = " DISK FULL: Insert New Diskette ! "
                        CALL WIN(0, 0, 1, MESS$(), -1)
                  WEND
                  CLS
                  MESS$(1) = " Prepare Siphon and Sample. "
                  MESS$(2) = "                              "
                  MESS$(3) = " (DO NOT Place sample into solution). "
                  CALL WIN(0, 0, 3, MESS$(), -1)
      '
      '****( Get Preliminary Information & Name Data File )****
                  CLS
                  LOCATE 11, 1
                  GOSUB BELL
                  INPUT "Do You Wish to See the Files on drive A:
                  [Y/N]? ", ANS$
                  IF ANS$ <> "Y" AND ANS$ <> "y" GOTO FILENM
                  FILES "A:"
                  PRINT
                  INPUT "Press <ENTER> to Continue", ANS$
FILENM:           CLS : PRINT : PRINT : PRINT
                  FILREDO = 0: '''INIT CORRECTION FLAG
                  PRINT "Enter notebook, page & sample numbers as
                  shown - "
                  PRINT " (Example: X10621-049-35B)"
                  INPUT "          (notebk)-(pag)-(smp) ===> ", NBOOK$
                  IF LEN(NBOOK$) <> 14 THEN GOTO FILENM
                  PREDR$ = LEFT$(NBOOK$, 6)
                  IF (RIGHT$(PREDR$, 1) = "-") THEN GOTO FILENM
                  PREDR$ = "A:\" + PREDR$
                  IF (PREDR$ = DR$) THEN GOTO FNMA
                  DR$ = PREDR$
                  CHDIR "A:\": CHDIR DR$
                  IF ERRBUF = 75 OR ERRBUF = 76 THEN
                        MKDIR DR$: CHDIR DR$: ERRBUF = 0
                  ELSE GOTO FNMA
                        END IF
FNMA:             A1$ = MID$(NBOOK$, 8, 3)
                  A2$ = RIGHT$(NBOOK$, 3)
                  IF (LEFT$(A1$, 1) = "-" OR RIGHT$(A1$, 1) = "-") THEN
                  GOTO FILENM
                  IF (LEFT$(A2$, 1) = "-" OR RIGHT$(A2$, 1) = "-") THEN
                  GOTO FILENM
                  AFILE$ = DR$ + "\" + A1$ + "." + A2$
                  OPEN AFILE$ FOR OUTPUT AS #2
                  IF ERRBUF = 75 THEN
                        ERRBUF = 0: PRINT : PRINT
                        INPUT "File Already Exists; Press <ENTER> to try
                        again...", AAA$
                        GOTO FILENM
                        END IF
                  CLOSE #2
                  PRINT : PRINT "File name created: "; AFILE$
                  IF (FILREDO) GOTO FNMD
FNMB:             INPUT "Enter short description (<200 char.): ", DESC$
                  PRINT : PRINT : PRINT "Is the above information
                  correct?"
FNMD:             PRINT " Enter: "
                  PRINT "      0 - No correction."
                  PRINT "      1 - For Notebook no. correction."
                  PRINT "      2 - For description correction."
```

```
                INPUT "->", BBB$
                FILREDO = 1 + VAL(BBB$)
                ON (FILREDO) GOTO FNMC, FILENM, FNMB
FNMC:           N = 0
            '
            '****( Clear data array )****
                FOR YYY = 1 TO 730: DATUM(YYY) = 0: TBUF$(YYY) = "":
                NEXT YYY
                DATUM(0) = 0!: REM TO AID CALC.OF FLUX IN THE OUTPUT
                FILE
            '
            '****( Set time interval -e.g. ON TIMER(TI) sets TI sec.
                interval )****
            '****( Set ABORT function )****
                ON TIMER(TI) GOSUB DATAQ
                ON KEY(10) GOSUB ABORT
                REM INIT TIME BUFFER FOR INDUCTION TIME
            '
            '****( Acquire initial wt. of SYN-URINE )****
SWLOOP:         CLS : LOCATE 12, 2
                INPUT "Sample Weight(gm)= ", SAMPLE
                IF SAMPLE = 0! THEN GOTO SWLOOP
                CORRWT = (27 / 39) * SAMPLE
                N = 0: INITWT = 0: GOSUB DATAQ: INITWT = ABSWT: GOSUB
                BELL
                DATUM(0) = 0!
                CLS
                MESS$(1) = "Place sample end into solution. "
                CALL WIN(0, 0, 1, MESS$(), -1)
                CLS
                MESS$(1) = "        UPHILL FIBER FLUX TEST           "
                MESS$(2) = " <F10> - To ABORT test."
                MESS$(3) = " <F1> + <ENTER> - To Exit Program.       "
                MESS$(4) = "                "
                MESS$(5) =
                "-----=====>>> NOW INITIATING TEST <<<=====-----"
                CALL WIN(2, 2, 5, MESS$(), 0)
                PRINT
                PRINT " TIME      TOTAL WT.     DELTA       INSTANT. "
                PRINT " (MIN.)    TRANSPORTED   WEIGHT      FLUX RATE"
                PRINT " ------------------------------------------"
                PRINT : GOSUB BELL
                INITTM$ = TIME$
      '****( Check for valid data )****
                N = 1: ABORT = 0
                KEY(10) ON
                IF (LOC(1) > 1) THEN INPUT #1, B$
      '****( Take Wind number of samples )****
                IF WIND = 15 AND TI = 60 THEN
                      LIMFLG = 0
                ELSE
                      LIMFLG = -2
                END IF
                TIMER ON
                FOR N = 1 TO 15
                            BALFLG = 0
                            WHILE NOT BALFLG
                            IF ABORT THEN GOTO FINEE
                            WEND
                GOSUB BELL
                PRINT USING "###       "; (N * TI / 60);
                PRINT USING "###.###      "; DATUM(N);
```

```
                PRINT USING "###.###       "; DATUM(N) - DATUM(N - 1);
                PRINT USING "###.###"; (DATUM(N) - DATUM(N - 1)) /
                      (TI*CORRWT/3600);
                NEXT N
                IF (LIMFLG = 0) THEN
                      CALL LIMITS(DATUM(), TI, TESTAVE, LIMFLG)
                END IF
                IF (LIMFLG = 0) THEN GOTO FINEE
                IF (LIMFLG = -1) THEN WIND = 45
                FOR N = 16 TO WIND
                            BALFLG = 0
                            WHILE NOT BALFLG
                            IF ABORT THEN GOTO FINEE
                            WEND
                GOSUB BELL
                PRINT USING "###          "; (N * TI / 60);
                PRINT USING "###.###        "; DATUM(N);
                PRINT USING "###.###        "; (DATUM(N) - DATUM(N - 1);
                PRINT USING "###.###"; (DATUM(N)-DATUM(N - 1))/ (TI *
                      (TI*CORRWT/3600)
                NEXT N

FINEE:          TIMER OFF
                KEY(10) OFF
      '
      '****( Take sample out of fluid )****
                GOSUB BELL
                MAXN = N - 1
                BALFLG = 0
                GOSUB TRANS
      '****( Store data on drive C: TEMPORARILY )****
                OPEN "C:TEMP.DAT" FOR OUTPUT AS #2
                GOSUB PRTDAT
      '****( Store data on diskette in drive A: )****
                OPEN AFILE$ FOR OUTPUT AS #2
                GOSUB PRTDAT
      '****( PROTECT FILE ON DISKETTE FROM OVERWRITE )****
                SHELL "ATTRIB +R " + AFILE$: REM MAKES FILE READ ONLY
      '****( Print hard copy to attached printer )****
                LPRINT "______ UPHILL FIBER FLUX
                TEST________________";
                LPRINT DATE$; "_________"; TIME$; "______"
                LPRINT : LPRINT "Data File:  "; AFILE$
                LPRINT "Description: "; DESC$
                LPRINT
                LPRINT " TIME      TOTAL WT.     DELTA     INSTANT. "
                LPRINT " (MIN.)    TRANSPORTED   WEIGHT    FLUX RATE"
                LPRINT " -----------------------------------------"
                FOR I = 1 TO MAXN
                LPRINT USING "###          "; (I * TI / 60);
                LPRINT USING "###.###        "; DATUM(I);
                LPRINT USING "###.###        "; DATUM(I) - DATUM(I - 1);
                LPRINT USING "###.###"; (DATUM(I)-DATUM(I - 1))/
                      (TI*CORRWT/3600
                NEXT I
                LPRINT
                      LPRINT USING "Total Sample Weight(gm): ###.###";
                            SAMPLE
                      LPRINT USING "Corr. Sample Weight(gm): ###.###";
                            CORRWT
                      LPRINT USING "Transport Rate(cc/gmhr)= ###.###";
                            TR
```

```
                    GOTO TABTB
TABTB:          LPRINT CHR$(12);
          REM COM$ = "PUTGRAPH " + AFILE$ + " E " + CHR$(13) +
          CHR$(10)
          REM SHELL COM$

     '
     '****( Prepare for next test )****
                FOR I = 1 TO 15
                GOSUB BELL
                FOR J = 1 TO 300
                NEXT J
                NEXT I
                FOR I = 1 TO 14: PRINT : NEXT I
     '''' INIT VARIABLES
                NBOOK$ = "": AFILE$ = ""
                B$ = "": DESC$ = ""
                TR = O!
                SAMPLE = O!: CORRWT = O!
                MESS$(1) = "           Remove Sample            "
                MESS$(2) = " ============================ "
                MESS$(3) = "                                    "
                MESS$(4) = " Press <ENTER> to test next sample. "
                MESS$(5) = "            - - 0 R - -             "
                MESS$(6) = " Press <Fl><ENTER> to exit program. "
                CALL WIN(11, 20, 6, MESS$(), -1)
                GOTO PREP
     '
DATAQ:          REM DATA ACQUISITION ROUTINE
                GOSUB baltopc
                TBUF$(N) = TIME$
                ABSWT = VAL(B$)
                DATUM(N) = 3.52 * (INITWT - ABSWT)
                BALFLG = -1
                RETURN
     '
baltopc:     '' BALANCE SERIAL COMMUNICATIONS ROUTINE
                WHILE (LOC(1) > 1)
                      INPUT #1, B$
                WEND
                B$ = ""
                PRINT #1, "SI"; CHR$(13); CHR$(10);
                WHILE (LEN(B$) = 0)
                      IF LOC(1) > 1 THEN INPUT #1, B$
                WEND
                IF LEN(B$) <> 14 THEN GOTO baltopc
                B$ = RIGHT$(B$, 10)
                RETURN
     '
BELL:           REM AUDIBLE ALERT ROUTINE (BELL)
                      TYPEBELL = 2
                      IF TYPEBELL = 3 THEN SOUND 400, 1: SOUND 500, 1:
                      SOUND 600, 1
                      IF TYPEBELL = 1 THEN SOUND 1000, 2
                      IF TYPEBELL = 2 THEN SOUND 400, 2
                      RETURN
     '
TITLE:          REM ROUTINE TO DISPLAY MAIN TEST TITLE
                      CLS
                      MESS$(1) = "          U P H I L L              "
                      MESS$(2) = "                                   "
                      MESS$(3) = "           F I B E R               "
```

— 78 —

```
                        MESS$(4) = "                                     "
                        MESS$(5) = "       F L U X   T E S T             "
                        CALL WIN(1, 20, 5, MESS$(), 0)
                        RETURN
      '
ABORT:            REM ROUTINE TO SET ABORT FLAG
                        ABORT = -1
                        RETURN
      '
ERTRAP:           REM ERROR TRAPPING ROUTINES
                  ERRBUF = ERR
                  WHILE (ERR = 57): REM "DEVICE I/O ERROR"
                        RESUME baltopc
                        WEND
                  WHILE (ERR = 71): REM "DISK NOT READY"
                        PRINT "Disk not READY in drive A:"
                        RESUME INSERT
                        WEND
                  WHILE (ERR = 61): REM "DISK FULL"
                        PRINT "DISKETTE FULL; INSERT NEW, FORMATTED
                        DISKETTE."
                        RESUME START
                        WEND
                  WHILE (ERR = 62)
                        PRINT "ERROR 62; Input Past File End."
                        INPUT "Press <ENTER> to continue...", DDD$
                        RESUME
                        WEND
                  WHILE (ERR = 5): REM "ILLEGAL FUNCTION CALL" (TIMCHK)
                        PRINT "TRY AGAIN - - -"
                        TIMFLG = -1
                        RESUME CLKSET
                        WEND
                  WHILE (ERR = 53): REM "FILE NOT FOUND"
                        CHDIR "A:\": OPEN "A:\UPHILL.CFG" FOR OUTPUT
                        AS 4
                        PRINT #4, " ": CLOSE #4
                        RESUME
                        WEND
                  WHILE (ERR = 67): REM "TOO MANY FILES"
                        CLOSE 2
                        PRINT "TOO MANY FILES ON DISKETTE; WILL SAVE ON
                        DRIVE C:"
                        INPUT "PRESS <ENTER> to continue...", DDD$
                        OPEN "C:\TEMP.DAT" FOR OUTPUT AS #2
                        GOSUB PRTDAT
                        PRINT "JUST SAVED FILE ON DRIVE C: AS
                        'TEMP.DAT'."
                        WEND
                  WHILE (ERR = 24 OR ERR = 25)
REM "DEVICE TIMEOUT" & "DEVICE FAULT"
                        FOR PHLP = 1 TO 10: SOUND 200, 5: SOUND 300, 5:
                        NEXT PHLP
                        PRINT : PRINT "Printer NOT Ready.....
                        CHECK IT !!"
                        PRINT "Press <ENTER> to Retry Printout"
                        INPUT ANS$
                        RESUME
                        WEND
                  WHILE (ERR = 75 OR ERR = 76)
                        RESUME NEXT
                  WEND
```

```
                WHILE (ERR = 58)
                      PRINT "FILE ALREADY EXISTS; TRY AGAIN"
                      RESUME FILENM
                WEND
                RESUME: REM GENERAL RESUME IF ERROR NOT COVERED IN
                THIS ROUTINE
                STOP
'
INSTRUCT:       REM ROUTINE TO DISPLAY GENERAL INSTRUCTIONS
                      MESS$(1) = "       GENERAL INSTRUCTIONS         "
                      MESS$(2) = "                                    "
                      MESS$(3) = " Press <F1> <ENTER> to exit this
                      program. "
                      MESS$(4) = " Press <F10> to abort the test.     "
                      CALL WIN(0, 0, 4, MESS$(), -1)
                      RETURN
'
TEXIT:          REM EXIT ROUTINE
                      PRINT #1, "RO"; CHR$(13); CHR$(10);
                      PRINT " Exitting UPHILL FLUX Program........":
                      CLOSE #1
                      CLOSE #2
                      CLOSE #3
                      SYSTEM
                      END
'
CLKSET:         REM ROUTINE TO SET SYSTEM CLOCK
                      TIMFLG = 0
                      INPUT "Enter correct time(Example: 9:35)- - -",
                      TTT$
                      TIME$ = TTT$
                      IF TIMFLG THEN GOTO CLKSET
                      RETURN
'
TRANS:          REM MAIN CALC ROUTINE FOR TRANSPORT TIME & RATE
                      PRINT USING "Total Sample Weight(gm): ###.###";
                      SAMPLE
                      PRINT USING "Corr. Sample Weight(gm): ###.###";
                      CORRWT
                      IF LIMFLG = -2 OR LIMFLG = -1 THEN GOSUB TCALCA
                      IF LIMFLG = 0 THEN GOSUB TCALCB
                      PRINT USING "Transport Rate(cc/gmhr)= ###.###";
                      TR
                      RETURN
'
TCALCA:         REM SPECIAL CALC ROUTINE FOR TRANSPORT RATE WHEN THE
                TEST TIME REM IS ANYTHING OTHER THAN THE 15 MINUTE,
                "QUICK TEST".
                      AVEPT1 = CINT(30 * 60 / TI)
                      SUM = 0
                      FOR I = AVEPT1 TO MAXN
                      SUM = SUM + (DATUM(I) - DATUM(I - 1))
                      NEXT I
                      AVE = SUM / (MAXN - AVEPT1 + 1)
                      TR = AVE / ((TI / 3600) * CORRWT)
                      RETURN
'
TCALCB:         REM SPECIAL CALC ROUTINE FOR TRANSPORT RATE DURING A
                15 MINUTE REM TEST.
                TR = TESTAVE / ((TI / 3600) * CORRWT)
                RETURN
'
```

```
WARN:           CLS
                bts = DSKFUL
                test45 = INT(bts / 2000)
                test15 = INT(test45 * 3)
                test90 = INT(test45 / 2)
                test720 = INT(test45 / 16)
                MESS$(1) = " Disk space for: "
                MESS$(2) = "      Number of 15 min. tests -> " +
                STR$(test15)
                MESS$(3) = "                45 min. tests -> " +
                STR$(test45)
                MESS$(4) = "                90 min. tests -> " +
                STR$(test90)
                MESS$(5) = "                12 hr. tests -> " +
                STR$(test720)
                MESS$(6) = " If needed, insert NEW DISKETTE into drive
                A: "
                CALL WIN(0, 0, 6!, MESS$(), -1)
                RETURN

PRTDAT:         'PRINT DATA TO FILES
                FOR I = 1 TO MAXN
                      PRINT #2, USING "###        "; (I * TI / 60);
                      PRINT #2, USING "###.###    "; DATUM(I);
                      PRINT #2, USING "###.###    "; DATUM(I) -
                      DATUM(I - 1);
                      PRINT #2, USING
                      "###.###";(DATUM(I)-DATUM(I-1))/(TI*CORRWT/3600)
                NEXT I
                      PRINT #2, "Data File: ,"; AFILE$
                      PRINT #2, "Desc: ,"; DESC$
                      PRINT #2, "Date: ,"; DATE$
                      PRINT #2, USING "Total Sample Weight(gm):,
                      ###.###"; SAMPLE
                      PRINT #2, USING "Corr. Sample Weight(gm):,
                      ###.###; CORRWT
                      PRINT #2, USING "Transport Rate(cc/gmhr)=,
                      ###,###"; TR
                      FOR I = 1 TO 10: PRINT #2, CHR$(26); : NEXT I
                      CLOSE #2

                      RETURN

FUNCTION DSKFUL
          SHELL "dir a: > c:\dir.doc"
          OPEN "c:\dir.doc" FOR INPUT AS #5
          WHILE NOT EOF(5)
                INPUT #5, lin$
          WEND
          CLOSE #5
          SHELL "del c:\dir.doc"
          DSKFUL = VAL(RIGHT$(lin$, 20))

END FUNCTION

SUB LIMITS (DAT(), TM, AVE, LIMFLG)
          LIMFLG = 0: AVE = 0
          FOR I = 1 TO 25
                IF ((I * TM / 60) >= 10) THEN
                      N010 = I
                      GOTO NL1
                END IF
```

```
            NEXT I
      NL1: FOR I = 1 TO 25
                  IF ((I * TM / 60) >= 15) THEN
                        NO15 = I
                        GOTO NL2
                        END IF
            NEXT I
      NL2: DIFF10 = DAT(NO10) - DAT(NO10 - 1)
            DIFF15 = DAT(NO15) - DAT(NO15 - 1)

            LIMVAL = ABS(((DIFF15 - DIFF10) / DIFF10) * 100)
            FOR I = NO10 TO NO15
                  AVE = AVE + DAT(I) - DAT(I - 1)
            NEXT I
            AVE = AVE / (NO15 - NO10 + 1)
            IF (LIMVAL >= 15 AND AVE > .4) THEN LIMFLG = -1
            IF (LIMVAL >= 33 AND AVE <= .4) THEN LIMFLG = -1
      '************************************************************'
      '*The limit values 15 and 33 were arrived at empirically by
      '*observing data for 9/4/90 - 9/6/90 to determine limits that
      '*would provide a 15 minute tests for a majority of the
      '*samples tested.  In the observed tests.  The 62% of the
      '*samples would have been tested for 15 minutes automatically.
      '************************************************************'

END SUB

SUB WIN (r!, c!, max!, array$(), FLG!)
' window routine for uphill.bas
            wid = 0
            FOR I = 1 TO max
                  IF (LEN(array$(I)) > wid) THEN wid = LEN(array$(I))
            NEXT I
            hgt = max + 4
            wid = wid + 4

            IF c = 0 THEN c = INT((79 - wid) / 2)
            IF r = 0 THEN r = INT((24 - hgt) / 2)

            LOCATE r, c: FOR I = 1 TO wid: PRINT CHR$(219); : NEXT I
            FOR I = r + 1 TO r + hgt
            LOCATE I, c: PRINT CHR$(219); : LOCATE I, c + wid - 1: PRINT
            CHR$(219);
            PRINT CHR$(176); : PRINT CHR$(176);
            NEXT I
            LOCATE r + hgt, c: FOR I = 1 TO wid: PRINT CHR$(219); :
            NEXT I
            PRINT CHR$(176);
            LOCATE r + hgt + 1, c + 2: FOR I = 1 TO wid: PRINT
            CHR$(176);
            NEXT I
            FOR I = I TO max: LOCATE r + I + 1, c + 2: PRINT array$(I);
            : NEXT I
            LOCATE r + hgt + 3, c + 2
            IF FLG THEN
                  INPUT "Press <Enter> to continue....", AAA$
            END IF
END SUB
```

TABLE II

Figure 35:
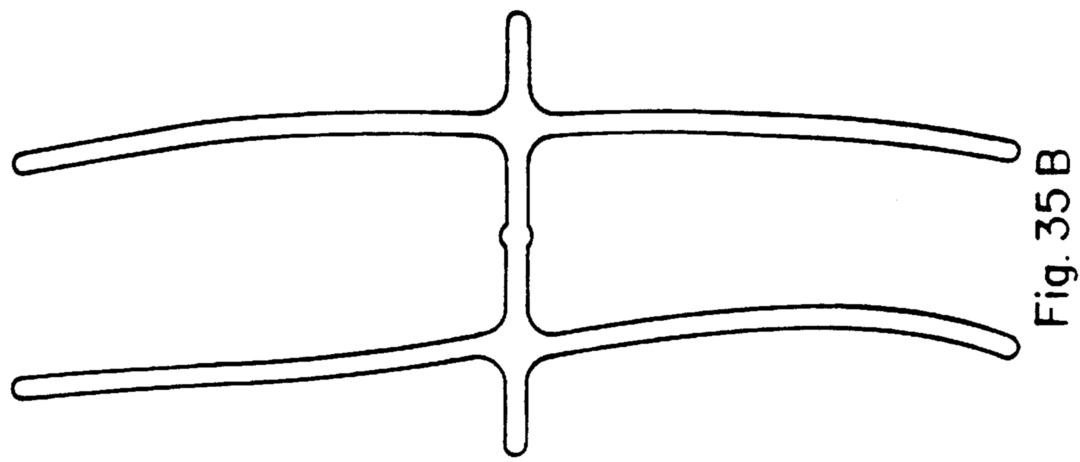
Figure 35:
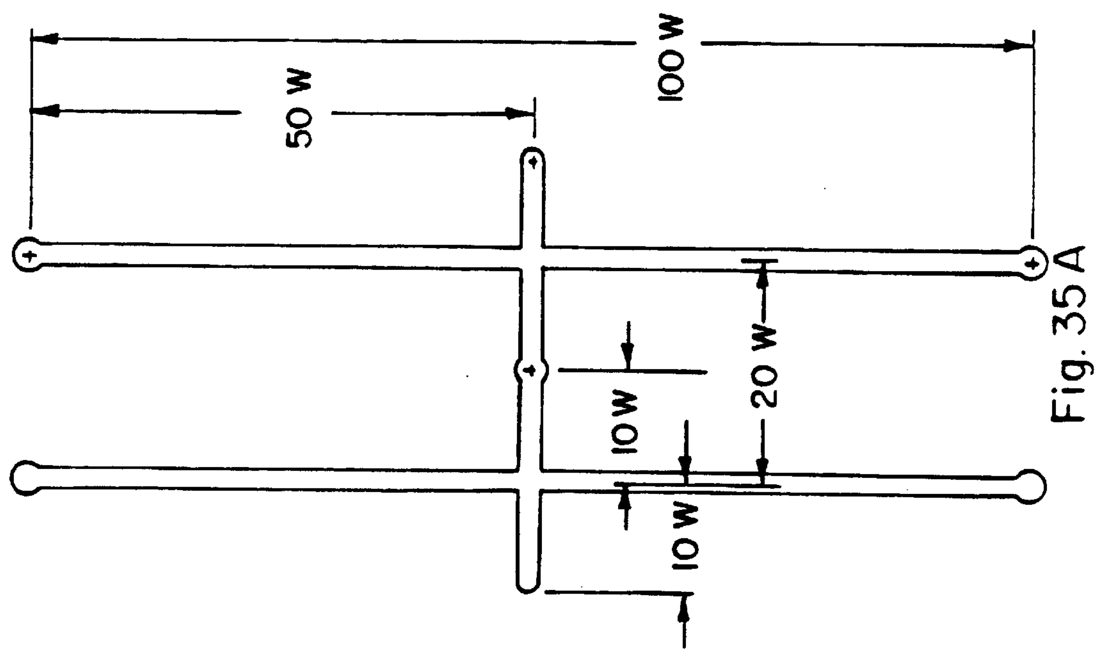
Figure 36:
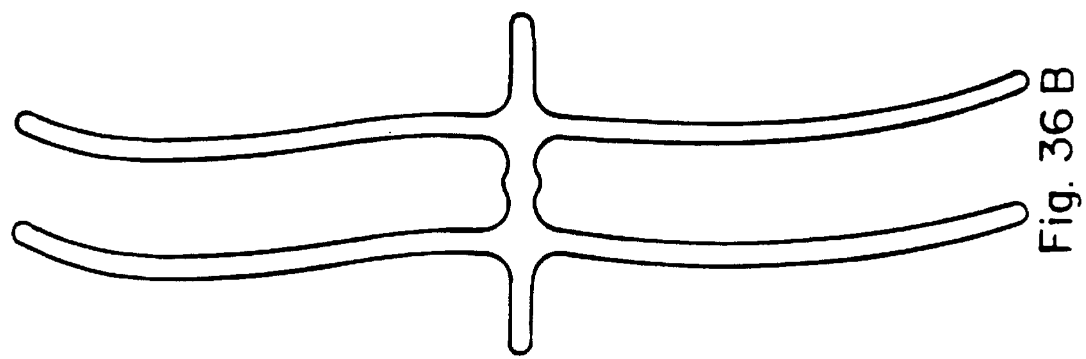
FIGS. 36A and 36B—are schematic representation of a preferred "H" shape orifice of a spinneret useful for producing a spontaneously transportable fiber (see Example 23). "W" as shown herein is the same as "$W_1$" referred to in Example 23.
Figure 36:
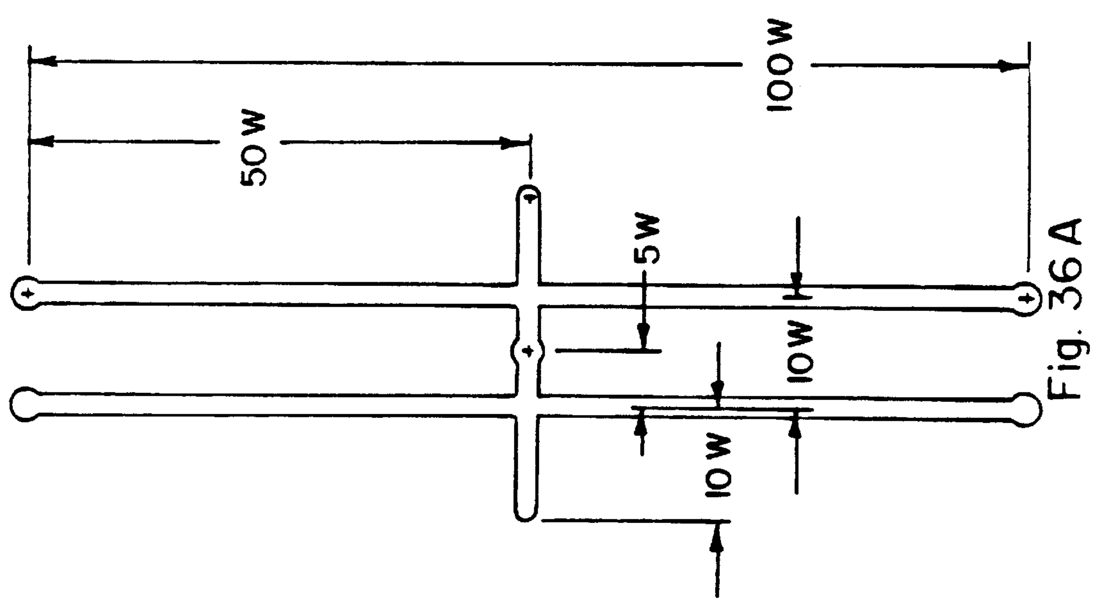

| | | | Fiber Properties Single Filament Wetting Parameters | | | | | | | | | | |
|---|---|---|---|---|---|---|---|---|---|---|---|---|---|
| Sample[1] | Spinneret | Take-up Speed m/m | Finish Applied in Spinning, % | Denier/Filament | Specific[2] Volume cc/gm | Channel Width (microns) | Leg Thickness (microns) | Channel Depth (microns) | Backbone Thickness (microns) | Initial Velocity mm/sec | Slope mm²/sec | Flux cc/gm/hr | Adhesion Tension dyne/cm |
| 001-6A | FIG. 35 | 300 | None | 73 | 3.56 | 53.1 | 8.9 | 123 | 10.5 | 51 | 203 | 37.5[P] | 60 |
| | FIG. 35 | 300 | 70% PEG 600 Monolaurate 30% Potassium Lauryl Phosphate 0.5% | 73 | 3.56 | 53.1 | 8.9 | 123 | 10.5 | | | 0.8 | 32 |
| 001-7B | FIG. 36 | 200 | None | 103 | 3.03 | 35.5 | 11.4 | 166 | 15.0 | | | 22.7[P] | 60 |
| | FIG. 36 | 200 | 70% PEG 600 Monolaurate 30% Potassium Lauryl Phosphate 0.5% | 103 | 3.03 | 35.5 | 11.4 | 166 | 15.0 | | | 3.1 | 32 |
| 001-4B | FIG. 36 | 200 | 70% PEG 600 Monolaurate 30% Potassium Lauryl Phosphate 0.5% | 110 CD | 2.42 | 39.0 | 11.5 | 171 | 14.8 | | | 6.3[P] | 35 |
| 003-1-1 | Same as 001-6A except drawn 2× and heatset at 130° C. | | None | | | 40.0 | 7.0 | 91.4 | 7.9 | | | 32.4[P] | 60 |
| 003-2-1 | Same as 001-78 except drawn 2× and heatset at 130° C. | | None | | | 23.1 | 7.7 | 104 | 10.1 | | | 20.1[P] | 60 |

[1]Polymer, 0.89 I.V., bright PET melt temperature 295° C. quench air-235 ft/min ar 21" below spinneret.
[2]Described in U.S. Pat. No. 4,245,001.
[P]= Plasma treated. The equipment used was the same as described in Example 1 hereof except a Leesona winder was used for take-up.

Example 24

Figure 37:
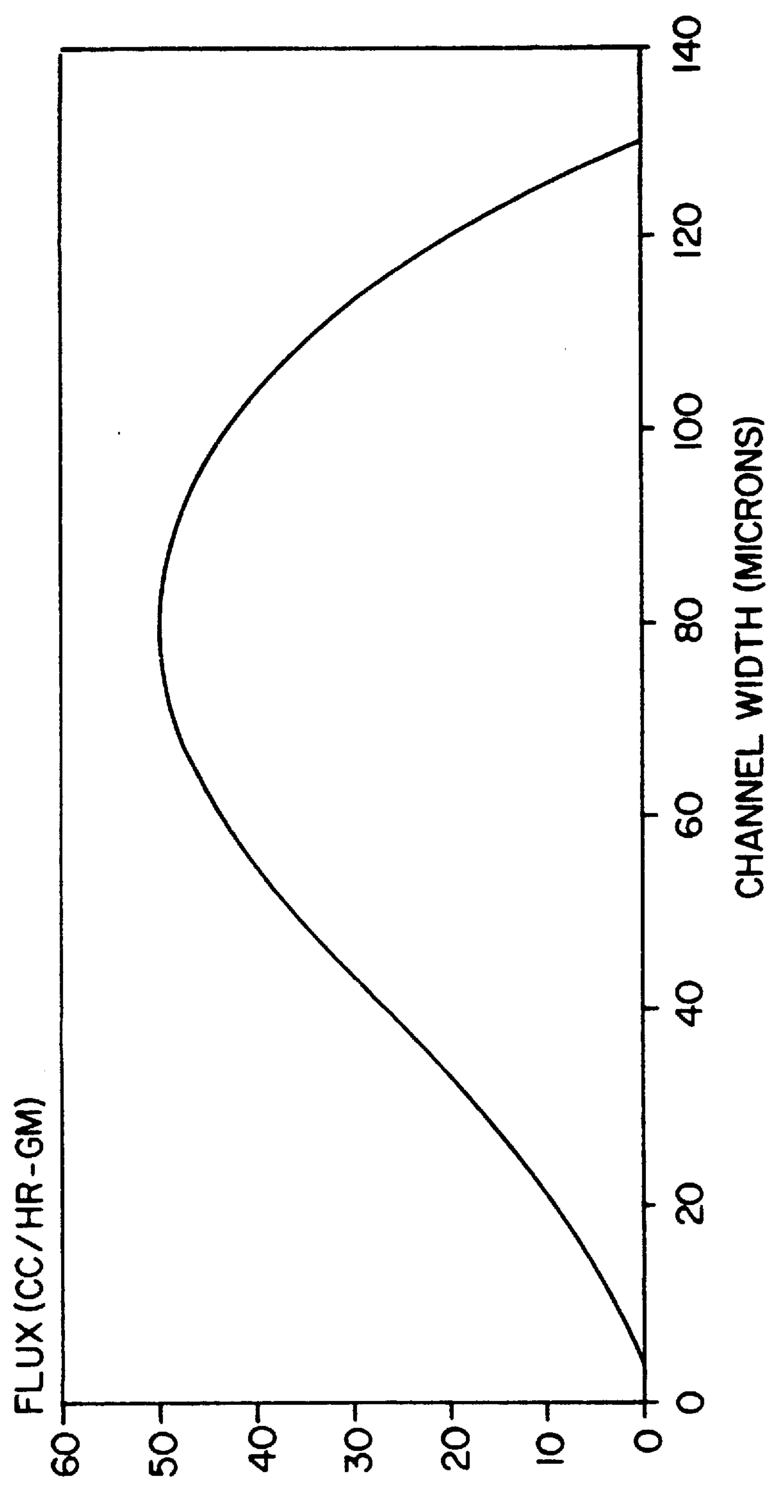
FIG. 37—graph of the flux in cc/hr/g vs. channel width (microns) for a plasma treated spontaneously transportable fiber made of poly(ethylene terephthalate) and having an "H" shape cross-section.

This example shows the influence of channel width on uphill flux for fixed values of channel depth, leg width, material of choice and adhesion tension. Notice the maximum flux occurs at a channel width of approximately 80 microns for the dimensions of the PET fiber shown (see FIG. 37).

Example 25

Figure 38:
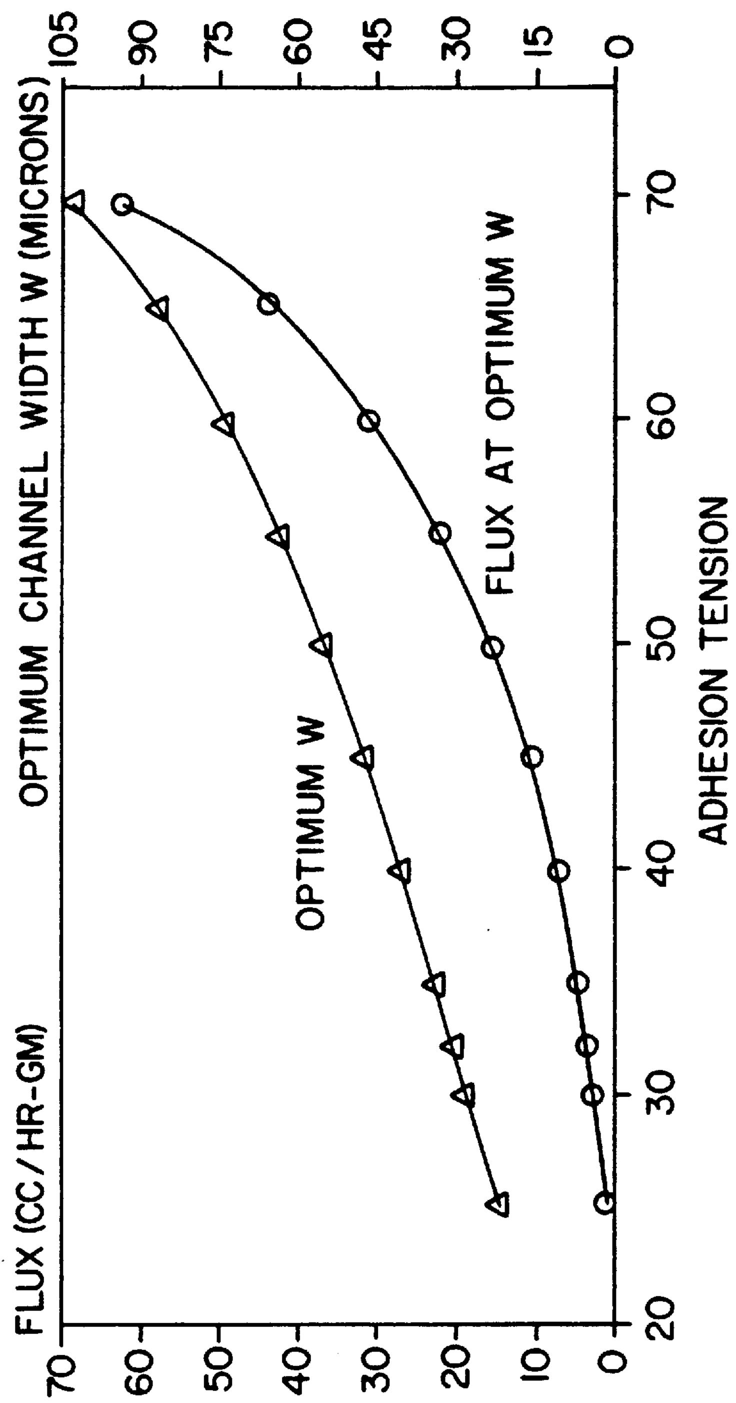
FIG. 38—graph of maximum flux in cc/hr/g vs. adhesion tension for a poly(ethylene terephthalate) having an "H" shape cross-section with two unit cells or channels wherein each channel depth is 143 $\mu$ and the leg thickness of each channel is 10.9$\mu$.

The influence of increasing the adhesion tension is shown dramatically in Example 23. This example shows how the uphill flux varies for a given fiber material and geometry with adhesion tension (see FIG. 38). In other words, for each adhesion tension at a fixed leg width and channel depth, there is an optimum channel width which maximizes the flux.

Example 26

Figure 41:
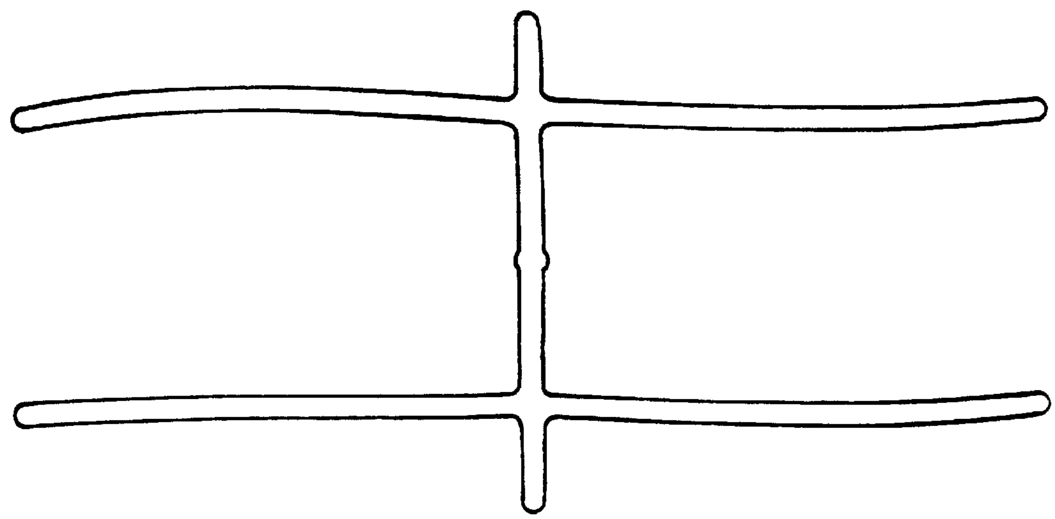
FIGS. 41A and 41B—are schematic representations of a spinneret having dimensions as specified.
Figure 41:
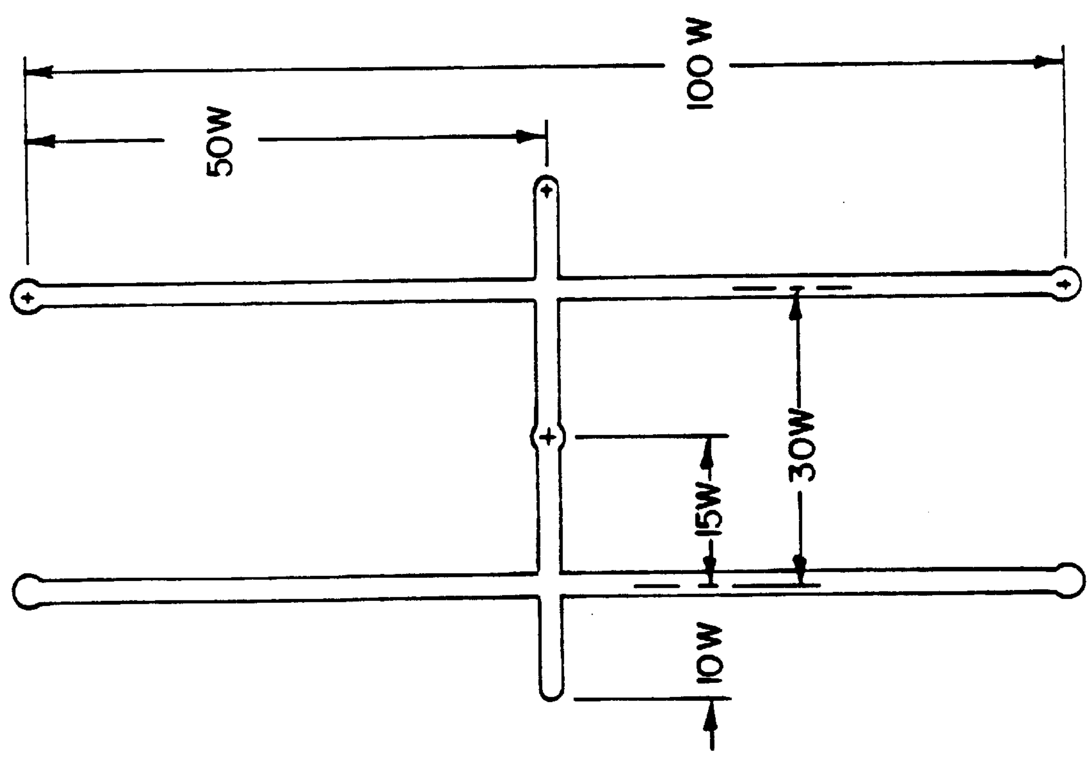

Hydrofil® nylon polymer designated SCFX by Allied-Signal, Inc. was spun into fiber using the spinneret shown in FIG. 41 at 270° C. using water as the finish applied. The "W" shown in FIG. 41A was 100 microns. The cross-section of the fiber is also shown in FIG. 41. These fibers yielded a flux of 10.4 cc/gm/hr in the uphill test. The measured adhesion tension was about 50 dynes/cm. Thus, this particular nylon coupled with spinning conditions which yielded a good cross-section with a channel width of 44 microns produced a very high flux without any surface finish or treatment.

Example 27

PET fiber similar to that in Example 23 was spun at 70 dpf. Approximately 3 grams of this sample were placed in a metal frame (approximately 15 inches long and 8 inches wide) and shipped to Plasma Science, Inc. for treatment. First, the PET sample was treated with Argon plasma for about 2 minutes. The pressure in the chamber of the Plasma Science PS-0500 plasma surface treatment system was reduced to about 0.3 torr. Power input to the unit was maintained at about 300 watts. Excitation power was provided by the RF generator operating at 13.56 MHz. Subsequently, the RF generator was turned off, acrylic acid vapors were introduced in the chamber for about 10 minutes, and the pressure was reduced to 0.02 torr. The acrylic acid vapors reacted with the plasma treated PET fiber surface resulted in an acrylic acid grafted PET surface. These fibers gave a 7.4 cc/gm/hr flux in the uphill test.

EXAMPLE 28

A 0.90 I.V. PET polymer was extruded on the system described in Example 1 at 289° C. The cross flow air velocity was 115 feet/minute and the takeup velocity was 800 feet/minute. Lubricant (5% active solution of Milease T in water) was applied from a double kiss roll arrangement in spinning at 10 rpm. The diameter of the ceramic oil roll was 150 mm. A 10 hole radial design spinneret was used to spin the fiber. The spinneret was identical to that shown in FIG. 43 except that the width of the "H" slot was 25 W instead of 50 W and W=0.100 mm. The extrusion rate was adjusted to make a nominal 75 dpf fiber. The resulting channel dimensions were 55 microns channel width, 7.3 microns leg width, and 172 microns channel depth. This fiber produced a flux of 7.6 cc/g/hr. in the uphill flux test.

Example 29

This example shows a stuffer box crimped fiber with a distorted cross section and a helical crimped fiber without a distorted cross section. The stuffer box crimped sample was listed as sample SW-181-1A, and the helical crimped sample was listed as sample SW-186. Both samples were of a two channel H cross section.

Figures 42A, 42B, 42C:
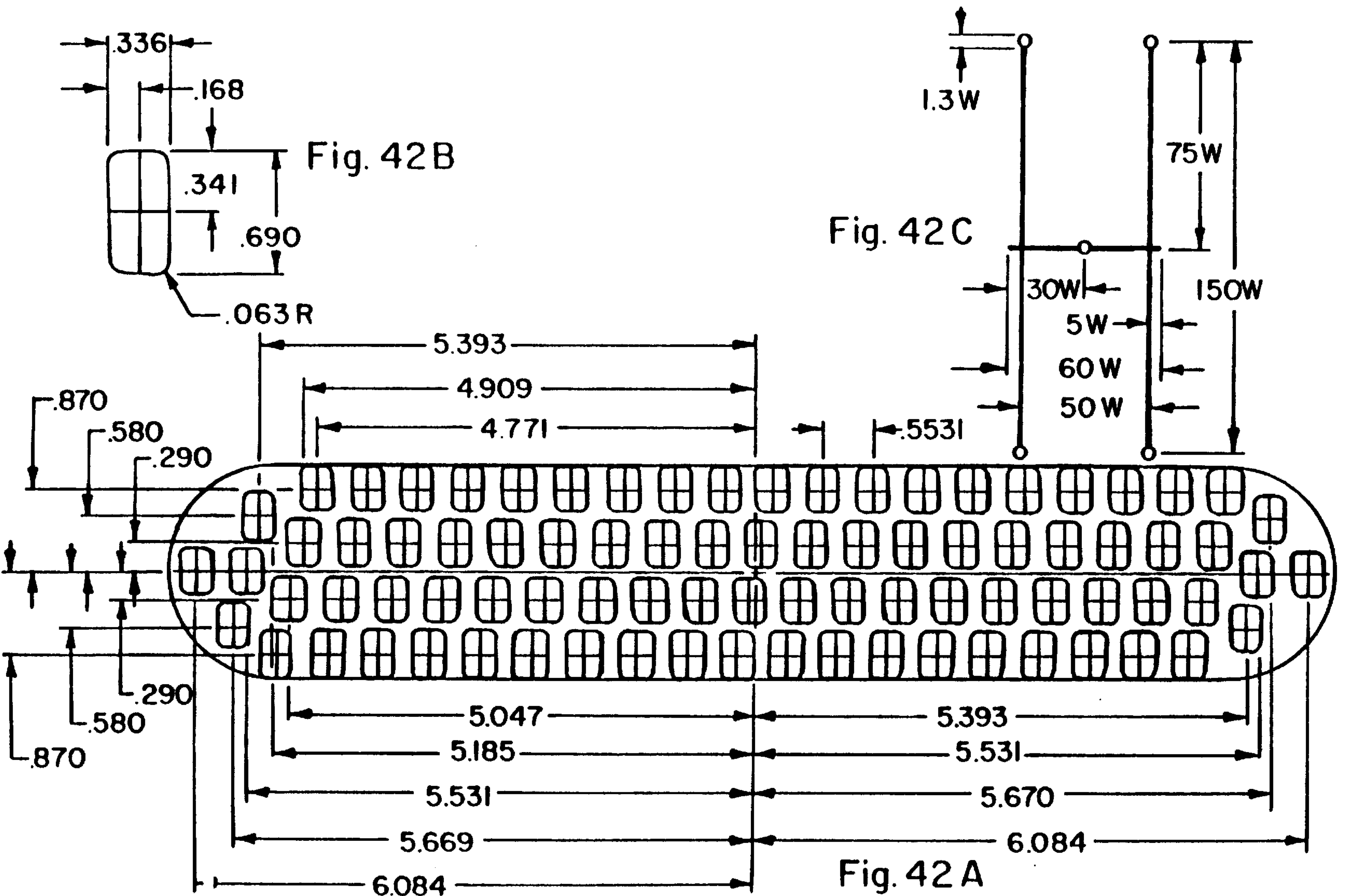
FIGS. 42A, 42B and 42C—schematic representations of Spinneret I1045 wherein the spinneret holes are oriented such that the cross-flow quench air is directed toward the open end of the H. All dimensions are in units of inches except those containing the letter "W".

Sample SW-181-1A for stuffer box crimping was melt spun from 0.68 IV poly(ethylene terephthalate) polymer on a unit using a spinneret I 1045 to make a 38 denier per filament continuous filament fiber. Spinneret I 1045 is described in FIG. 42. The "W" in FIG. 42C was 84 microns. The spinneret holes were oriented such that the cross-flow quench air was directed toward the open end of the H at a velocity of 180 foot per minute as the fibers traveled down the cabinet. The fiber was spun at 1000 meters per minute with a melt temperature of 285° C. and lubricated with Hypermer A109 lubricant (a modified polyester surfactant sold by ICI Americas, Inc.).

Sample SW-186 for helical crimping was melt spun from 0.62 IV poly(ethylene terephthalate) polymer on a unit using spinneret I 1039 to make a 30 denier per filament continuous filament fiber. Spinneret I 1039 is described in FIG. 43. The "W" in FIG. 43A was 100 microns. The spinneret holes were oriented in a radial pattern on the face of the spinneret. Cross-flow quench air was directed at a velocity of 125 foot per minute toward the fiber bundle as the fibers traveled down the cabinet. The fiber was spun at 1500 meters per minute with a melt temperature of 288° C. and lubricated with PM 13430 lubricant comprising 49% polyethylene glycol (PEG) 600 monolaurate, polyoxyethylene (13.64) monolaurate, 49% polyethylene glycol (PEG) 400 monolaurate, polyoxyethylene (9.09) monolaurate, and 2% 4-cetyl-4-ethylmorpholinium ethosulfate (antistat). The equipment used was the same as described in Example 1 except that a Leesona winder was used for take-up.

A conventional two stage drafting line was used to process the SW-181-1A and SW-186 as-spun fiber.

Figure 44:
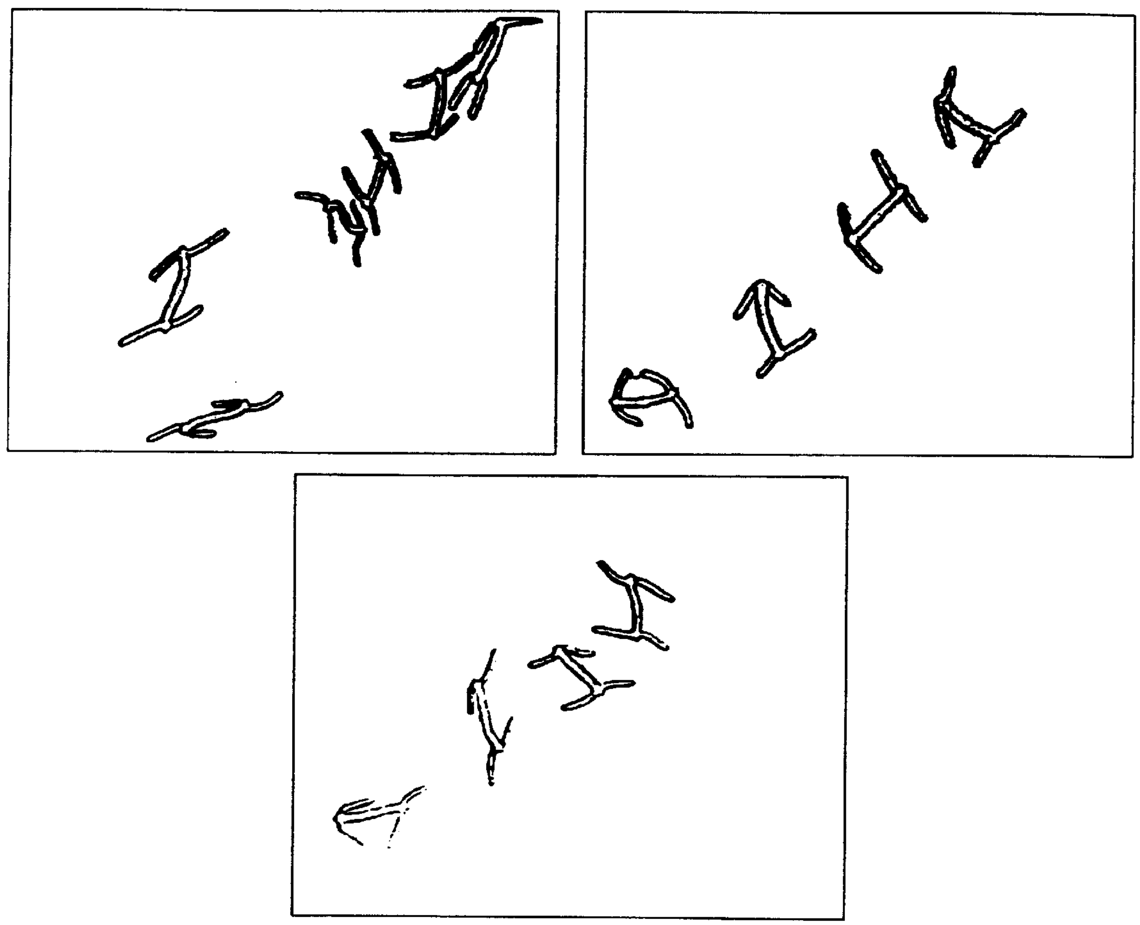
FIG. 44—a photomicrograph of stuffer box crimped fiber having a distorted cross-section.

The packages of SW-181-1A feed yarn were placed on creel posts and formed into a tow. The tow was guided to the first set of rolls running at 18 meters per minute. The tow left the first rolls and was submerged in a water bath having a water temperature of 74° C. The tow was guided from the water bath to the second set of rolls which were running at 35 meters per minute. The tow continued from the second rolls through a steam chamber set at 130° C. to the third rolls running at 45 meters per minute. The tow then went over a series of heatset rolls set at 180° C. to heatset the fiber with tension. The tow then went through a stuffer box crimper and was placed onto a dryer apron which carried the tow into an oven for drying the fiber at 100° C. for 5 minutes. In this case, Hypermer A109 lubricant was applied to the tow at the crimper. The stuffer box crimped fiber had a distorted cross section as shown in FIG. 44.

Figure 45:
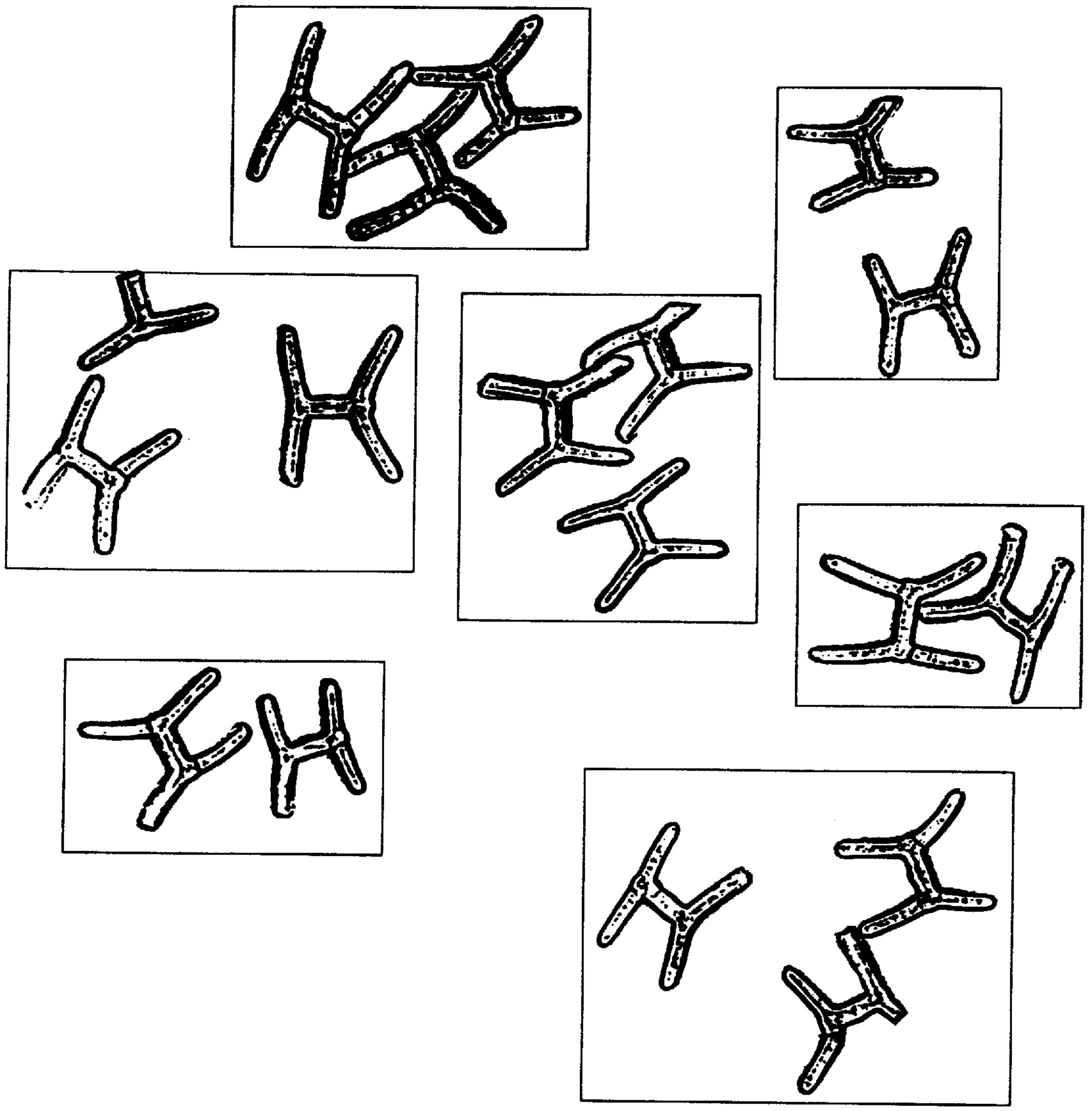
FIG. 45—a photomicrograph of a cross-section of a helically crimped fiber formed by the process of helically crimping a fiber of this invention wherein the fiber cross-section is not distorted.

The packages of feed yarn were placed on creel posts and formed into a tow. The tow was guided to the first set of rolls running at 26 meters per minute. The tow left the first rolls and was submerged in a water bath having a water temperature of 70° C. The tow was guided from the water bath to the second set of rolls which were running at 39 meters per minute. The tow continued from the second rolls through a steam chamber set at 130° C. to the third rolls running at 60 meters per minute. The tow then went to a puddling jet which placed the tow onto a dryer apron which carried the tow into an oven for shrinking without tension at 150° C. for 5 minutes. In this case, PM 13430 lubricant was applied to the tow as it exited the dryer. Helical crimped fiber formed during the shrinking step in the oven. The helical crimped fiber did not have a distorted cross section as shown in FIG. 45.

Example 30

This example shows the importance of having the spinneret hole shapes oriented in specified configurations relative to the cross-flow quench air when making helical crimped fibers.

Figures 46A, 46B, 46C:
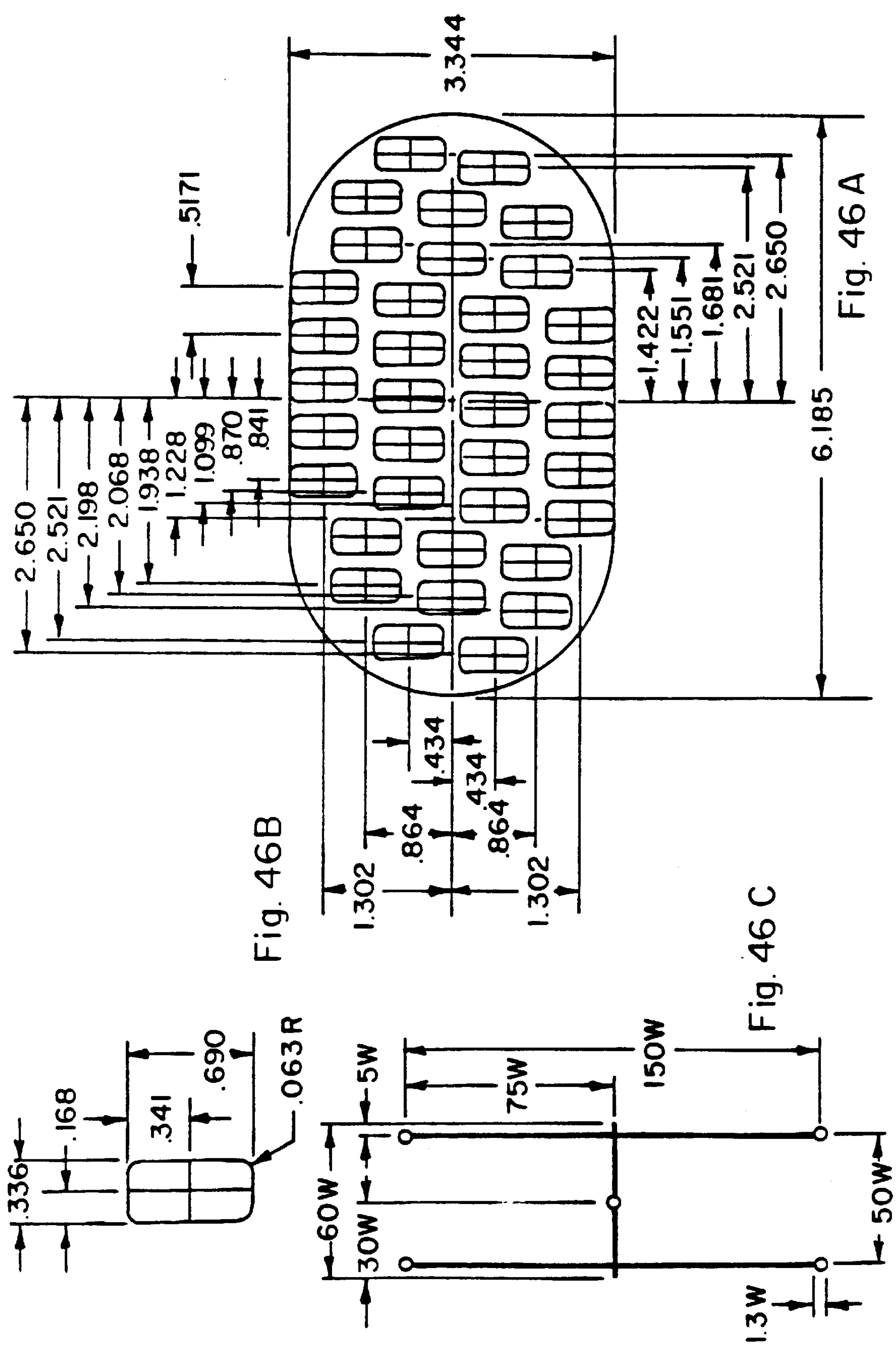
FIGS. 46A, 46B and 46C—schematic representations of Spinneret I 1046 wherein the spinneret holes are oriented such that the cross-flow quench air is directed toward the open end of the H.
Figure 47:
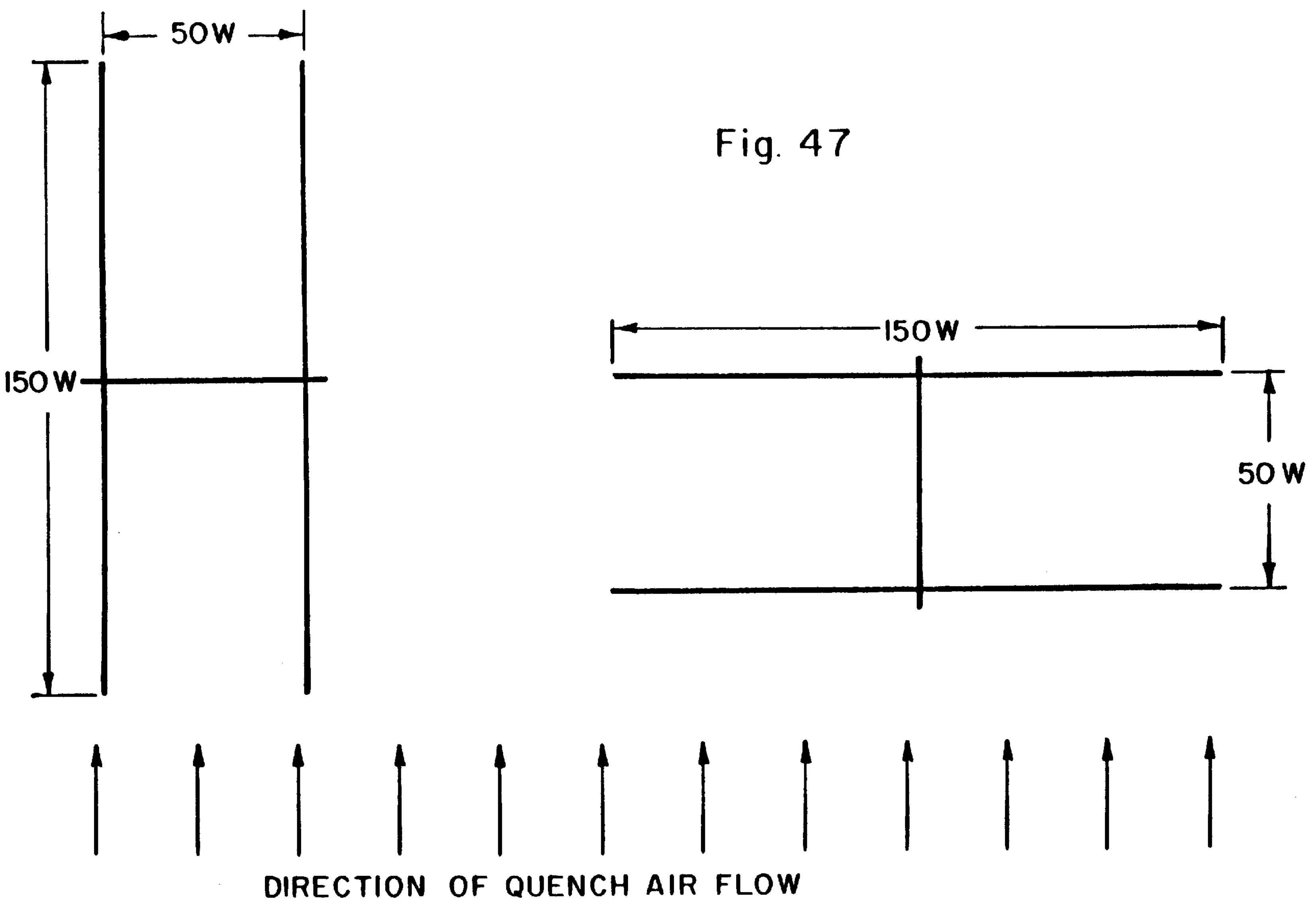
FIG. 47—a schematic representation of quench air direction relative to the spinneret holes.

Sample X21766-177-1 was melt spun from 0.70 IV poly(ethylene terephthalate) polymer using spinneret I 1046 on a unit to make a 51 denier per filament continuous filament fiber. Spinneret I 1046 is described in FIG. 46. The "W" in FIG. 46C was 84 microns. The spinneret holes were oriented such that the cross-flow quench air was directed toward the open end of the H at a velocity of 111 feet per minute as the fibers traveled down the cabinet. A drawing of the quench air direction relative to the spinneret hole is shown in FIG. 47. The fiber was spun at 1000 meters per minute with a melt temperature of 285° C. and lubricated with PM 13430 lubricant. The equipment used was the same as described in Example 1 except that a Leesona winder was used for take-up.

As-spun sample X21766-177-1 was drafted by guiding the yarn to a first set of rolls running at 25 meters per minute. The fiber left the first rolls and was submerged in a water bath having a water temperature of 70° C. The fiber was guided from the water bath to the second set of rolls which were running at 47.5 meters per minute. The fiber continued from the second rolls through a steam chamber set at 145° C. to the third rolls running at 52.5 meters per minute. The fiber was then wound onto a package and identified as sample number X21766-183-1A. A denier reel was used to unwind fiber from the package to make a skein of yarn. The skein was placed in a forced air oven set at 150° C. for 5 minutes and allowed to shrink without tension. Acceptable helical crimp did not form during the shrinking step in the oven. The fiber contained crenulated sections with a distorted cross-section.

Figures 48, 48B:
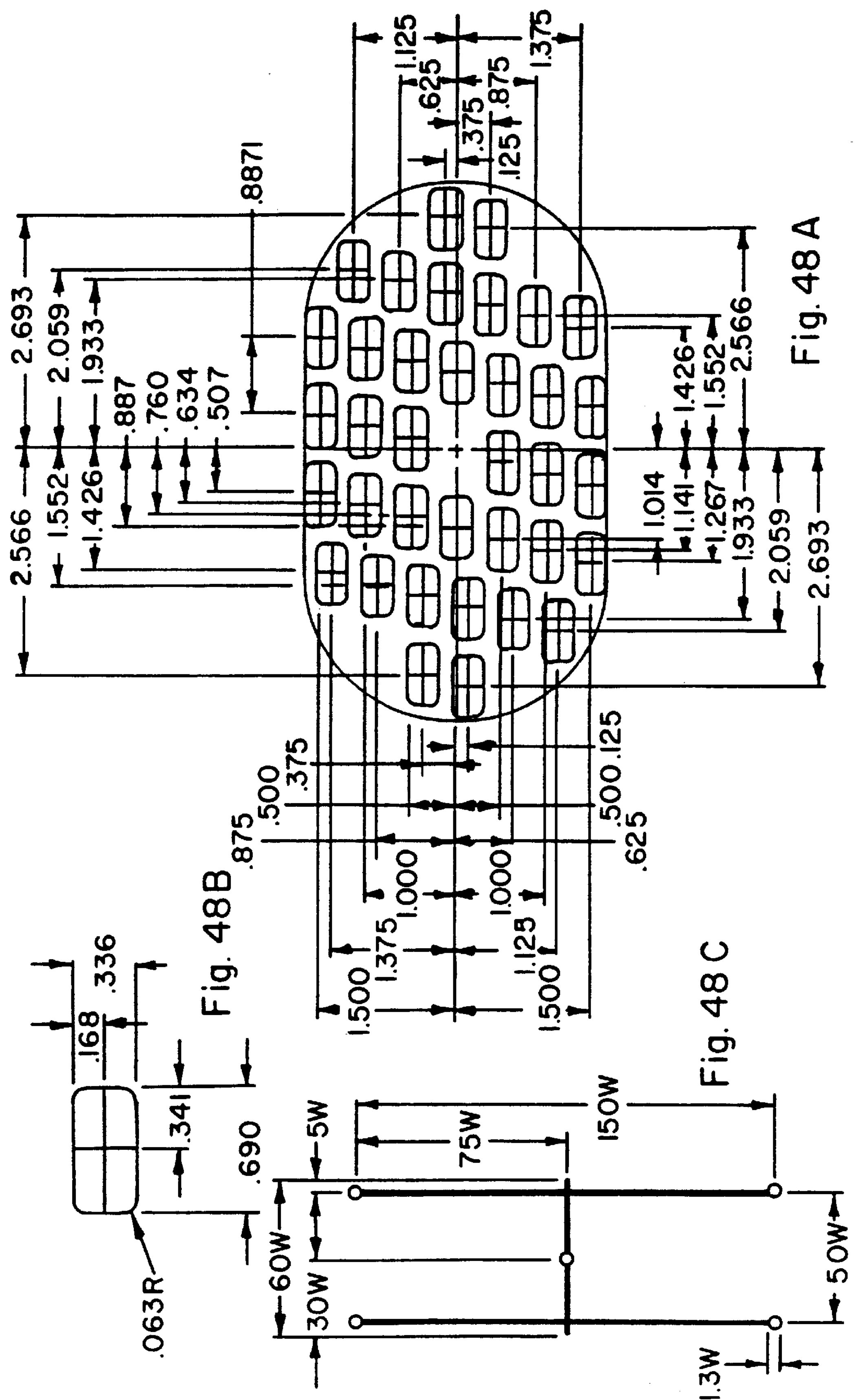

Sample X21766-176-1 was melt spun from 0.70 IV poly(ethylene terephthalate) polymer using spinneret I 1047 on a unit to make a 51 denier per filament continuous filament fiber. Spinneret I 1047 is described in FIG. 48. The "W" in FIG. 48C was 84 microns. The spinneret holes were oriented such that the cross-flow quench air was directed toward one side of the H at a velocity of 111 feet per minute as the fibers traveled down the cabinet. A drawing of the quench air direction relative to the spinneret hole is shown in FIG. 47. The fiber was spun at 1000 meters per minute with a melt temperature of 285° C. and lubricated with PM 13430 lubricant. The equipment used was the same as described in Example 1 except that a Leesona winder was used for take-up.

As-spun sample X21766-176-1 was drafted by guiding the fiber to a first set of rolls running at 25 meters per minute. The yarn left the first rolls and was submerged in a water bath having a water temperature of 70° C. The fiber was guided from the water bath to the second set of rolls which were running at 52.5 meters per minute. The fiber continued from the second rolls through a steam chamber set at 145° C. to the third rolls running at 57.5 meters per minute. The fiber was then wound onto a package and identified as sample X21766-181-1A. A denier reel was used to unwind fiber from the package to make a skein of yarn. The skein was placed in a forced air oven set at 150° C. for 5 minutes and allowed to shrink without tension. Helical crimped fiber formed during the shrinking step in the oven. The helical crimped sample had 7.4 crimps per inch with a crimp amplitude of 0.46 mm. The sample had an a bulky look and an acceptable hand.

Example 31

This example shows that helical crimped fiber without a distorted cross section will improve fluid movement when compared to a stuffer box crimped sample with a distorted cross-section.

Spontaneously wettable polyester fibers identified as SW-188 were melt spun from 0.78 IV poly(ethylene terephthalate) polymer using spinneret I-1039 on a unit to make a 29 denier per filament continuous filament fiber. Spinneret I 1039 is described in FIG. 43. The spinneret holes were oriented in a radial pattern on the face of the spinneret with cross-flow quench air directed at a velocity of 100 foot per minute toward the fiber bundle as the fibers traveled down the cabinet. The fiber was spun at 1500 meters per minute with a melt temperature of 292° C. and lubricated with PM 13430 lubricant. The equipment used was the same as described in Example 1 except that a Leesona winder was used for take-up.

A conventional two stage drafting line was used to process the as-spun fiber.

Figure 49:
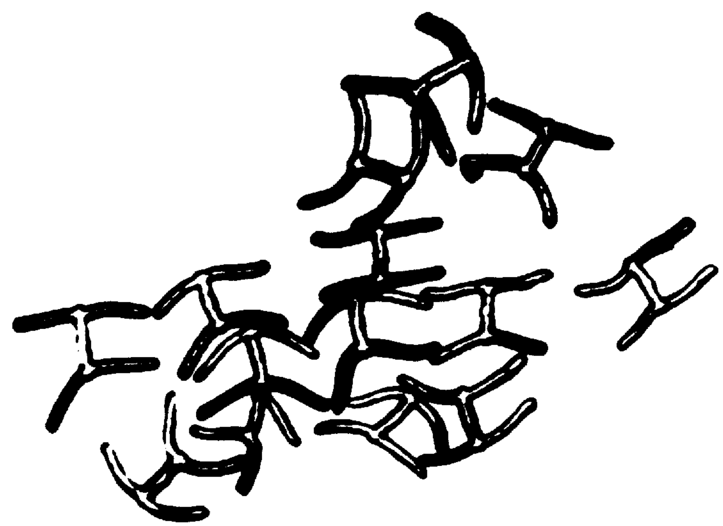
FIG. 49—a photomicrograph of helically crimped fibers of the invention without a distorted cross-section.

Helical crimped fiber without a distorted cross-section was first made. The as-spun packages were placed on creel posts and formed into a tow. The tow was guided to a first set of rolls running at 20 meters per minute. The tow left the first rolls and was submerged in a water bath having a water temperature of 73° C. The tow was guided from the water bath to the second set of rolls which were running at 35 meters per minute. The tow continued from the second rolls through a steam chamber set at 135° C. to the third rolls running at 43 meters per minute. The tow then went to a puddling jet which placed the tow onto a dryer apron which carried the tow into an oven for shrinking without tension at 150° C. for 5 minutes. PM 13430 lubricant was applied to the tow as it exited the dryer. Helical crimped fiber formed during the shrinking step in the oven. The helical crimped fiber did not have a distorted cross section as shown in FIG. 49.

Figure 50:
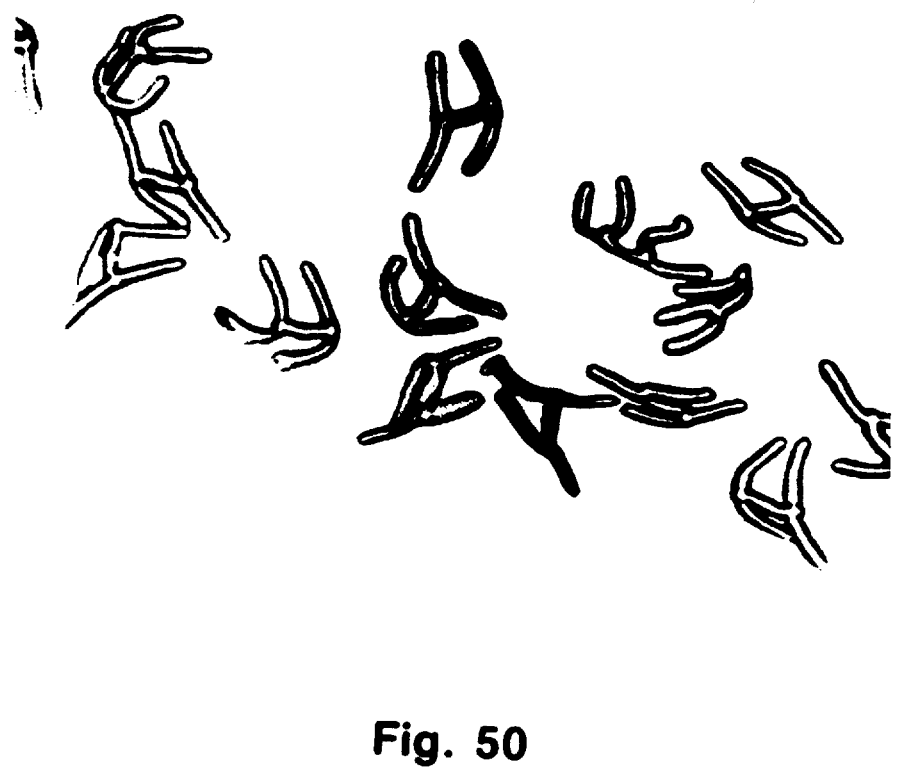

Stuffer box crimped fiber with a distorted cross-section was then made from the as-spun packages. The as-spun packages were placed on creel posts and formed into a tow. The tow was guided to a first set of rolls running at 20 meters per minute. The tow left the first rolls and was submerged in a water bath having a water temperature of 73° C. The tow was guided from the water bath to the second set of rolls which were running at 35 meters per minute. The tow continued from the second rolls through a steam chamber set at 135° C. to the third rolls running at 43 meters per minute. The tow then went through a stuffer box crimper and was then heatset without tension at 150° C. for 5 minutes. In this case, LK 5570 lubricant was applied to the tow just before the crimper. The stuffer box crimped fiber did have a distorted cross section as shown in FIG. 50.

The single filament wettability test is a useful test for characterizing these materials. Filaments from each type of crimp were tested sixty times for single filament wetting, and the results are shown below.

| | Stuffer Box Crimped | Helical Crimped Crimped |
|---|---|---|
| Average Velocity (mm/sec) | 14.7 | 19.7 |
| Average Slope (mm*mm/sec) | 9.7 | 32.3 |

This data is significant at the 95% confidence level and shows that the helical crimped sample is better for moving fluids than the stuffer box crimped sample.

Example 32

This example shows a helical crimped fiber made using an I-1005 spinneret.

Figure 51:
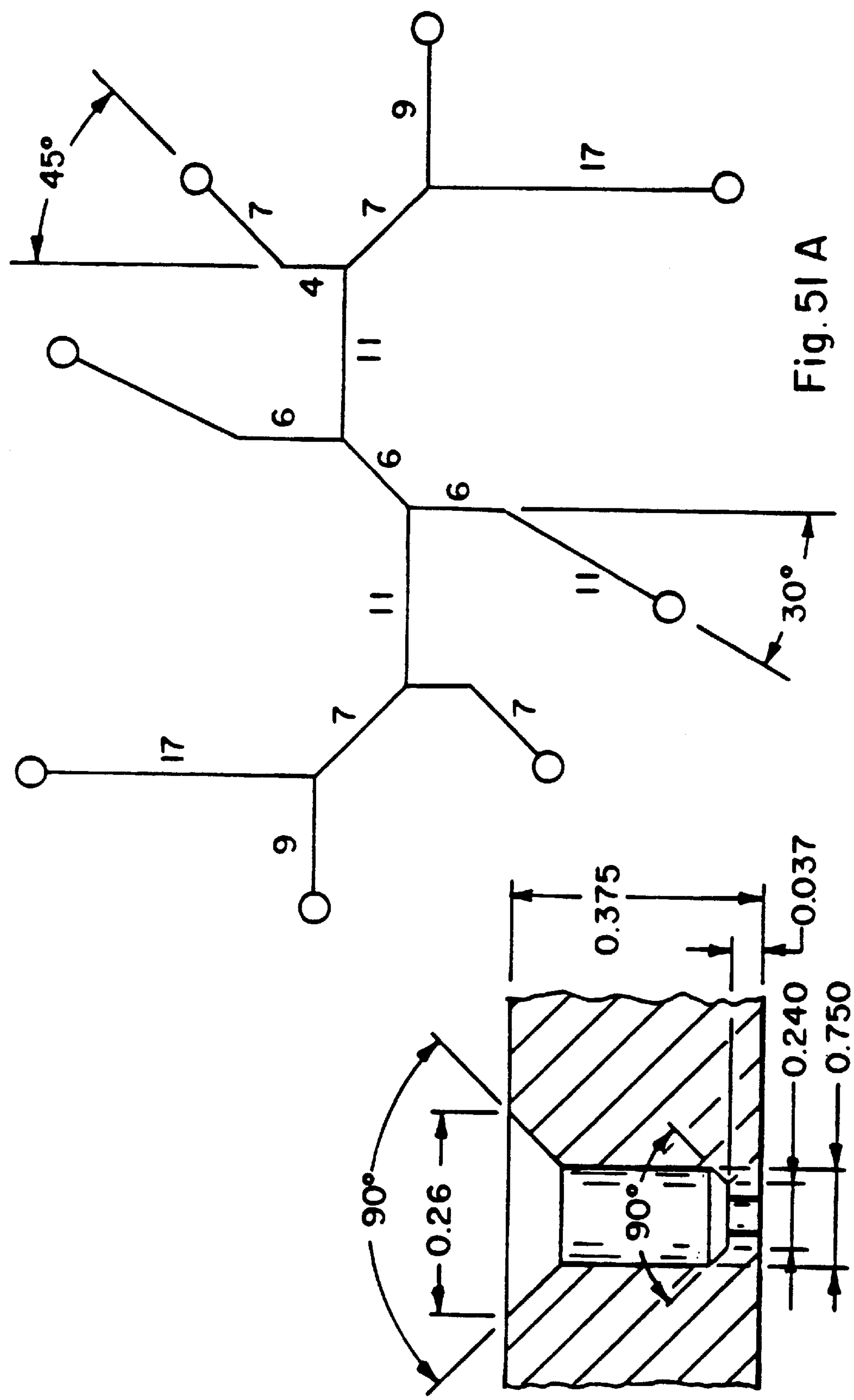
FIGS. 51A, 51B and 52—schematic representations of a spinneret wherein the spinneret holes are oriented in a diagonal pattern on the face of the spinneret with cross-flow quenching directed toward the fiber bundle.
Figure 52:
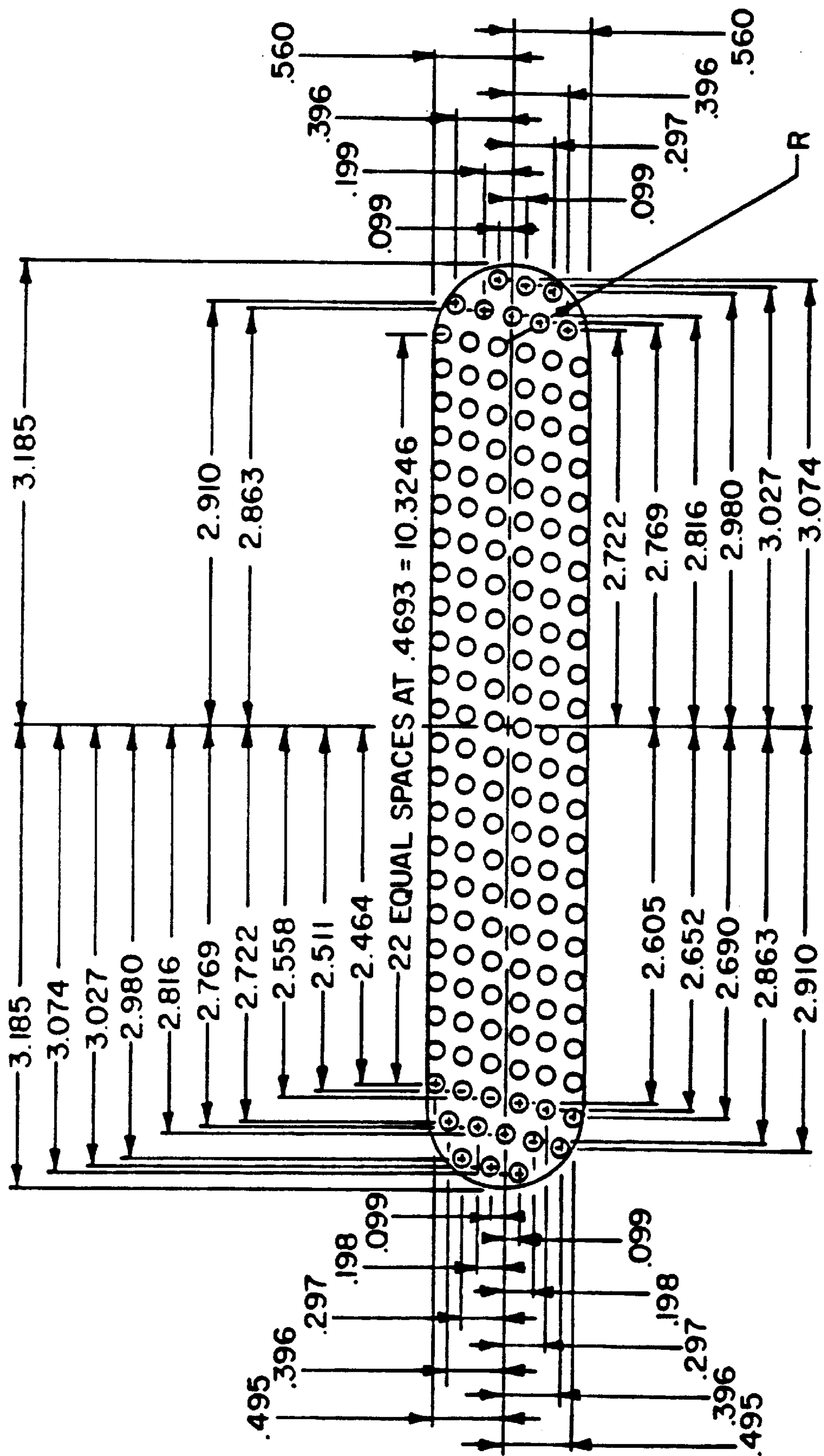

Spontaneously wettable polyester fibers were melt spun from 0.62 IV poly(ethylene terephthalate) polymer using spinneret I 1005 on a unit to make a 20 denier per filament continuous filament fiber. Spinneret I 1005 is described in FIG. 51 and FIG. 52. The slot width in FIG. 51A was 100 microns, and the numbers on the figure are multiples of the slot width. The spinneret holes were oriented in a diagonal pattern on the face of the spinneret with cross-flow quench air directed at a velocity of 250 feet per minute toward the fiber bundle as the fibers traveled down the cabinet. The fiber was spun at 1500 meters per minute with a melt temperature of 280° C. and lubricated with PM 13430 lubricant.

A conventional two stage drafting line was used to process the fiber.

Twelve packages of feed yarn were placed on creel posts and formed into a tow. The tow was drafted by guiding the tow to a first set of rolls running at 16 meters per minute. The yarn left the first rolls and was submerged in a water bath having a water temperature of 70° C. The fiber was guided from the water bath to the second set of rolls which were running at 38 meters per minute. The fiber continued from the second rolls through a steam chamber set at 150° C. to the third rolls running at 40 meters per minute. The tow then went to a puddling jet which placed the tow onto a dryer apron which carried the tow into an oven for shrinking without tension at 150° C. for 1 minute. Helical crimped fiber formed during the shrinking step in the oven. The helical crimped sample was labeled X21741-060-3 and had 8.2 crimps per inch with a crimp amplitude of 0.26 mm. The sample had an a bulky look and an acceptable hand.

TABLE III

3 CM SYN-URINE FLUX FOR SELECTED SURFACTANTS

| Oil Roll RPM | HPMA109 5% in $H_2O$ | PM 13430 E-5 | BR1J35 5% in $H_2O$ | BRIJ99 5% in $H_2O$ | BRIJ700 5% in $H_2O$ | MIL T 3% Active | G1300 5% in $H_2O$ | G1350 5% in $H_2O$ | G144 5% in $H_2O$ | TW60 5% in $H_2O$ |
|---|---|---|---|---|---|---|---|---|---|---|
| 7 | — | 84.7 | — | — | — | 49.7 | 86.5 | — | 128.4 | 98.4 |
| 7 | — | 106.2 | — | — | — | 77.4 | 76.3 | — | 128.0 | 171.3 |
| 10 | — | — | — | — | — | — | — | 133.9 | — | — |
| 10 | — | — | — | — | — | — | — | 117.2 | — | — |
| 15 | 152.1 | 113.4 | 110.4 | 151.5 | 103.5 | 107.5 | 109.5 | 101.9 | 109.1 | 100.0 |
| 15 | 121.5 | 95.3 | 145.1 | 184.7 | 97.6 | 127.7 | 137.6 | 92.3 | 99.4 | 93.2 |
| 25 | 114.7 | 114.8 | 124.5 | 144.7 | 109.6 | 144.6 | 132.9 | 134.5 | 52.9 | 117.5 |
| 25 | 118.0 | 104.1 | 165.5 | 129.0 | 115.6 | 161.0 | 167.1 | 92.8 | 72.6 | 111.2 |
| 35 | 156.4 | 91.8 | 150.1 | 106.3 | 106.3 | 132.2 | 148.7 | 102.6 | 43.6 | 119.7 |
| 35 | 117.4 | 64.0 | 156.6 | 144.3 | 93.8 | 190.5 | 152.1 | 101.8 | 47.4 | 118.8 |
| 45 | 137.0 | 117.9 | 165.8 | 111.4 | 105.9 | 131.2 | 155.4 | 80.3 | — | 101.0 |
| 45 | 167.4 | — | 170.8 | 120.1 | 101.3 | 136.0 | 175.4 | 92.8 | — | 94.2 |
| 55 | 101.2 | 85.9 | 176.6 | 133.6 | 88.0 | 141.7 | 140.9 | — | — | 92.8 |
| 55 | 143.6 | 85.3 | 161.0 | 160.6 | 116.6 | 134.1 | 160.5 | — | — | 94.6 |
| | 167.4 | 117.9 | 176.6 | 184.7 | 116.6 | 190.5 | 175.4 | 134.5 | 128.4 | 171.3 |
| | 156.4 | 114.8 | 170.8 | 16C.6 | 115.6 | 161.0 | 167.1 | 133.9 | 128.0 | 119.7 |
| Best | 152.1 | 113.4 | 165.8 | 151.5 | 109.6 | 144.6 | 160.5 | 117.2 | 109.1 | 118.8 |
| Six | 143.6 | 106.2 | 165.5 | 144.7 | 1a6.5 | 141.7 | 155.4 | 102.6 | 99.4 | 117.5 |
| | 137.0 | 104.1 | 161.0 | 144.3 | 105.9 | 136.0 | 152.1 | 101.9 | 72.6 | 111.2 |
| | 121.5 | 95.3 | 156.6 | 133.6 | 103.5 | 134.1 | 148.7 | 101.8 | 52.9 | 101.0 |
| Avg. Best 6 | 146.3 | 108.6 | 166.1 | 153.2 | 109.6 | 151.3 | 159.9 | 115.3 | 98.4 | 123.3 |
| Std. Dev. Best 6 | 16.1 | 8.4 | 7.1 | 17.8 | 5.4 | 21.4 | 10.0 | 15.8 | 30.4 | 24.6 |

| Oil Roll RPM | IL2535L1 5% in $H_2O$ | IL2535L2 5% in $H_2O$ | RX20 5X in $H_2O$ | RX30 5% in $H_2O$ | RX31 5% in $H_2O$ | TK1674 5% in $H_2O$ | TL1914 5% in $H_2O$ | IL2535L3 5% in $H_2O$ | IL2535L4 5% in $H_2O$ |
|---|---|---|---|---|---|---|---|---|---|
| 7 | 115.5 | 152.5 | 142.6 | 66.0 | 80.3 | 73.3 | 41.0 | 77.3 | 117.6 |
| 7 | 77.0 | 104.5 | 121.6 | 103.8 | 89.6 | 72.9 | 55.9 | 91.0 | 88.8 |
| 10 | — | — | — | — | — | — | — | — | — |
| 10 | — | — | — | — | — | — | — | — | — |
| 15 | 91.7 | 120.2 | 120.9 | 87.9 | 113.4 | 101.4 | 75.6 | 107.2 | 91.2 |
| 15 | 107.8 | 117.8 | 143.0 | 74.7 | 95.1 | 122.3 | 67.8 | 103.3 | 89.2 |
| 25 | 87.8 | 114.1 | 144.0 | 100.8 | 72.2 | 110.9 | 104.0 | 78.5 | 92.7 |
| 25 | 91.1 | 121.9 | 148.9 | 112.0 | 86.2 | 167.6 | 82.6 | 99.7 | 72.4 |
| 35 | 105.6 | 120.4 | 124.9 | 108.7 | 97.2 | 104.1 | 90.6 | 122.6 | 76.2 |
| 35 | 157.6 | 115.6 | 118.7 | 101.8 | 83.4 | 94.6 | 98.2 | 83.4 | 85.5 |
| 45 | 77.7 | 108.9 | 113.2 | 77.4 | 102.4 | 84.9 | 75.5 | 100.4 | 71.6 |
| 45 | 104.0 | 98.4 | 111.6 | 91.3 | 112.0 | 97.0 | 95.9 | 75.8 | 86.9 |
| 55 | 123.6 | 114.0 | 94.0 | 92.4 | 75.7 | 110.3 | 80.1 | 60.7 | 70.2 |
| 55 | 101.0 | 116.4 | 103.0 | 72.3 | 87.0 | 123.6 | 69.6 | 57.6 | 78.5 |
| 157.6 | 152.5 | 148.9 | 112.0 | 113.4 | 167.6 | 104.0 | 122.6 | | |
| | 123.6 | 121.9 | 144.0 | 108.7 | 112.0 | 123.6 | 98.2 | 107.2 | 92.7 |
| Best | 107.8 | 120.4 | 143.0 | 103.8 | 102.4 | 122.3 | 95.9 | 100.4 | 91.2 |
| Six | 105.6 | 120.2 | 142.6 | 101.8 | 97.2 | 110.9 | 90.6 | 100.3 | 89.2 |
| | 104.8 | 117.8 | 124.9 | 100.8 | 95.1 | 110.8 | 82.6 | 99.7 | 88.8 |
| | 101.0 | 116.4 | 121.6 | 92.4 | 89.6 | 104.1 | 80.1 | 91.0 | 86.9 |
| Avg. Best 6 | 116.7 | 124.9 | 137.5 | 103.3 | 101.6 | 123.2 | 91.9 | 103.5 | 94.4 |
| Std. Dev. Best 6 | 21.5 | 13.7 | 11.3 | 6.8 | 9.5 | Z3.0 | 9.3 | 10.7 | 11.5 |

TABLE IV

Relative Ranking of Selected Surfactants Based on 3CM Flux Tests

| Surfactant | Relative Flux* |
|---|---|
| BRIJ35 | 166.1 |
| G1300 | 159.9 |
| BRIJ99 | 153.2 |
| MIL T | 151.3 |
| HPMA109 | 146.3 |
| RX20 | 137.5 |
| IL2535L2 | 124.9 |
| TW60 | 123.3 |
| TL1674 | 123.2 |
| IL2535L1 | 116.7 |
| G1350 | 115.3 |
| BRIJ700 | 109.6 |
| PM 13430 | 108.6 |
| RX30 | 103.3 |
| IL2535L3 | 103.5 |
| RX31 | 101.6 |
| G1441 | 98.4 |
| IL2535L4 | 94.4 |
| TL1914 | 91.9 |

*(Avg. flux)/in cc/hr per gram

TABLE V

Statistical Comparison of Selected Surfactants Based on 3CM Syn-Urine Flux Tests

| | |
|---|---|
| BRIJ 35: | AVG FLUX = 166 (cc/hr-gm), VAR = 49.8 $(cc/hr\text{-}gm)^2$ |
| Equal to: | G1300 (0.82)*, BRIJ99 (0.71), MIL T (0.78) |
| Better than: | HPMA109, RX20, IL2535L2, TW60x**, TL1674x, IL2535L1x, G1350, BRIJ700, LK5570 |
| G1300: | AVG FLUX = 159, VAR = 99.8 |
| Equal to: | BRIJ99 (0.90), MIL T (0.89), HPMA109 (0.67) |
| Better than: | RX20, IL2535L2, TW60, TL1674, IL2535L1, G1350, BRIJ700, LK5500 |
| BRIJ99; | AVG FLUX = 153, VAR = 317 |
| Equal to: | MIL T (0.95), HPMA109 (0.91), RX20 (0.65) |
| Better than: | IL2535L2, TW60, TL1674, IL2535L1, G1350, BRIJ700x, LK5570 |
| MIL T: | AVG FLUX = 151, VAR = 460 |
| Equal to: | HPMA109 (0.93), RX20 (0.78), TW60 (0.60), TL1674 (0.60) |
| Better than: | IL2535L2, IL2535L1, G1350, BRIJ700x, LK5570 |
| HPMA109: | AVG FLUX = 146, VAR = 258 |
| Equal to: | RX20 (0.85, TW60 (0.61), TL1674 (0.60) |
| Better than: | IL2535L2, IL2535L1, G1350, BRIJ700x, LK5570 |
| RX20: | AVG FLUX = 138, VAR = 128 |
| Equal to: | IL2535L2 (0.68), TW60 (0.81), TL1674 (0.79), IL2535L1 (0.60) |
| Better than: | G1350, BRIJ700, LK5570 |
| IL2535L2: | AVG FLUX = 125, VAR = 187 |
| Equal to: | TW60 (0.95), TL1674 (0.95), IL2535L1 (0.90), G1350 (0.85) |
| Better than: | BRIJ700, LK5570 |
| TW60: | AVG FLUX = 123, VAR = 603 |
| Equal to: | TL1674 (0.95), IL2535L1 (0.93), G1350 (0.91), BRIJ700x (0.86), LK5570x |
| TL1674: | AVG FLUX = 123, VAR = 528 |
| Equal to: | IL2535L1 (0.93), G1350 (0.91), BRIJ700x (0.85), LK5500x (0.81) |
| IL2535L1: | AVG FLUX = 116, VAR = 462 |
| Equal to: | G1350 (0.95), BRIJ700 (0.92), LK5570 (0.89) |
| G1350: | AVG FLUX = 115, VAR = 248 |
| Equal to: | BRIJ700x (0.91), LK5570 (0.88) |
| BRIJ700: | AVG FLUX = 110, VAR = 29 |
| Equal to: | LK5570 (0.94) |

*Beta value: probability that means are different when they have been accepted as equal

**x indicates that variances of the two surfactants being compared were different (F test) and separate variances were used in the t test APPENDIX A to Example 32

| SYMBOL | SURFACTANT DESCRIPTION |
|---|---|
| BRIJ35 | Polyoxyethylene (23) lauryl ether (ICI) HLB = 16.9 |
| BRIJ99 | Polyoxyethylene (20) oleyl ether (ICI) HLB = 15.3 |
| BRIJ700 | Polyoxyethylene (100) stearyl ether (ICI) HLB = 18.8 |
| G1300 | G-1300 Polyoxyethylene glyceride ester (ICI) Nionic surfactant HLB = 18.1 |
| G1350 | "ATLAS" G-1350 (ICI) Polyoxylene-polyoxypropylene-sorbitan linoleic phthalic ester |
| G-1441 | G-1441 (ICI), Polyoxyethylene (40) sorbitol, lanolin alcoholysis product |
| HPMA109 | Hyperma A109 (ICI) Modified Polyester Surfactant (98%)/Xylene (2%) HLB = 13–15 |
| IL2535L1 | IL-2535 "Xylene-free/TMA free" Hyperma A109 (ICI) Modified polyester surfactant (HA = high acid no.) |
| IL2535L2 | IL-2535 "Xylene-free/TMA free" Hyperma A109 (ICI) Modified polyester sufactant (LA = low acid no.) |
| IL2535L3 | IL-2535 "Xylene-free/TMA free" Hyperma A109 (ICI) Modified polyester sufactant (LA = low acid no.) |
| IL2535L4 | IL-2535 "Xylene-free/TMA free" Hyperma A109 (ICI) Modified polyester sufactant (LA = low acid no.) |
| PM 13430 | (Eastman Chemical Company) |
| MIL T | MILEASE T (ICI) Polyester/water/other ingredients |
| RX20 | RENEX 20 (ICI) Polyoxyethylene (16) tall oil (100%) (CAS-61791-002) HLB = 13.8 |
| RX30 | RENEX 30 (ICI) Polyoxyethylene (12) tridecyl alcohol (100%) (CAS 24938-91-8) HLB = 14.5 |
| RX31 | RENEX 31 (ICI) Polyoxyethylene (12) tridecyl alcohol (100%) (CAS 24938-91-8) HLB = 15.4 |
| TL-1674 | TL-1674 (ICI) Polyoxyethylene (36) castor oil (100%) (CAS 61791-12-6) |
| TL-1914 | TL-1914 (ICI) Cocoamidopropyl Betaine (CAS-61789-40-0) |
| TW60 | TWEEN 60 (ICI) Polyoxyethylene (20) sorbitan monostearate HLB = 14.9 |

Example 33

Table III summarizes the result for 3 cm syn-urine flux tests performed on several surfactants. Values are tabulated as cc of fluid per hour per gram of fiber. The tests in Table III were conducted to determine the relative performance of these surfactants in transporting aqueous-based fluids. Most of these surfactants were applied from a 5 weight percent solution in water. A range of oil roll speeds was used to cover a relatively wide range of application of each surfactant in an attempt to optimize flux performance.

Examination of the data in Table III reveals that the flux performance of most of the surfactants is relatively flat over the range of oil roll speeds used, although there may be some evidence of decreased performance at low oil roll speed for Milease T and some evidence of decreased performance at high oil roll speed for G-1441. For these reasons, the best six points were selected for each surfactant as representative of optimum performance. The mean and standard deviation of the selected values for each surfactant are also tabulated in Table III.

The average flux for each surfactant was used to calculate the relative flux ranking shown in Table IV. This was done by dividing each average value by the maximum average value, which was 166 for BRIJ 35.

Statistical tests were performed to compare the means for all pairs of surfactants above the dotted line in Table IV using a confidence level of 95 percent. These results are summarized in Table V. Beta values, the probability that the means are different when they have been accepted as equal, are shown in parentheses. Additionally, a small x has been used to indicate when the variances of the two surfactants being compared are statistically different (determined by an F test). PM 13430 was selected as the lower limit for mean comparisons.

Example 34—Measurement of Advancing Contact Angle

The technique (Modified Wilhelmy Slide Method) used to measure the adhesion tension can also be used to measure the Advancing Contact Angle $\theta_a$. The force which is recorded on the microbalance is equal to the adhesion tension times the perimeter of the sample film.

$$\text{Force}=\text{Adhesion Tension}\times\text{Perimeter}=\gamma \cos \theta_a \times p$$

Where $\gamma$ is the surface tension of the fluid (dynes/cm)

$\theta_a$ is the advancing contact angle (degree)

p is the perimeter of the film (cm)

or solving for $\theta_a$:

$$\theta_a = \cos^{-1}\left[\frac{\text{Force}}{\gamma p}\right]$$

For pure fluids and clean surfaces, this is a very simple calculation. However, for the situation which exists when finishes are applied to surfaces and some of this finish comes off in the fluid the effective $\gamma$ is no longer the $\gamma$ of the pure fluid. In most cases the materials which come off are materials which lower significantly the surface tension of the pure fluid (water in this case). Thus, the use of the pure fluid surface tension can cause considerable error in the calculation of $\theta_a$.

To eliminate this error a fluid is made up which contains the pure fluid (water in this case) and a small amount of the material (finish) which was deposited on the sample surface. The amount of the finish added should just exceed the critical micelle level. The surface tension of this fluid is now measured and is used in the $\theta_a$ calculation instead of the pure fluid $\gamma$. The sample is now immersed in this fluid and the force determined. $\theta_a$ is now determined using the surface tension of the pure fluid with finish added and the Force as measured in the pure fluid with finish added. This $\theta_a$ can now be used in $(1-X\ \theta_a)$ expression to determine if the expression is negative.

Example 35 (Base Fiber Preparation)

Poly(ethylene terephthalate) (PET) polymer of 0.69 I.V. was used in this example. I.V. is the inherent viscosity as measured at 25° at a polymer concentration of 0.50 g/100 milliliters (mL) in a suitable solvent such as a mixture of 60% phenol and 40% tetrachloroethane by weight. The polymer was dried to a moisture level of ≦0.003 weight percent in a Patterson Conaform dryer at 120° C. for a period of 8 hours. The polymer was extruded at 285° C. through an Egan extruder, 1.5-inch diameter, with a length to diameter ratio of 28:1. The fiber was extruded through a twelve orifice spinneret wherein each orifice is as shown in FIG. 33 wherein $W_1$=0.100 mm

P=50

V=50

R=50

U=1.3

S=5

$\theta$=90°

The polymer throughput was about 9 pounds (lb)/hour. The average air quench system had a cross-flow configuration. The quench air velocity was 93 feet (ft)/min. No spinning lubricant was applied to the asspun yarn. Fibers of 78 dpf (denier per filament) were wound at 650 meters per minute (MPM) on a Leesona winder.

The surfactants listed in Table IV were applied to the unlubricated base fiber by feeding the yarn at a speed of 20 meters per minute across a kiss roll of approximately 2 1/16 inch diameter. The kiss roll speeds covered a range of 15–55 rpm and the depth of immersion of the kiss roll in the surfactant solutions was ¼ to ⅜ inch. The yarn break angle over the kiss roll was approximately 2–5 degrees.

Example 36—3 cm Uphill Flux Test

Scope and Significance

This method is used to determine the fluid transport rate of capillary transport materials from a reservoir of synthetic urine fluid along an incline to an absorbant. This computer monitored version of the method automatically measures the fluid uptake of the test materials and provides a profile of the weight gain of the transport and absorbant storage materials with time. The spontaneous movement of the fluid up the incline and through the transport material is a quantitative measure of the surface and capillary forces acting on the fluid in opposition to gravity. Uphill transport testing provides a means of comparing rate differences due to the type and size of capillary transport materials as well as surface treatments and geometries. The test can also be used to evaluate the effects of test fluid surface tension as well as different absorbant materials. Finally, the test can be modified to simulate in-use conditions such as removing the reservoir and replacing it later to simulate multiple urine additions.

Summary of Method

The uphill transport test is used to determine the fluid transport rate of capillary transport materials from a reservoir of synthetic urine test fluid along a 10 cm long ramp to an absorbant on an attached platform at 3 cm height. Once the prepared specimen is mounted on the platform/incline, the operator initiates the test according to the instructions given by the computer program by placing the lower end of the transport material in the reservoir of fluid. The test continues for 45 minutes or until terminated by the operator.

Definitions

The terms employed in this method are commonly used in normal laboratory practice and require no special comment.

Safety Precautions

Normal safety precautions and safe handling practices should be observed.

Sources of Error

Fluid transport is very surface and geometry dependent. Surface contamination should be avoided and sample handling should be minimized.

Condition all fiber and fabric samples, including the storage or absorbant material, at least overnight in the laboratory before testing so that the moisture content is controlled by the relative humidity in the laboratory.

The balance is very sensitive to fluid movement in the two reservoirs. Because the fluid transported by the test specimen is the measured response of the test, an accurate tare weight of the fluid before the test is started is essential. The computer does not take this tare weight reading until the specimen to be tested has been identified to the computer and the label is accepted as correct by the operator. Therefore, prior to this time in the program, adjustments in the specimen or test apparatus can be made without affecting the results. All adjustments must be made prior to this point in the testing procedure.

Apparatus

A schematic representation of the apparatus used is in FIG. 39.

Reagents and Materials

SYN-URINE test fluid from Jayco Pharmaceuticals (dyed with food coloring to aid observation)

Transport material of choice in most cases this will be a sheet of PET filaments Absorbant or storage material, such as Bounty® towels or diaper core sections Calibration and Standardization Sample Preparation Weigh a quantity of transport material precut to 20 cm length. Pull out a 9 cm length of Saran Wrap from its 12-inch wide dispenser box. Trim the 11 ½-inch wide wrap to 7 inches which is just the right size to place around the transport material from the bottom or back side to the top side with the ends of the wrap just meeting on the top for minimum overlap (⅛–¼ inch). Wrap loosely with Saran Wrap with about 2 ½ cm of transport material sticking out from the end to be placed in the reservoir and with 8 ½ cm sticking out from the end to be placed in the absorbant. The resulting area of transport material covered with wrap will be 9 cm length by 2 inch width. This covering minimizes evaporation from the transport material between the reservoir and the absorbant. Cut the absorbant material of choice to 2 inch×2 inch size.

Mount the covered transport material on the ramp with its previously assembled absorbant or assemble the transport material/absorbant layers on the ramp. Be sure the filled reservoir has been previously covered with stiff paper or cardboard so the 2–5 cm tail of the transport material will not enter the fluid until the computer has been set up and is ready to start the data collection process. Once the absorbant is in place on the horizontal part of the ramp, apply a load weight over the absorbant (usually 0.5 psi).

Procedure

After turning on the computer, note the test menu and the C> prompt. Type "date" and enter the current date [Return]. Type "UP" to start the test program. Follow the instructions on the computer screen. Stop after you have labeled the sample to be tested. Accepting the labeling as correct will cause the computer to read the balance, and this must not occur until the balance has stabilized with the test specimen and any weights completely in place.

The test is started once the balance is stable by removing the reservoir cover and allowing the transport material to enter the transport fluid. Press [Return] when this occurs to start the computer program that collects the weight data.

The computer program is designed so that two transport processes are followed. The first one is when the fluid moves up the incline of the ramp until the fluid front just reaches the absorbant at the top of the incline. This is the "induction" process. The computer must know when the fluid reaches the absorbant material. Pressing the F5 key tells the computer to calculate the induction process and to begin collecting data for the "transport" process that occurs as the fluid moves in the absorbant material at the top of the ramp.

At the end of the test (45 minutes total or sooner if the test is terminated by the operator) enter the weight of the transport material as requested by the computer. The computer calculates the appropriate times and flux values and puts the results on the printer. The computer is programmed in any conventional way to carry out these calculations. The specific program used in the Examples of this invention is exemplified in Example 24.

Example 37

Fibers were prepared in accordance with the conditions found in U.S. Pat. No. 4,707,409, dated Nov. 17, 1987 by Phillips, et al. In particular, the cross-sections as represented by FIGS. 3, 5 and 7 were prepared. The same lubricant as used in U.S. Pat. No. 4,707,409 was used. The same spinnerets as shown in U.S. Pat. No. 4,707,409 were used to form the fiber. The specific dimensions of the spinneret orifices were the same as in U.S. Pat. No. 4,707,409. The fiber as represented by the cross-section in FIG. 3 had a value for the "X" parameter of about 1.8, a $\theta_a$ of about 22 degrees, and a cos $\theta_a$ of about 0.9. Hypothetical filament cross-section 78 of U.S. Pat. No. 4,707,409 has an X parameter of 1.53. The values for $\theta_a$ and cos $\theta_a$ are the same as those in FIG. 3 discussed above for section 78.

Example 38

Determination of Crimp Amplitude and Crimp Frequency

This describes the determination of crimp amplitude and crimp frequency for fibers in which the crimp is helical (3-dimensional).

The sample was prepared by randomly picking 25 groups of filaments. One filament was picked from each group for testing. Results are the average of the 25 filaments.

A single fiber specimen was placed on a black felt board next to a NBS ruler with one end of the fiber on zero. The relaxed length (Lr) was measured.

The number of crimp peaks (N) were counted with the fiber in the relaxed length. Only top or bottom peaks were counted, but not both. Half peaks at both ends were counted as one. Half counts were rounded up.

The single fiber specimen was grasped with tweezers at one end and held at zero on the ruler, and the other end was extended just enough to remove crimp without stretching the filament. The extended length (Le) was measured.

Definitions

Crimp Frequency=The number of crimps per unit straight length of fiber.

Crimp Amplitude=The depth of the crimp, one-half of the total height of the crimp, measured perpendicular to the major axis along the center line of the helically crimped fiber.

Calculations

For a true helix of pitch angle φ having N total turns, a relaxed length Lr, and an extended (straight) length Le, the following equations apply:

$$Le \cos \phi = N\pi(2A)$$

$$Le \sin \phi = Lr$$

where A is the previously defined crimp amplitude. From these equations, A is readily calculated from the measured values of Lr, Le, and N as follows:

$$\phi = \sin^{-1}(Lr/Le)$$

$$A = \frac{Le}{2N\pi} \cos\phi$$

Crimp frequency (C) as previously defined is calculated as follows:

$$C = \frac{N}{Le}.$$

When Le and Lr are expressed in inches, crimp amplitude has units of inches and crimp frequency has units of crimps per inch.

The invention has been described in detail with particular reference to preferred embodiments thereof, but it will be understood that variations and modifications can be effected within the spirit and scope of the invention. Moreover, all patents, patent applications (published or unpublished, foreign or domestic), literature references or other publications noted above are incorporated herein by reference for any disclosure pertinent to the practice of this invention.

We claim:

1. A process for spontaneously transporting an aqueous fluid comprising contacting a synthetic fiber which is capable of spontaneously transporting water on the surface thereof wherein said fiber satisfies the equation $$(1-X\cos\theta_a)<0,$$

wherein $\theta_a$ is the advancing contact angle of water measured on a flat film made from the same material as the fiber and having the same surface treatment, X is a shape factor of the fiber cross-section that satisfies the following equation $$X=\frac{P_w}{4r+(\pi-2)D}$$

wherein $P_w$ is the wetted perimeter of the fiber and r is the radius of the circumscribed circle circumscribing the fiber cross-section and D is the minor axis dimension across the fiber cross-section, with an aqueous fluid.

2. The process of claim 1 wherein said fiber has an uphill flux value of about 2 to about 60 cc/g/hr, wherein the uphill flux value of said fiber is from about 2 to about 60 cc/g/hr when measured from a reservoir of synthetic urine test fluid along a 20 cm long ramp to an absorbant on an attached platform at 10 cm height.

3. The process of claim 1 wherein said aqueous fluid is selected from the group consisting of water, urine, perspiration, blood and an aqueous ink.

4. The process of claim 1 wherein a part of said fiber is in contact with a source of said aqueous fluid and a different part of said fiber is in contact with a sink.

5. The process of claim 1 wherein said fiber has an uphill flux value of about 2 to about 60 cc/g/hr and an adhesion tension of at least 38 dynes/cm.

6. A process for spontaneously transporting an alcoholic fluid comprising contacting a synthetic fiber which is capable of spontaneously transporting water on the surface thereof wherein said fiber satisfies the equation $$(1-X\cos\theta_a)<0,$$

wherein $\theta_a$ is the advancing contact angle of water measured on a flat film made from the same material as the fiber and having the same surface treatment, X is a shape factor of the fiber cross-section that satisfies the following equation $$X=\frac{P_w}{4r+(\pi-2)D}$$

wherein $P_w$ is the wetted perimeter of the fiber and r is the radius of the circumscribed circle circumscribing the fiber cross-section and D is the minor axis dimension across the fiber cross-section, with an alcoholic fluid.

7. The process of claim 6 wherein said fiber has an uphill flux value of about 2 to about 60 cc/g/hr, wherein the uphill flux value of said fiber is from about 2 to about 60 cc/g/hr when measured from a reservoir of synthetic urine test fluid along a 20 cm long ramp to an absorbant on an attached platform at 10 cm height.

8. The process of claim 6 wherein said alcoholic fluid comprises at least about 70% by weight of an alcohol which is selected from the group consisting of methanol, ethanol, n-propanol and iso-propanol.

* * * * *